US009366668B2

(12) United States Patent
Rao et al.

(10) Patent No.: US 9,366,668 B2
(45) Date of Patent: Jun. 14, 2016

(54) DEVICE, ARRAY, AND METHODS FOR DISEASE DETECTION AND ANALYSIS

(71) Applicants: Rupa S. Rao, Stockton, CA (US); Stephen M. Lane, Oakland, CA (US); Dennis L. Matthews, Moss Beach, CA (US); Matthew A. Coleman, Oakland, CA (US)

(72) Inventors: Rupa S. Rao, Stockton, CA (US); Stephen M. Lane, Oakland, CA (US); Dennis L. Matthews, Moss Beach, CA (US); Matthew A. Coleman, Oakland, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 14/465,796

(22) Filed: Aug. 21, 2014

(65) Prior Publication Data

US 2015/0087543 A1    Mar. 26, 2015

Related U.S. Application Data

(63) Continuation of application No. 12/031,625, filed on Feb. 14, 2008, now abandoned.

(60) Provisional application No. 60/902,147, filed on Feb. 15, 2007.

(51) Int. Cl.
*G01N 33/543* (2006.01)
*B01J 19/00* (2006.01)
*C40B 60/12* (2006.01)
*B01L 3/00* (2006.01)

(52) U.S. Cl.
CPC .......... *G01N 33/543* (2013.01); *B01J 19/0046* (2013.01); *C40B 60/12* (2013.01); *B01J 2219/00385* (2013.01); *B01J 2219/00549* (2013.01); *B01J 2219/00612* (2013.01); *B01J 2219/00621* (2013.01); *B01J 2219/00626* (2013.01); *B01J 2219/00637* (2013.01); *B01J 2219/00725* (2013.01); *B01L 3/5025* (2013.01); *B01L 3/5027* (2013.01); *B01L 3/50273* (2013.01)

(58) Field of Classification Search
None
See application file for complete search history.

(56) References Cited

U.S. PATENT DOCUMENTS

| 4,707,438 | A | 11/1987 | Keydar |
| 4,938,224 | A | 7/1990 | Rysavy |
| 5,843,651 | A | 12/1998 | Stimpson et al. |
| 2002/0182600 | A1 | 12/2002 | Smith |
| 2003/0109067 | A1 | 6/2003 | Brown et al. |
| 2003/0228631 | A1 | 12/2003 | Hu |
| 2005/0130322 | A1 | 6/2005 | Beesley et al. |
| 2008/0261243 | A1* | 10/2008 | Lorence et al. ............ 435/7.23 |

FOREIGN PATENT DOCUMENTS

WO    WO-2006/041959 A2    4/2006

OTHER PUBLICATIONS

Eriksson, Integrated matrix metalloprotease assays in CD—Microlaboratories, 34 pages, 2004, retrieved from http://www.ibg.uu.se/digitalAssets/165/165169_3eriksson-lena-arbete.pdf on May 3, 2014.*
Monoclonal Mouse anti-CA15-3 antibody, retrieved from http://1degreebio.org/reagents/product/942571/?qid=0 on May 3, 2015, 2015, 1 page.*
Hao et al., Osteopontin Reduces Polyspermy During In Vitro Fertilization of Porcine Oocytes, Biology of Reproduction, 75, 726-733 (2006).*
Ali et al., "Relationship of Serum HER-2/neu and Serum CA 15-3 in Patients with Metastatic Breast Cancer", Clinical Chemistry 48:8 1314-1320, 2002.
Askari M.D., et al., "Simultaneous detection of the tumor suppressor FHIT gene and protein using the multi-functional biochip," Cancer Detect Prev. 26, 331342 (2002).
Brooks, D., et al. "RAMP: A Rapid, Quantitative Whole Blood Immunochromatographic Platform for Pointof-Care Testing," Clinical Chemistry 45, pp. 1676-1678 (1999).
Coleman M.A., et al., "Identification of chromatin-related protein interactions using protein microarrays," Proteomics. In Press (2003).
Coleman R.E., et al., "Clinical course and prognostic factors following bone recurrence from breast cancer," British Journal of Cancer 77, 336-340 (1998).
de Vicente et al. "Expression and clinical significance of matrix metalloproteinase-2 and matrix metalloproteinase-9 in oral squamous cell carcinoma", Oral Oncology (2005) 41 :283-93.
Delehanty, J., et al., "A microarray immunoassay for simultaneous detection of proteins and bacteria," Anal. Chem., vol. 74, pp. 5681-5687 (2002).
Denhardt et al. Osteopontin as a means to cope with environmental insults: regulation of inflammation, tissue remodeling, and cell survival. J. Clin. Invest. (2001), 107(9):1055-61.
Feldstein, M., et al., "Array Biosensor: Optical and Fluidics Systems," Journal of Biomedical Microdevices, vol. 1, No. 2, pp. 138-153 (1999).

(Continued)

*Primary Examiner* — Galina Yakoleva
*Assistant Examiner* — Andrea S Grossman
(74) *Attorney, Agent, or Firm* — Fenwick & West, LLP

(57) ABSTRACT

A device and array coupled to capture molecules are provided. Specifically, the device and array can be used for detecting the presence and concentration of biomarkers in a sample from a subject. The device and array can also allow the use of a method for scoring a sample for, e.g., the purpose of diagnosing a disease. The method can also be advantageous to applications where there is a need to accurately determine the disease stage of a subject for the purpose of making therapeutic decisions.

4 Claims, 31 Drawing Sheets

(56) References Cited

OTHER PUBLICATIONS

Fields, M., et al., "Ovarian cancer screening: a look at the evidence," Clinical Journal of Oncology Nursing, Feb. 2006, pp. 77-81, vol. 10, No. 1.

Gion M. et al, "The Tumor associated antigen CA 15.3 in primary breast cancer. Evaluation of 667 cases", Br. J. Cancer (1991), vol. 63, pp. 809-813.

Harris M., "A comparison of the metastatic pattern of infiltrating lobular carcinoma and infiltrating duct carcinoma of the breast," British Journal of Cancer 50, 23-30 (1984).

Has Holzner U., et al., "CA 242 in comparison with established tumour markers in colorectal, pancreatic and lung cancer," Anticancer Res. 19, 24 77-2480 ( 1999).

Huang R.P., et al., "Simultaneous detection of multiple cytokines from conditioned media and patient's sera by an antibody-based protein may system," Anal Biochem. 294, 55-62. (2001).

Jeong Os, et al., "Simultaneous Quantitative Determination of Multiple Analytes with Fluorescence-Tagged Probes by Immunochromatoaraphv," Korean J Biol Sci 7, 89-92 (2003).

Joos, T.O., et al., "A Microarray enzyme linked immunosorbent assay for autoimmune diagnostics," Electrophoresis, vol. 21, pp. 2641-2650 (2000).

Kusnezow, W., et al., "Kinetics of antigen binding to antibody microspots: strong limitation by mass transport to the surface," Proteomics 6, 794-803 (2006).

Kuriyama, M., et al., "Quantitation of prostate-specific antigen in serum by a sensitive enzyme immunoassay," Cancer Research, vol. 40, pp. 4658-4662 (1980).

Lee-Lewandrowski, E., et al., "Selected topics in point-of-care testing—Urinalysis, pregnancy testing, microbiology, fecal occult blood, and other tests," Clin Lab Med 21, 389 (2001 ).

Liedberg, B., et al., "Surface plasmon resonance for gas detection and biosensing," Sensors and Actuators, 4, 299-304 (1983).

Lou, SC, et al., "One-step competitive immunochromatographic assay for semiquantitative determination of lipoprotein(a) in plasma," Clinical Chemistry, 1993, vol. 39, No. 4, pp. 619-624.

Mayo Clinic, "Breast Cancer Staging", available at http://www.mayoclinic.com/health/breast-cancer.staging/BR00022 (last visited Jul. 7, 2013).

Marks J. et al., "Overexpression of P53 and HER-2/neu proteins as prognostic markers in early stage breast cancer" Annals of Surgery, vol. 29(4), pp. 332-341, 1994.

Menard S. et al. "Biologic and therapeutic role of HER2 in cancer", Oncogene (2003) 22:6570-78.

Panteghini, M., et al., "Characterization of a rapid immunochromatographic assay for simultaneous detection of high concentrations of myoglobin and CK-MB in whole blood," Clin. Chem., Aug. 1, 1996, vol. 42, Issue 8, pp. 1292-1293.

Papsidero, L.D., et al., "A prostate antigen in sera of prostatic cancer patients," Cancer Research, vol. 40, pp. 2428-2432 (1980).

Ponce, C., et al., "Validation of a rapid reliable test for the diagnosis of Chagas' disease in blood banks and medical emergencies in Central America," The Journal of Clinical Microbiology, pp. 5065-5068 (2005).

Pugia, MJ, et al., "Microfluidic tool box as technology platform for hand-held diagnostics," Clin Chem. 2005, vol. 51, No. 10, pp. 1923-1932.

Qian S, B.H. "A mathematical model of lateral flow bioreactions applied to sandwich assays," Anal Biochem. 322, 89-98 (2003).

R&D Systems, Inc., "Monoclonal anti-human ErbB2-phycoerythrin", available at http://www.rndsystems.com/pdf/FAB1129A.pdf (last visited Jun. 12, 2009).

R&D Systems, Inc., Monoclonal anti-human osteopontin (OPN) antibody, available at http://www.rndsystems.com/pdf/mab1433.pdf (last visited Jun. 12, 2009).

Rao, R.S., et al., "A comparison of multiplexed techniques for comparison of bacterial and viral proteins," J. Proteome Res., vol. 3, pp. 736-742 (2004).

Rao, R.S., "Comparison of Multiplexed Techniques for Detection of Bacterial and Viral Proteins," Presented at the 4th Annual UC Wide Biomedical Engineering Symposium, San Diego, CA, Jun. 2003.

Saad S. et al., "Cancer Cell-associated Fibronectin Induces Release of Matrix Metalloproteinase-2 from Normal Fibroblasts", Cancer Research 62, 283-289, 2002.

Sahu A, S.A., et al., "Binding Kinetics, Structure-Activity Relationship, and Biotransformation of the Complement Inhibitor Comostatin," J Immunol. 165, 2491-2499 (2000).

Schuck, P. "Use of surface plasmon resonance to probe the equilibrium and dynamic aspects of interactions between biological macromolecules," Annual Review of Biophysics and Biomolecular Structure 26, 541-566 (1997).

Schweitzer B., et al., "Measuring proteins on Microarrays," Curr Opin Biotechnol 12, 14-19 (2002).

Sheen-Chen S. et al., "Serum levels of Matrix Metalloproteinase 2 in patients with Breast Cancer", Cancer Letters 173 (2001 ), 79-82.

Short Guide for Developing Immunochromatographic Test Strips (Bedford, MA: Millipore Corp., 1996).

Singhal H. et al., "Elevated Plasma Osteopontin in Metastatic Breast Cancer Associated with Increased Tumor Burden and Decreased Survival", Clinical Cancer Research, 3:605-611, 1997.

Song S. et al., "Simultaneous multianalysis for tumor markers by antibody fragments microarray system", Analytica Chimica Acta 510 (2004) 147-152.

Stenberg, E., et al., "Quantitative determination of surface concentration of protein with surface plasmon resonance using radiolabeled proteins," J. Coll. Interface Sci. 143, 513-526 (1991).

Stoll et al. Protein microarray technology. Frontiers in Bioscience (2002) 7:c12-32.

Sugawara, Y, et al., "Development of a highly sensitive enzyme-linked immunosorbent assay based on polyclonal antibodies for the detection of polychlorinated dibenzo-p-dioxins," Anal Chem., vol. 70, pp. 1092-1099 ( 1998).

Taitt, C.R., et al., "A Portable Array Biosensor for Detecting Multiple Analytes in Complex Samples,"Microbial Ecology 47, 175-185 (2004).

Vijayendran, R., et al., "A Computational Reaction-Diffusion Model for the Analysis of Transport-Limited Kinetics," Anal. Chem., vol. 71, pp. 5405-5412 (1999).

Website of catalog for ErbB2/HER2 dated Nov. 8, 2007, R&D Systems, Inc., http://web.archive.org/web/20071108070952/http://www.rndsystems.com/product_results.aspx?m=1397&c=O (last visited Jun. 12, 2009).

Welch, D.R., et al., "Genetic and epigenetic regulation of human breast cancer progression and metastasis," Endocrine-Related Cancer, vol. 5, pp. 155-197 (1998).

Wilson M. et al. "Multiplex measurement of seven tumor markers using an electrochemical protein chip", Anal. Chem, (2006) 78:6476-83.

Yeatman T.J, "The future of clinical cancer management: one tumor, one chip," Am Surg. 639, 41-44 (2003).

Zimmermann, M., et al., "Modeling and Optimization of High-Sensitivity, Low-Volume Microfluidic-Based Surface Immunoassays," Biomedical Microdevices, 2005, pp. 99-110, vol. 7, No. 2.

Alegria-Schaffer A., et al, "Performing and optimizing Western blots with an emphasis on chemiluminescent detection", Methods Enzymol., 2009; pp. 573-599, vol. 463.

Ivey R. et al., "Antibody-Based Screen for Ionizing Radiation-Dependent Changes in the Mammalian Proteome for Use in Biodosimetry", Radiat Res., 2009, pp. 549-561, vol. 171(5).

Leng S., et al. "ELISA and Multiplex Technologies for Cytokine Measurement in Inflammation and Aging Research", Journal of Gerontology: Medical Sciences, 2008, pp. 879-884, vol. 63A(8).

Ligler, F., et al., "Array biosensor for detection of toxins," Anal Bioanal Chem, 2003, pp. 469-477, vol. 377.

Vossen, J.L., "Transparent Conducting Films," Physics of Thin Films, 1977, pp. 9-45.

\* cited by examiner (A) Her-2 ELISA standard curve (B) MMP-2 ELISA standard curve (C) CA 15-3 ELISA standard curve (D) Osteopontin ELISA standard curve (E) VEGF ELISA standard curve (A) Her-2

(B) MMP-2

(C) CA 15-3

(D) Osteopontin (E) VEGF (A) Her-2

(B) MMP-2

(C) CA 15-3

(D) Osteopontin (E) VEGF (F) Her-2

(G) MMP-2

(H) CA 15-3

(I) Osteopontin (J) VEGF (A) Her-2

(B) MMP-2

(C) CA 15-3

(D) Osteopontin (E) VEGF (A) Standard Curve for Her-2

(B) Standard Curve for MMP-2

(C) Standard Curve for CA 15-3

(D) Standard Curve for OPN (A) Her-2     CA 15-3   OPN
(B) Her-2     OPN       CA 15-3
(C) CA 15-3   OPN       Her-2
(D) CA 15-3   Her-2     OPN
(E) OPN       CA 15-3   Her-2
(F) OPN       Her-2     CA 15-3

→ Direction of flow

FIG. 21

(A) Her-2

(B) MMP-2

DEVICE, ARRAY, AND METHODS FOR DISEASE DETECTION AND ANALYSIS

CROSS REFERENCE TO RELATED APPLICATIONS

This application is a continuation of U.S. patent application Ser. No. 12/031,625, filed Feb. 14, 2008 (pending) which claims the benefit of U.S. Provisional Application No. 60/902,147, filed Feb. 15, 2007, the entire disclosure of which is hereby incorporated by reference in its entirety for all purposes.

STATEMENT REGARDING FEDERALLY SPONSORED RESEARCH OR DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

1. Field of the Invention

The invention relates to the fields of biology and chemistry.

2. Description of the Related Art

Research over the past decade has focused on discovering new biomarkers that provide accurate diagnosis of disease, guide therapeutic decision making, and predict the future patterns of disease. Cancer antigen (CA)-125 and Carcinoembryonic antigen (CEA) have both shown promise as biomarkers for ovarian and colorectal cancer, respectively (Fields M M, C. E. Ovarian cancer screening: a look at the evidence. Clin J Oncol Nurs. 10, 77-81 (2006); Hasholzner U, S. P., Reiter W, Zimmermann A, Hofmann K, Schalhorn A. CA 242 in comparison with established tumour markers in colorectal, pancreatic and lung cancer. Anticancer Res. 19, 2477-2480 (1999)). However, while these biomarkers have shown some potential for possible specific detection of ovarian and colon cancers, no single marker has yet been identified for breast cancer. This can be due to the fact that breast cancer is not a single disease, but a genetically heterogeneous set of diseases, thus suggesting that it can not be possible for breast cancer to be diagnosed with any single marker. The present invention addresses this need by providing multiple, mutually complementary biomarkers that provide a sensitive diagnostic assay for breast cancer.

Point of care (POC) devices and systems can process samples for a number of different types of biomarkers in a variety of settings, such as clinical laboratories, patients' bedside and doctors' offices. Various forms of single biomarker POC technologies are available including Lateral flow assays (LFA) (Panteghini M, P. F. Characterization of a rapid immunochromatographic assay for simultaneous detection of high concentrations of myoglobin and CK-MB in whole blood. Clin Chem Clin Biochem 42, 1292-1293. (1996); Millipore Corp A Short Guide: Developing Immuno-chromatographic Test Strips. (1996); Lou S C, P. C., Ching S, Gordon J. One-step competitive immunochromatographic assay for semiquantitative determination of lipoprotein (a) in plasma. J. Clin Chem 39 (1993); Lee-Lewandrowski E, L. K. Selected topics in point-of-care testing—Urinalysis, pregnancy testing, microbiology, fecal occult blood, and other tests. Clin Lab Med 21, 389 (2001)), Disposable microchips (Pugia M J, B. G., Peters R P, Profitt J A, Kadel K, Willms T, Sommer R, Kuo H H, Schulman L S. Microfluidic tool box as technology platform for hand-held diagnostics. Clin Chem. 51, 1923-1932 (2005)), the RAMP™ platform (Donald E. Brooks, D. V. D., Paul C. Harris, Joanne E. Harris, Mark E. Miller, Andrew D. Olal, Linda J. Spiller and Zongen C. Xie RAMP: A Rapid, Quantitative Whole Blood Immunochromatographic Platform for Point-of-Care Testing. Clinical Chemistry 45, 1676-1678 (1999)), and the Dual Path Platform (DPP) technology (Carlos Ponce, E. P., Elizabeth Vinelli, Alberto Montoya, Vilma de Aguilar, Antonio Gonzalez, Bianca Zingales, Rafael R. Aldao, Mariano J. Levin, Javan Esfandiari, Eufrosina S. Umezawa, Alejandro O. Luquetti, and José Franco da Silveira. Validation of a rapid reliable test for the diagnosis of Chagas' disease in blood banks and medical emergencies in Central America. The Journal of Clinical Microbiology, 5065-5068 (2005)). In addition, multiplexed LFAs have also been developed (Jeong D S, C. E. Simultaneous Quantitative Determination of Multiple Analytes with Fluorescence-Tagged Probes by Immunochromatography. Korean J Biol Sci 7, 89-92 (2003)).

Multiplexed LFAs, although sensitive and specific, require elaborate imaging devices for sensitive quantification, thus limiting application at the POC. Another form of multiplexed assay are microfabricated flow channels which pass a sample over an immobilized array (Delehanty J. B. Ligler F. S A microarray immunoassay for simultaneous detection of proteins and bacteria. Anal. Chem. 74, 5681-5687 (2002); C. R. Taitt, J. P. G., Y. S. Shubin, L. C. Shriver-Lake, K. E. Sapsford3, A. Rasooly, F. S. Ligler A Portable Array Biosensor for Detecting Multiple Analytes in Complex Samples. Microbial Ecology 47, 175-185 (2004); Frances S. Ligler, C. R. T., Lisa C. Shriver-Lake, Kim E, Sapsford, Yura Shubin, Joel P. Golden Array biosensor for detection of toxins. Anal Bioanal Chem 377, 469-477 (2003); Mark J. Feldstein, J. P. G., Chris A. Rowe, Brian D. MacCraith, Frances S. Ligler Array Biosensor: Optical and Fluidics Systems. Journal of Biomedical Microdevices 1, 138-153 (1999)). Use of these assays requires that the sample, detection antibodies, and wash buffers be sequentially introduced at one end of the chamber and drawn over the microarray surface using a peristaltic pump. These assays demonstrate better multiplexed sensitivities as compared to the LFAs, however, they involve sequential detection along the length of the strip rather than simultaneous detection, which limits the number of biomarkers that can be simultaneously analyzed due to the number of capture zones that can be created along the length of the strip. In addition, the flow channels are made using polydimethylsiloxane (PDMS) as the material which requires elaborate microfabrication facilities to manufacture. Also, the fluid exchange through the channels was achieved using a peristaltic pump, and the assay involved multiple incubation and wash steps, making it challenging to automate and reduce this device to a small, rugged portable form.

The present invention addresses these problems by providing a channel flow device that allows simple, rapid, and sensitive detection of multiple biomarkers.

SUMMARY

Disclosed herein is a detection device. In one aspect, the detection device includes a solid support including a plurality of distinct capture molecule groups, each distinct capture molecule group including a plurality of capture molecules specific for a biomarker, wherein the plurality of distinct capture molecule groups is specific for a plurality of biomarkers; a cover plate, wherein the cover plate forms an upper surface positioned above the solid support; a vertical support, wherein the vertical support forms a connection between the solid support and the cover plate, the connection forming at least one channel around the capture molecule groups, and wherein the channel includes a first end and a second end and wherein the first end of the channel includes an opening; and an absorbent material connected to the second end. In another aspect of the detection device, the solid support includes glass. In another aspect of the detection device the solid support includes a glass slide.

In one embodiment, the capture molecules include antibodies. In another embodiment, the capture molecules are specific for biomarkers selected from Her-2, MMP-2, CA 15-3, VEGF, and OPN. In another embodiment, the capture molecules are specific for Her-2, MMP-2, CA 15-3, VEGF, OPN, p53, CA 125, and SER. In another embodiment, the capture molecules are specific for Her-2, MMP-2, CA 15-3, and OPN. In another embodiment, the capture molecules are Clone 191924, Clone 36006.211, Clone M8071022, and Clone 190312. In another embodiment, the capture molecules are blocked by a blocking agent. In another embodiment, the plurality of distinct groups of capture molecules is arranged in an array format. In another embodiment, the solid support includes at least two capture molecule groups including identical capture molecules, and each of the at least two capture molecule groups including a different number of capture molecules.

In one embodiment, the cover plate includes glass. In another embodiment, the cover plate is a glass cover slip. In one embodiment, the vertical support includes adhesive silicone. In one embodiment, the absorbent material includes a Hi-Flow Plus Nitrocellulose Membrane HF240.

In another aspect, the detection device includes a glass slide including an array of a plurality of distinct groups of antibodies cross-linked to the slide, each distinct group specific for a biomarker selected from Her-2, MMP-2, CA 15-3, and OPN; a glass cover slip positioned above the solid support; and a silicone adhesive connection between the glass slide and the glass cover slip forming at least one channel around the antibody groups, and wherein the channel includes a first open end and a second end connected to a Hi-Flow Plus Nitrocellulose Membrane HF240.

In one embodiment, the detection device further includes a component for detecting biomarkers bound to the solid support. In a related embodiment, the component includes an optical reader and a screen for displaying output from the optical reader.

Also disclosed herein is a method for determining the presence or absence of a plurality of biomarkers in a sample, including: acquiring a liquid mixture, wherein the mixture includes the sample; applying the mixture to the open first end of the at least one channel of the device, described above; allowing the mixture to flow through the at least one channel over the solid support; absorbing the mixture with the absorbent material connected to the second end; and detecting the presence of biomarkers on the solid support, wherein presence of the biomarkers on the solid support indicates the presence of the biomarkers in the sample.

In one embodiment of the method for determining the presence or absence of a plurality of biomarkers in a sample, the detection device described above, is used, the device includes capture molecules including antibodies and the liquid mixture includes the sample, at least one detector antibody, and at least one fluorescent reporter, and the method further including the steps of analyzing the sample with an optical reader to determine the presence or absence of the plurality of biomarkers in the sample; and outputting the data, wherein the data include the presence or absence of the plurality of biomarkers in the sample. In another embodiment of the method for determining the presence or absence of a plurality of biomarkers in a sample, the detection device, described above, includes capture molecules specific for a plurality of biomarkers selected from the group consisting of CA 15-3, OPN, Her-2, and MMP-2. In another embodiment, the sample includes human blood serum.

Also disclosed herein is an array of antibodies immobilized on a solid support, the array including: a plurality of distinct antibody groups, each distinct antibody group including a plurality of antibodies specific for a biomarker, wherein the plurality of distinct antibody groups is specific for a plurality of biomarkers, and wherein the plurality of biomarkers include CA 15-3, OPN, Her-2, and MMP-2.

Also disclosed herein is a method for determining protein concentration data in a sample with an array, including: acquiring a mixture, wherein the mixture is in a liquid state, and wherein the mixture includes the sample from a mammalian subject, a detector antibody, and a fluorescent reporter; applying the mixture to the array described above; analyzing the sample with a reader to determine the concentration of the plurality of biomarkers in the sample; and outputting the data, wherein the data include protein concentration data for the plurality of biomarkers, and wherein the plurality of biomarkers include CA 15-3, OPN, Her-2, and MMP-2.

Also disclosed herein is a method of scoring a sample acquired from a mammalian subject, including: obtaining a first dataset including quantitative data associated with a plurality of biomarkers associated with breast disease and the plurality of biomarkers include CA 15-3, and OPN, wherein the data include measured values obtained from the sample; analyzing the first dataset against a second dataset to produce a score for the sample; and outputting the score.

In one embodiment, the plurality of biomarkers includes Her-2. In another embodiment, the plurality of biomarkers includes MMP-2. In another embodiment, the plurality of biomarkers includes Her-2 and MMP-2. In another embodiment, the plurality of biomarkers includes Her-2, MMP-2, VEGF, p53, CA 125, and SER. In another embodiment, the quantitative data includes protein concentrations. In another embodiment, the data is immunoassay data. In another embodiment, the protein concentrations are obtained using an immunoassay including antibodies. In a related embodiment, the immunoassay is a sandwich immunoassay. In another embodiment, the protein concentrations are obtained using a multiplexed channel flow-based device. In another embodiment, the antibodies of the immunoassay are Clone 191924, Clone 36006.211, Clone M8071022, Clone 190312, and Clone A183C-13G8.

In another embodiment, the analyzing step includes use of a predictive model. In a related embodiment, the predictive model is developed using principal component analysis. In another related embodiment, the predictive model is developed using linear discriminant analysis. In another embodiment, the analyzing step includes categorizing the sample into categories according to a score produced with the predictive model. In a related embodiment, the categorization is selected from the group consisting of: a healthy categorization, an early-stage disease categorization, and a late-stage disease categorization. In another related embodiment, a probability that the categorization is correct is at least 60%, at least 70%, at least 80%, at least 87%, at least 90%, and at least 95%.

In another embodiment, the method further includes comparing the score to a second score determined for a second sample obtained from the mammalian subject. In a related embodiment, wherein a difference between the first score and the second score indicates a disease stage of breast cancer. In another embodiment, wherein the mammalian subject is a human subject. In another embodiment, wherein the score is used to diagnose a neoplastic breast disease. In another embodiment, wherein the breast disease is breast cancer.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 21 shows fluorescence images of the sandwich LFA.

DETAILED DESCRIPTION

Figure 1:
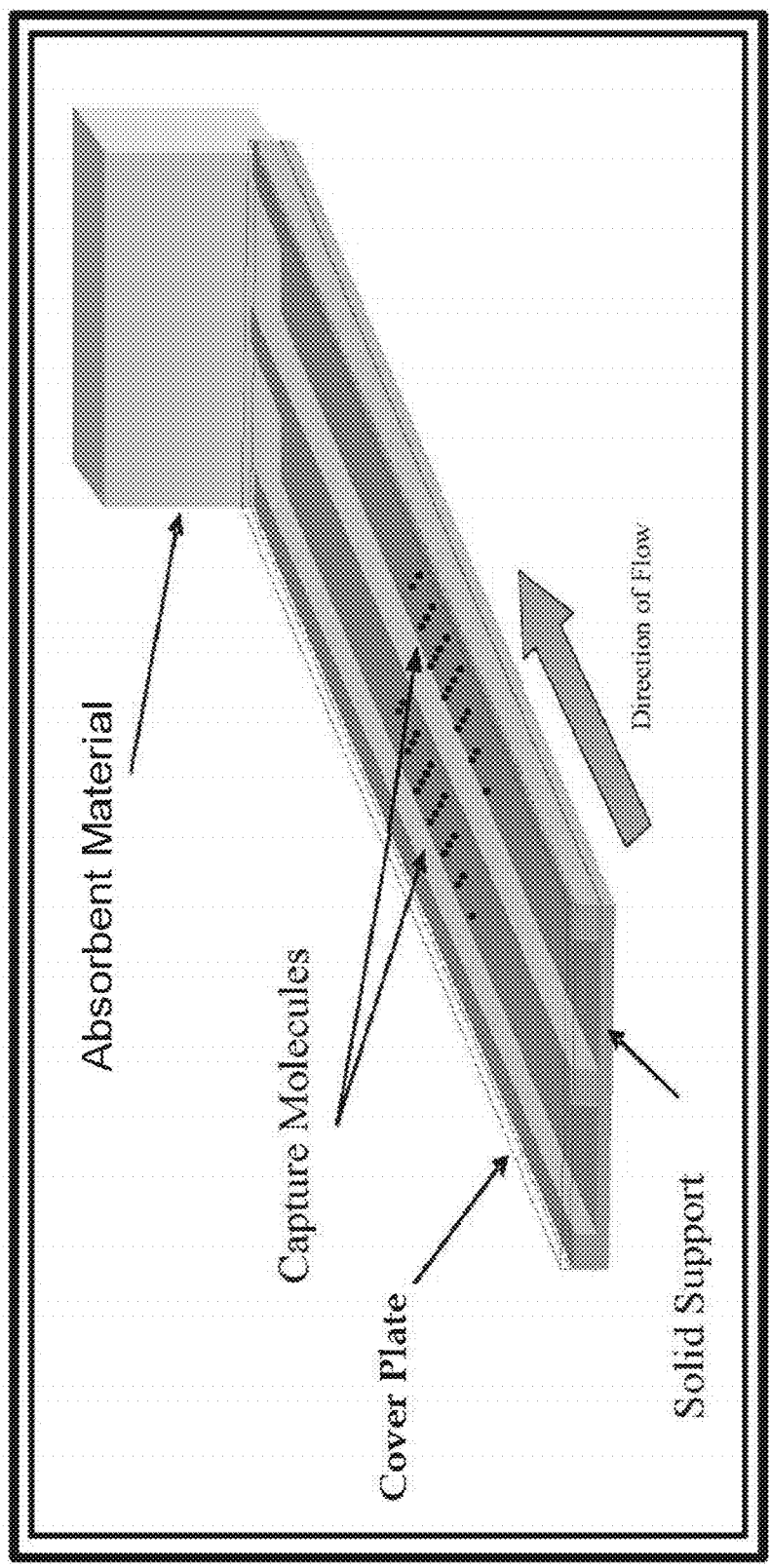
FIG. 1 is a schematic representation of the point of care channel flow-based immunoassay detection device.

Briefly, and as described in more detail below, described herein is a channel flow based immunoassay detection device for determining the presence and/or concentration of a plurality of biomarkers in a sample. Also disclosed are methods of using the device, and arrays of capture molecules, e.g., antibodies, for use with the device. In one embodiment, the device is used to detect a plurality of biomarkers related to breast cancer. Described herein are methods of scoring a sample using data associated with the breast cancer biomarkers.

Advantages of this approach are numerous. The device provides the ability to perform multiplexed analysis of multiple biomarkers in a format that is simple to use, amenable to automation, and in a small, rugged format. The device has been developed in a point of care (POC) format, allowing for rapid diagnostic assay, and facilitating faster therapeutic decisions and possible increased patient survival rates.

The device can be used to diagnose and prescribe treatment for a wide variety of medical conditions, especially cancers, heart diseases, respiratory diseases, and microbial infections. In one embodiment, the device is used to diagnose breast cancer.

Also disclosed is a multiplexed immunoassay to detect a set of biomarkers associated with breast cancer. The immunoassay can accurately detect a panel of two, three, four, five, six, seven, or eight biomarkers from the sera of breast cancer patients and distinguish between control, early stage, and metastatic breast cancer populations. The immunoassay was shown to predict the stage of unknown sample. The assay can be used can be used along with mammography for result validation and in between annual mammograms to diagnose rapidly-growing tumors. The advantage of the multiplex assay is the ability to determine the levels of these markers simultaneously, thus reducing time, effort, overall volume of reagent and patient sample. Such a panel can offer a complete range of tests such as diagnosis, prognosis, treatment options and treatment monitoring in a single assay, providing additional information enabling rapid diagnosis and improved patient survival rates.

DEFINITIONS

Terms used in the claims and specification are defined as set forth below unless otherwise specified.

A "capture molecule" is a molecule that is immobilized on a surface. The capture molecule generally, but not necessarily, binds to a target or target molecule, e.g., a biomarker. The capture molecule is typically an antibody, a peptide, or a protein. In the case of a solid-phase immunoassay, the capture molecule is immobilized on the surface of a solid support and is an antibody specific to the target, an antigen or epitope, to be detected. The capture molecule can be labeled, e.g., a fluorescently labeled antibody or protein. The capture molecule can or can not be capable of binding to just the target. Capture molecules can include e.g., RNA, DNA, peptides, antibodies, aptamers, and protein-based aptamers. In one embodiment the capture molecule is an antibody.

A "biomarker" is a molecule of interest that is to be detected and/or analyzed, e.g., a peptide, or a protein. Typically a biomarker is associated with a particular physical condition, e.g., a disease or disease state, e.g., late stage breast cancer.

A biomarker that "binds" to a capture molecule is a term well understood in the art, and methods to determine such specific or preferential binding are also well known in the art. A molecule is said to exhibit "binding" if it reacts or associates more frequently, more rapidly, with greater duration and/or with greater affinity with a particular target than it does with alternative substances. A capture molecule "binds" to a target if it attaches with greater affinity, avidity, more readily, and/or with greater duration than it attaches to other substances. For example, a capture molecule that specifically or preferentially binds to a target is an antibody that binds this target with greater affinity, avidity, more readily, and/or with greater duration than it binds to other substances. It is also understood by reading this definition that, for example, a capture molecule that specifically or preferentially binds to a first target may or may not specifically or preferentially bind to a second target. As such, "binding" does not necessarily require (although it can include) exclusive binding. Generally, but not necessarily, reference to "binding" means preferential binding. The concept of "binding" also is understood by those of skill in the art to include the concept of specificity. Specific binding can be biochemically characterized as being saturable, and binding for specific binding sites can be biochemically shown to be competed.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule.

The terms "polypeptide," "oligopeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

An "array" format is a known or predetermined and ordered spatial arrangement of one or more capture molecules on a solid support. A "multiplexed array" format is an ordered spatial arrangement of two or more capture molecules on a solid support. In one embodiment, row and column arrangements are used due to the relative simplicity in making and assessing such arrangements. The spatial arrangement can, however, be essentially any form selected by the user, and preferably, but need not be, in a pattern. Array formats are characterized by the use of spatial location within the array to identify the feature present at that location.

"Detect" refers to identifying the presence, absence and/or amount of protein to be detected. Detection can be done visually or using a device, e.g., a scanner and detector.

The term "mammal" as used herein includes both humans and non-humans and include but is not limited to humans, non-human primates, canines, felines, murines, bovines, equines, and porcines.

"Solid support" refers to a material or group of materials having a rigid or semi-rigid surface or surfaces. In some aspects, at least one surface of the solid support will be substantially flat, although in some aspects it can be desirable to physically separate regions for different molecules with, for example, wells, raised regions, pins, etched trenches, or the like.

To "analyze" includes determining a set of values associated with a sample by measurement of constituent expression levels in the sample and comparing the levels against constituent levels in a sample or set of samples from the same subject or other subject(s).

A "predictive model" is a mathematical construct developed using an algorithm or algorithms for grouping sets of data to allow discrimination of the grouped data. As will be apparent to one of ordinary skill in the art, a predictive model can be developed using e.g., principal component analysis (PCA), and linear discriminant analysis (LDA).

A "score" is a value or set of values selected or used to discriminate a subject's condition based on, for example, a measured amount of sample constituent from the subject.

The term percent "identity," in the context of two or more nucleic acid or polypeptide sequences, refers to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information, most conveniently at its website.

Abbreviations used include: human estrogen receptor-2 (Her-2), matrix metallopeptidase-2 (MMP-2), cancer antigen 15-3 (CA 15-3), osteopontin (OPN), tumor protein 53 (p53), vascular endothelial growth factor (VEGF), cancer antigen 125 (CA 125), Serum Estrogen Receptor (SER)

It must be noted that, as used in the specification and the appended claims, the singular forms "a," "an" and "the" include plural referents unless the context clearly dictates otherwise.

Devices of the Invention

The invention provides a POC, multiplexed, channel flow-based immunoassay detection device as shown in FIG. 1. The device is comprised of a solid support, a cover plate, a vertical support, and an absorbent material. The solid support has an array of capture molecules, e.g., antibodies specific for set of biomarkers, immobilized on its upper surface. One or more flow channels are formed by coupling the upper surface of the solid support to the lower surface of the cover plate with the vertical support. Coupling is performed using, e.g., an adhesive. When coupled with the vertical support, the device has an open end for administration of a fluid mixture and a closed end opposite of the open end that is closed with the absorbent material. The flow channel is designed in a manner that allows for flow of the fluid mixture over the immobilized array of capture molecules and that is preferably driven by capillary action, although in certain embodiments involving relatively larger sample volumes, bulk flow forces may operate the device.

The fluid mixture is typically a sample, e.g., a blood sample that includes the biomarkers of interest. Often the fluid mixture includes additional reagents, e.g., detection antibodies, for detection of the biomarkers bound to the capture molecules immobilized on the solid support. The detection antibodies can be labeled for detection, e.g., fluorescently labeled.

In use, the fluid mixture is added to the open end of the device. This fluid is drawn into the channel and over the immobilized array by force preferably produced by capillary action. The fluid is then wicked from the opposite end of the channel by the absorbent material. Flow through the flow channel is unidirectional due to the absorbent material. Protein biomarkers in the fluid mixture that are bound by the capture molecules are quantified, e.g., by an optical reader that detects the fluorescently labeled detection antibodies bound to the biomarkers bound to the capture molecules immobilized to the array. The fluorescence of the array is proportional to the biomarker concentration in the fluid mixture.

Solid Support

The device includes a solid support comprising immobilized capture molecules, e.g., antibodies. Solid supports suitable for immobilizing, binding and/or linking antibodies (and modifications to render solid supports suitable for immobilizing capture molecules) are well known in the art. Examples of a solid support include: a microwell plate and a protein microarray (e.g., technology owned by Zyomyx, Inc. See, e.g. U.S. Pat. No. 6,365,418). In addition, pads, film, nanowells, or microfluid channels can also serve as a solid support. In some embodiments, the capture molecules are immobilized, bound, or linked on a solid support surface such as polyvinylidene difluoride, nitrocellulose, agarose, and/or polyacrylamide gel pads. In other embodiments, the solid support can be made of glass or include a glass slide. Glass slides activated with aldehyde, polylysine, or a homofunctional cross-linker can also been used. In yet other embodiments, the capture molecules can be arranged in a three-dimensional array, for example in the three dimensional polyacrylamide gel pad microarray described in Mirzabekov et al., Nucleic Acids Res 24(15): 2998-3004 (1996).

The invention provides a solid support, wherein capture molecules are immobilized. For the purposes of the invention, the term "immobilized" includes immobilized, bound, or linked to the solid support. Linking can be covalent or non-covalent. Methods of linking capture molecules to the solid support are well known in the art. See, e.g. Kennedy et al. (Clin. Chim. Acta 70:1-31 (1976)), and Schurs et al. (Clin. Chim. Acta 81:1-40 (1977)) (describing coupling techniques, including the glutaraldehyde method, the periodate method, the dimaleimide method, the m-maleimidobenzyl-N-hydroxy-succinimide ester method, all of which methods are incorporated by reference herein).

The capture molecules can be bound to many different solid support materials. Examples of well-known materials include polypropylene, polystyrene, polyethylene, polymers, dextran, nylon, amylases, glass, natural and modified celluloses, polyacrylamides, agaroses, silicone, and magnetite. Other materials are well known in the art. See, e.g., Angenendra et al., Next generation of protein microarray support materials: Evaluation for protein and antibody microarray applications; *Journal of Chromatography A*; Volume 1009, Issues 1-2, 15 Aug. 2003, Pages 97-104.

Preferably, the capture molecules are arranged on the solid support in an array format. More preferably, the capture molecules are arranged on the solid support in a multiplex array format. Alternatively, the capture molecules can be arranged on the solid support in ordered, sequential lines. Capture molecules and detection agents, including suitable labels, are further described herein.

Capture Molecules

The invention further provides a plurality or set of capture molecules, wherein the set comprise at least about 2 distinct capture molecules, wherein each distinct capture molecule recognizes a different biomarker, e.g., peptide or target. In some embodiments, the set comprises at least about 3, 4, 5, 6, 7, 8, or more distinct capture molecules.

A capture molecule can encompass monoclonal antibodies, polyclonal antibodies, antibody fragments (e.g., Fab, Fab', F(ab')$_2$, Fv, Fc, etc.), chimeric antibodies, single chain Fvs (ScFvs), mutants thereof, fusion proteins comprising an antibody portion, and any other polypeptide that comprises an antigen recognition site of the required specificity (including antibody mimetics. See, e.g., Xu et al, Chem Biol. 2002 Aug. 9(8):933-42). The antibodies can be murine, rat, rabbit, chicken, human, or any other origin, including humanized antibodies. Capture molecules, such as antibodies, can be made recombinantly and expressed using any method now known or later discovered in the art. In addition, antibodies can be made recombinantly by phage display technology. For examples of these expression and production methods see e.g., U.S. Pat. Nos. 5,565,332; 5,580,717; 5,733,743 and 6,265,150; and Winter et al., Annu Rev. Immunol. 12:433-455 (1994).

As used herein, the term "antibody" encompasses not only intact polyclonal or monoclonal antibodies, but also fragments thereof (such as Fab, Fab', F(ab')$_2$, Fv), single chain (ScFv), mutants thereof, fusion proteins comprising an antibody portion, and any other modified configuration of the immunoglobulin molecule that comprises an antigen recognition site of the required specificity. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these can be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

"Fv" is an antibody fragment that contains a complete antigen-recognition and -binding site. In a two-chain Fv species, this region consists of a dimer of one heavy and one light chain variable domain in tight, non-covalent association. In a single-chain Fv species, one heavy and one light chain variable domain can be covalently linked by a flexible polypeptide linker such that the light and heavy chains can associate in a dimeric structure analogous to that in a two-chain Fv species. It is in this configuration that the three complementarity determining regions (CDRs) of each variable domain interact to define an antigen-binding specificity on the surface of the VH-VL dimer. However, even a single variable domain (or half of a Fv comprising only 3 CDRs specific for an antigen) has the ability to recognize and bind antigen, although generally at a lower affinity than the entire binding site.

A "monoclonal antibody" refers to a homogeneous antibody population wherein the monoclonal antibody is comprised of amino acids (naturally occurring and non-naturally occurring) that are involved in the selective binding of an antigen. A population of monoclonal antibodies (as opposed to polyclonal antibodies) are highly specific, in the sense that they are directed against a single antigenic site. The term "monoclonal antibody" encompasses not only intact monoclonal antibodies and full-length monoclonal antibodies, but also fragments thereof (such as Fab, Fab', F(ab')$_2$, Fv), single chain (ScFv), mutants thereof, fusion proteins comprising an antibody portion, and any other modified configuration of the immunoglobulin molecule that comprises an antigen recognition site of the required specificity and the ability to bind to an antigen (see definition of antibody). It is not intended to be limited as regards to the source of the antibody or the manner in which it is made (e.g., by hybridoma, phage selection, recombinant expression, transgenic animals, etc.).

Capture molecules can be blocked using blocking agents such as, e.g., serum or serum diluted in phosphate buffered saline (PBS) and other blocking agents known in the art.

The choice of capture molecules depends on the application and the biomarkers to be detected in the sample. In one embodiment, the biomarkers to be detected are associated with breast cancer and include, e.g., include Her-2, MMP-2, CA 15-3, OPN, p53, VEGF, CA 125, and Serum Estrogen Receptor (SER). These biomarkers can include known fragments, splice variants, and full length peptides as well as other variations that are not currently known. Examples of sequence identifiers as of Feb. 11, 2008 at the HUGO on-line database for these markers include, but are not limited to, Her-2 (X03363), MMP-2 (NM_004530), OPN (NM_001040058), p53 (NM_000546), VEGF (MGC70609), CA 125 (Q8WX17), SER (NP 000116.2), and CA 15-3 (NM_002456). Additional sets of biomarkers can be chosen for other diseases including prostate cancer, ovarian cancer, and heart disease. Biomarker targets for prostate cancer can include prostate specific antigen (PSA). Biomarker targets for ovarian cancer can include CA 125. Biomarker targets for heart disease can include Troponin T, Troponin I, C-reactive protein (CRP), Homocysteine, Myoblobin, and Creatine kinase. In addition, capture molecules specific for biomarker associated with respiratory diseases can be chosen, including biomarkers associated with influenza A, influenza B, Anthrax, Plague, and allergens.

In one embodiment, the capture molecules are capture antibodies specific for breast cancer markers. Capture antibodies specific for breast cancer markers can include: 1) anti-Her-2 (R&D systems; Monoclonal Anti-human ErbB2 Antibody; MAB-1129; Clone 191924), 2) anti-Matrix metallopeptidase (MMP)-2 (R&D systems; Monoclonal Anti-human MMP-2 Antibody; MAB-902; Clone 36006.211), 3) anti-CA 15-3 (Fitzgerald; Monoclonal Anti-human CA 15-3 Antibody; 10-C03; Clone M8071022), 4) anti-Osteopontin (OPN) (R & D Systems; Monoclonal Anti-human Osteopontin Antibody; MAB-1433; Clone 190312), and 5) anti-Vascular Endothelial Growth Factor (VEGF) (Biosource; VEGF purified mouse anti-human; AHG011; Clone A183C-13G8).

As described herein, a capture molecule can bind a peptide epitope of 2 or more consecutive (i.e., sequential) amino acids. It is understood that the amino acid(s) forming the target epitope can be linear or branched, and can comprise an amino acid(s) that has been modified naturally or by intervention; for example, disulfide bond formation, glycosylation, lipidation, acetylation, phosphorylation, or any other manipulation or modification, such as conjugation with a labeling component. The amino acid(s) forming the target epitope can further encompass, for example, one or more analogs of an amino acid (including, for example, unnatural amino acids, etc.), as well as other modifications known in the art. In some embodiments the target is a protein biomarker. Protein biomarkers are further described herein.

In some embodiments, the capture molecule binds its cognate target epitope with an affinity of binding reaction of at least about $10^{-7}$ M, at least $10^{-8}$ M, or at least about $10^{-9}$ M, or tighter. In some embodiments, a binding interaction will discriminate over adventitious binding interactions in the reaction by at least two-fold, at least five-fold, at least 10- to at least 100-fold or more.

It is understood that other target binding agents can be used, in addition to the capture molecule sets described herein. In addition, it is evident that the number of capture molecules in the capture molecule set depends on the contemplated uses and applications of the set, complexity of the sample, average size of the proteins in the sample, frequency that the cognate target epitope is present or predicted to be present in a sample, binding affinity and/or specificity of the capture molecules, knowledge of target protein(s), and stability of the capture molecules. Such factors, and others, are well known in the art.

Detection of Biomarkers

Detection of target, e.g., biomarker, binding to a capture molecule can be made using detection molecules and detection agents. In one embodiment, detection molecules are detection antibodies. Detection antibodies are specific for a biomarker target, similar to capture antibodies or capture molecules.

Detection agents can be labeled using methods well-known to one of skill in the art, e.g., detection agents can be fluorescent agents, colorimetric agents, and magnetic agents. Fluorescent agents can include e.g., quantum dots and fluorophores, e.g., ALEXA 546.

In one embodiment, the detection antibodies include: 1) anti-Her-2 (R & D Systems; Polyclonal Goat Anti-human ErbB2 Antibody; AF-1129), 2) anti-MMP-2 (R & D Systems; Polyclonal Goat Anti-human MMP-2 Antibody; AF-902), 3) anti-CA 15-3 (Fitzgerald; Monoclonal Anti-human CA 15-3 antibody; 10-C03B; Clone M8071021), 4) anti-Osteopontin (R & D Systems; Polyclonal Goat Anti-human Osteopontin Antibody; AF-1433), and 5) anti-VEGF (Biosource; Polyclonal Rabbit Anti-human VEGF Biotin Conjugated Antibody; AHG9119).

Cover Plates

The device includes a cover plate coupled to the upper surface of the solid support via vertical supports. The cover plate provides an upper surface of the channel through which fluid flows. In some embodiments, the cover plate is positioned a fixed distance above the solid support for allowing the entrance of fluids into a channel formed by the coupling. The cover plate can be made of any material suitable for the application, e.g., polypropylene, polystyrene, polyethylene, polymers, dextran, nylon, plastic, amylase, silicone, glass, natural and modified celluloses, polyacrylamides, agaroses, and magnetite. In one embodiment, the cover plates are made of a hydrophilic material. In another embodiment, the cover plates are made of an optically transparent material.

In another embodiment, the cover plate is a cover slip made of glass. In another embodiment, the cover plate is a Corning® cover glass rectangle, Cat #2935-244 size 24 mm (W)× 40 mm (H)×0.13 mm (Thick).

Vertical Supports

The cover plate is connected to the solid support using a vertical support. The vertical support can be singular or, the device can include a plurality of vertical supports. The vertical support can be curved or bent to facilitate connection with the solid support. The vertical support can be arranged on the solid support to surround or outline the plurality of capture molecules immobilized on the solid support. The vertical supports can be made of e.g., polypropylene, polystyrene, polyethylene, polymers, dextran, nylon, amylase, silicone, glass, natural and modified celluloses, polyacrylamides, agaroses, and magnetite.

In one embodiment, the vertical support includes an adhesive. The adhesive can be positioned on the solid support. After the vertical supports are placed on the adhesive on the solid support another adhesive can be applied to the upper edges of the vertical supports. The cover plate can then be placed upon the vertical supports. The vertical supports inhibit the cover plate from contacting the solid support. In this manner, a channel can be formed between the solid support and the cover plate which allows fluid to pass into the channel.

The channel or channels formed by the solid support, vertical support, and cover plate can be round, trapezoidal, triangular or other geometric shapes as required. Channel sizes are optimally determined by the application. Channels can be from 0.01 mm to several millimeters deep and from 0.01 mm to several millimeters wide. Channels can be straight, curved, zig-zag, or U-shaped depending upon the application and specific function of the channel. Channels can be from 0.05 mm to several millimeters deep and from 0.1 to a centimeter or more in diameter. Capacity of the channels can range from nanoliters to 1 mL or more depending upon the application. In another embodiment, the vertical supports are SA2260, (Grace Biolabs); 1.5 mm (Wide)×1 mm (Thick)×65 mm (Long). In a related embodiment, the top adhesive layer of the SA2260 is removed and the two sides are cut out from the product and used separately.

Absorbent Material

The device comprises an absorbent material at one end of the channel or channels. The absorbent material comprises a material pervious to the passage of fluid and is absorbent. Absorbent materials can include e.g., plastics, polymers, acrylics, nylon, paper, cellulose, nitrocellulose, and ceramics. Other examples of absorbent materials include membranes available from the Pall Corporation (East Hills, N.Y.). The absorbent material may or may not comprise pores. In one embodiment, the absorbent material has pores. The pore sizes (cross-sectional dimension) of the absorbent material can range between and including about 1 nanometer to about 1 centimeter. Pore size can be adjusted according to the properties of the sample and to control the rate of fluid movement or flow over the solid support. Preferably, the absorbent material provides for wicking (i.e., drawing in of fluid by capillary action or capillarity) of the fluid into the the absorbent material. In order to promote wicking of the fluid into the absorbent material, the absorbent material can also comprise a hydrophilic material, which can be provided, for example, by the absorbent material itself with or without post treating (e.g., plasma surface treatment such as hypercleaning, etching or micro-roughening, plasma surface modification of the molecular structure, surface chemical activation or crosslinking), or by a coating provided thereto, such as a surfactant. In another embodiment, the absorbent material used in a device of the invention results in a linear flow rate on the order of approximately 1 centimeter/minute. Additionally, flow rates can be adjusted (i.e., increased or decreased) by adding or subtracting material from the absorbent material.

In another embodiment, the absorbent material is Hi-Flow Plus Nitrocellulose Membrane HF240 (Millipore; Billerica, Mass.).

Detection of Biomarker Bound to the Capture Molecules

In another embodiment, the device comprises a detection component for detecting the biomarker bound to the solid support via the capture molecules. The detection component can include a reader and a screen for displaying output from the reader. The reader can be optical. One embodiment of a detection component of the invention is the ScanArray™ 5000 XL (PerkinElmer, Inc.; Wellesley, Mass.). This is a benchtop, laser-based confocal scanning device with a photomultiplier tube (PMT) for sensitive fluorescence detection. Images collected onto a computer can be analyzed by QuantArray™ software. Raw intensities for each spot can then be computed by taking the average of the logarithm of the intensity over all pixels in the region of interest that were greater than zero for quadruplicate spots on a slide and across duplicate chambers.

Figure 2:
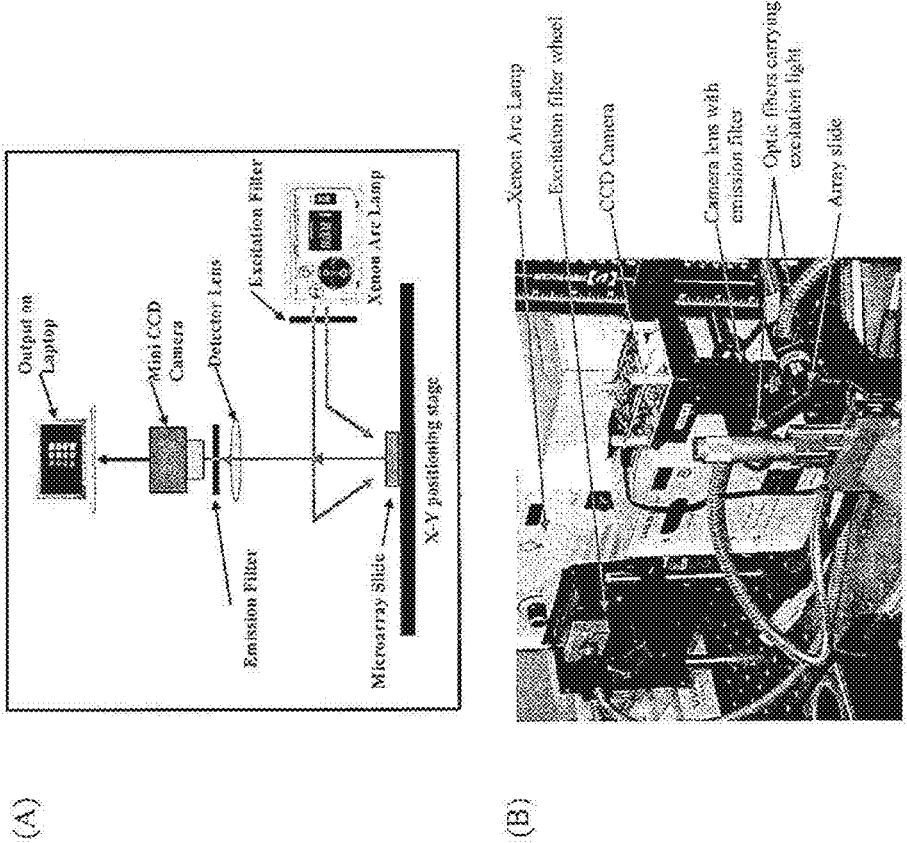
FIG. 2 is a schematic of the benchtop imaging system.

Another embodiment of a detection component of the invention is a imaging system that comprises a charge coupled device (CCD) camera. The arrangement of this imaging system is shown in FIG. 2 and it consists of a scientific-grade 16-bit, 1392×1040 pixel CCD camera (Lumenera Corp. MA), which is configured for Köhler epi-illumination of the sample microarray. The imaging system allows the sample to be illuminated from the front, while simultaneously being imaged from the same side by the CCD camera. Excitation light from a full-field White Lite® light 300 W xenon arc lamp can be bandpass-filtered using a 525 nm excitation filter (Omega Optical Inc, VT) and focused uniformly on a sample using a set of two optic fiber cables (mellesgriot) held at an angle of 45 degrees. The spots can be focused onto the CCD using a camera lens (Infinimite® alpha, Edmund Optics) and filtered using a 600 nm longpass filter. Custom algorithms, built within the Lumenera camera software correct for CCD dark noise. Images saved in tiff format can be analyzed using the Scanarray Express™ software (Perkin Elmer, Wellesley, Mass.). Output from the imaging system can be displayed on a computer screen or other viewing apparatus, including e.g., a liquid crystal display (LCD) device.

Arrays of the Invention

As describe herein, the device of the invention includes an array comprising a solid support, e.g., a glass slide and a plurality of capture molecules immobilized on the solid support. In one aspect, the invention provides an array comprising a plurality of capture molecules specific for biomarkers associated with breast cancer. The biomarkers can include, e.g., Her-2, MMP-2, CA 15-3, OPN, p53, VEGF, CA 125, and Serum Estrogen Receptor (SER). In one embodiment, the array includes capture molecules specific for CA-15-3 and OPN; in another embodiment the array includes capture molecules specific for Her-2, MMP-2, CA 15-3, and OPN.

In a related aspect, the plurality of capture molecules are a plurality of capture antibodies. The plurality of capture antibodies can include at least two of the following capture antibodies: 1) anti-Her-2 (R&D systems; Monoclonal Anti-human ErbB2 Antibody; MAB-1129; Clone 191924), 2) anti-MMP-2 (R&D systems; Monoclonal Anti-human MMP-2 Antibody; MAB-902; Clone 36006.211), 3) anti-CA 15-3 (Fitzgerald; Monoclonal Anti-human CA 15-3 Antibody; 10-C03; Clone M8071022), 4) anti-Osteopontin (R & D Systems; Monoclonal Anti-human Osteopontin Antibody; MAB-1433; Clone 190312), and 5) anti-VEGF (Biosource; VEGF purified mouse anti-human; AHG011; Clone A183C-13G8). In one embodiment, the array includes 1) anti-Her-2 (R&D systems; Monoclonal Anti-human ErbB2 Antibody; MAB-1129; Clone 191924), 2) anti-MMP-2 (R&D systems; Monoclonal Anti-human MMP-2 Antibody; MAB-902; Clone 36006.211), 3) anti-CA 15-3 (Fitzgerald; Monoclonal Anti-human CA 15-3 Antibody; 10-C03; Clone M8071022), 4) anti-Osteopontin (R & D Systems; Monoclonal Anti-human Osteopontin Antibody; MAB-1433; Clone 190312).

Methods for Categorizing a Sample

In one embodiment, the invention provides a method for scoring a sample from a subject, e.g., categorizing a human sample using quantitative data associated with a plurality of biomarkers wherein the biomarkers are associated with breast cancer.

Samples

A sample can be derived from any subject of interest, including mammalian subjects and, e.g., human subjects, e.g., patients. A sample can include blood and other liquid samples of biological origin, solid tissue samples such as a biopsy specimen or tissue cultures or cells derived therefrom, and the progeny thereof. A sample can be of cancerous origin, e.g., breast cancer. A sample can comprise a single cell or more than a single cell. Samples can also have been manipulated in any way after their procurement, such as by treatment with reagents, solubilization, or enrichment for certain components, such as proteins or polynucleotides. Sample also encompasses a clinical sample, and also includes cells in culture, cell supernatants, and cell lysates.

Quantitative Data

A "dataset" of "quantitative data" is a set of numerical values resulting from evaluation of a sample (or population of samples) under a desired condition. In one embodiment, the quantitative data is protein concentration data. The values of the protein concentration data can be obtained, for example, by experimentally obtaining measures from a sample and constructing a dataset from the measurements. In another embodiment, the protein concentration data is obtained using an enzyme linked immunosorbent assay (ELISA) format. In another embodiment, the protein concentration data is obtained using a sandwich immunoassay format. In a related embodiment, the protein concentration data is obtained using methods described herein, including sandwich immunoassay formats, and the following antibodies: Capture antibodies 1) anti-Her-2 (R&D systems; Monoclonal Anti-human ErbB2 Antibody; MAB-1129; Clone 191924), 2) anti-MMP-2 (R&D systems; Monoclonal Anti-human MMP-2 Antibody; MAB-902; Clone 36006.211), 3) anti-CA 15-3 (Fitzgerald; Monoclonal Anti-human CA 15-3 Antibody; 10-C03; Clone M8071022), 4) anti-Osteopontin (R & D Systems; Monoclonal Anti-human Osteopontin Antibody; MAB-1433; Clone 190312), and 5) anti-VEGF (Biosource; VEGF purified mouse anti-human; AHG011; Clone A 183C-13G8); Detection antibodies 1) anti-Her-2 (R & D Systems; Polyclonal Goat Anti-human ErbB2 Antibody; AF-1129), 2) anti-MMP-2 (R & D Systems; Polyclonal Goat Anti-human MMP-2 Antibody; AF-902), 3) anti-CA 15-3 (Fitzgerald; Monoclonal Anti-human CA 15-3 antibody; 10-C03B; Clone M8071021), 4) anti-Osteopontin (R & D Systems; Polyclonal Goat Anti-human Osteopontin Antibody; AF-1433), and 5) anti-VEGF (Biosource; Polyclonal Rabbit Anti-human VEGF Biotin Conjugated Antibody; AHG9119). In another embodiment, the data are obtained using a multiplexed channel flow-based device, e.g., the device described above (FIG. 1).

Alternatively, quantitative data can be obtained from a service provider such as a laboratory, or from a database or a server on which the data has been stored.

Plurality of Biomarkers

The method of categorizing sample uses data associated with a plurality of biomarkers associated with breast cancer. In one aspect, the plurality of biomarkers associated with breast cancer includes CA 15-3 and OPN. In another aspect, additional biomarkers can include Her-2. In another aspect, additional biomarkers can include MMP-2. In another aspect, additional biomarkers can include VEGF. In another aspect, additional biomarkers can include Her-2 and MMP-2. In yet another aspect, additional biomarkers can further include p53, CA 125, and Serum Estrogen Receptor (SER). In one embodiment of the invention, the method of categorizing a sample uses data associated with the following biomarkers: CA 15-3, OPN, Her-2, and MMP-2.

Scoring the Sample

In one embodiment, scoring the sample comprises analyzing the data and outputting a score. Analysis of the data can include use of a predictive model. Predictive models can be developed using, e.g., principal component analysis (PCA), and linear discriminant analysis.

PCA is a technique used to reduce multidimensional data sets to lower dimensions for analysis. Mathematically, PCA is defined as an orthogonal linear transformation that transforms the data to a new coordinate system such that the greatest variance by any projection of the data comes to lie on the first coordinate (called the first principal component), the second greatest variance on the second coordinate, and so on. PCA can be used as a tool in exploratory data analysis and for making predictive models. PCA can also involve the calculation of the eigenvalue decomposition of a data covariance matrix or singular value decomposition of a data matrix, usually after mean centering the data for each attribute. The results of a PCA are usually discussed in terms of component scores and loadings.

Linear discriminant analysis is a method used to find the linear combination of features which best separate two or more classes of objects or events. The resulting combination can be used as a linear classifier, or, alternatively, for dimensionality reduction before later classification.

In another embodiment, the analysis can include categorizing the sample according to a predictive model. The probability that categorization is correct is model- and biomarker-dependent and can be at least 60%, at least 70%, at least 80%, at least 87%, at least 90%, or at least 95% correct. Categories can include a healthy categorization, i.e. disease-free, an early-stage disease categorization, and a late-stage disease categorization.

In another embodiment, the score can be compared to a second score determined for a second sample from the mammalian subject. This comparison can be used e.g., to determine the progress of therapy for the treatment of disease. In yet another embodiment, the score can be used to diagnose a neoplastic breast disease. A neoplastic breast disease can include e.g., breast cancer.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); Remington's Pharmaceutical Sciences, 18th Edition (Easton, Pa.: Mack Publishing Company, 1990); Carey and Sundberg *Advanced Organic Chemistry* $3^{rd}$ Ed. (Plenum Press) Vols A and B(1992).

Example 1

Development of Multiplexed Assays

A multiplexed immunoassay for the measurement of breast cancer biomarkers using the protein microarray format was developed.

Protein microarrays have the potential to be used to simultaneously analyze large numbers of serum proteins in a rapid and reproducible manner. In recent years, protein microarrays have evolved as powerful tools to address high-throughput requirements by performing "traditional" biochemistry in an ultra-high-throughput and miniaturized format. On protein microarrays, purified capture molecules are immobilized in unique locations on the surface of the substrate that allow for recognizing the target under study. Since each capture molecule is immobilized in a precise, predetermined spot, the protein microarrays achieve multiplexing capability based on this unique location of the capture molecule and therefore the target protein bound to it (assuming high specificity of the antibody-antigen reaction). In the case of a reverse assay on the microarray, the immobilized molecule includes large collections of purified proteins or samples such as sera and lysates, which is then probed with a single antibody.

Materials

A multiplexed breast cancer assay based on the protein microarray was developed after validating the reagents using 2d Gel Electrophoresis and ELISA techniques. This example presents the assay development materials and methods on these platforms.

Common Reagents

Recombinant proteins, capture, and biotinylated detection antibodies for Her-2, MMP-2 and Osteopontin were purchased from R&D systems (Minneapolis, Minn.). Other reagents used in the assay include: VEGF antigen and capture and biotinylated detection antibodies (Biosource International Camarillo, Calif.), CA 15-3 antigen and anti-CA 15-3 capture and detection antibodies (Fitzgerald, Concord, Mass.). The CA 15-3 detection antibody was biotinylated using a kit and according to the manufacturer's (Pierce, Rockford, Ill.) instructions. All other detection antibodies were purchased as biotin conjugates. Lyophilized human serum was purchased from Rockland Immunochemicals (Gilbertsville, Pa.). Capture antibodies used were: 1) Her-2 (R&D systems; Monoclonal Anti-human ErbB2 Antibody; MAB-1129; Clone 191924), 2) MMP-2 (R&D systems; Monoclonal Anti-human MMP-2 Antibody; MAB-902; Clone 36006.211), 3) CA 15-3 (Fitzgerald; Monoclonal Anti-human CA 15-3 Antibody; 10-C03; Clone M8071022), 4) Osteopontin (R & D Systems; Monoclonal Anti-human Osteopontin Antibody; MAB-1433; Clone 190312), and 5) VEGF (Biosource; VEGF purified mouse anti-human; AHG011; Clone A183C-13G8). Detection antibodies used were: 1) Her-2 (R & D Systems; Polyclonal Goat Anti-human ErbB2 Antibody; AF-1129), 2) MMP-2 (R & D Systems; Polyclonal Goat Anti-human MMP-2 Antibody; AF-902), 3) CA 15-3 (Fitzgerald; Monoclonal Anti-human CA 15-3 antibody; 10-C03B; Clone M8071021), 4) Osteopontin (R & D Systems; Polyclonal Goat Anti-human Osteopontin Antibody; AF-1433), and 5) VEGF (Biosource; Polyclonal Rabbit Anti-human VEGF Biotin Conjugated Antibody; AHG9119).

Reagents for Western Blotting

Anti-goat, anti-rabbit and anti-mouse secondary antibodies were conjugated to horseradish peroxidase (HRP) (EMD Biosciences, San Diego, Calif.). Laemmli sample buffer, precision plus dual molecular weight standard and 7.5% and 10% ready gels were purchased from BioRad Inc (Hercules, Calif.), enhanced chemiluminescence (ECL) detection kits and hyperfilm were obtained from Amersham Biosciences (Piscataway, N.J.) and PVDF transfer membrane from (Millipore, Bedford, Mass.). Tris buffered saline (TBS) and Tris buffered saline with 0.05% tween (TBS-T), was purchased from Sigma-Aldrich (St. Louis, Mo.).

Reagents for ELISA

Antibody biotinylation kit and Blotto were purchased from Pierce (Rockford, Ill.). Vectastain kit was purchased from Vector Labs (Burlingame, Calif.), Nunc ELISA 96 well plates was obtained from Nalge Nunc International, (Rochester, N.Y.) and Hanks buffer was purchased from Invitrogen-GIBCO (Carlsbad, Calif.). Phosphate buffered saline with 0.05% tween (PBS-T), Phosphate buffered saline (PBS) and TMB (3,3'.5,5'-tetramethylbenzidine) were purchased from Sigma-Aldrich (St. Louis, Mo.).

Reagents for Protein Microarrays

Streptavidin conjugated Alexa 546 was purchased from Invitrogen-Molecular Probes (Carlsbad, Calif.), GAPS II™ slides were purchased from Corning LifeSciences (Corning, N.Y.) and BSA was purchased from Sigma-Aldrich (St. Louis, Mo.).

Methods

Reagent Quality Validation Using Gel Electrophoresis and Western Blotting

Gel electrophoresis for each biomarker was performed in non-reducing conditions with 7.5% (for Her-2(185 kD) and CA 15-3(250 kD)) and 10% (for OPN (66 kD), MMP-2(72 kD) and VEGF (38 kD)) polyacrylamide gels. Samples were solubilized in Laemmli sample buffer and boiled for 3 minutes before loading into the sample wells. Approximately 150 µg of each protein was loaded into each well. Precision plus dual standard was used as the molecular weight marker. After electrophoresis for 2 h at 120V, the proteins were transferred from the gel on to the PVDF membrane under an electric field, using a fully immersed wet unit (BioRad, Hercules, Calif.), for 1 h at room temperature with ice in the unit. The membrane was then immersed in wash buffer (TBS-T) for 15 minutes and blocked overnight at 4° C., with 5% w/v milk (BioRad, Hercules, Calif.) prepared in wash buffer. Following the blocking step, the membrane was washed in TBS-T for 30 minutes and incubated with primary antibody at 500 ng/ml (Mouse and Goat anti Her-2 antibody, Mouse and Goat anti MMP-2 antibody, Mouse and Goat anti-Osteopontin antibody, Mouse and Rabbit anti-VEGF antibody and two Mouse anti-CA 15-3 antibodies) for 1 hour at room temperature. After a 30 minute wash in TBS-T, the membrane was incubated for 1 hour at room temperature with the secondary antibody conjugated to HRP (Anti-Goat, Anti-Rabbit or Anti-Mouse as applicable) at 500 ng/ml. The protein bands in the gel were finally visualized using the ECL kit and a sensitive photo film.

Selection of Antibody Pairs: Enzyme Linked Immunosorbent Assays (ELISA)

The concentrations of the capture and detector antibodies for all five biomarkers, to be used in a sandwich format, were optimized using standard two antibody sandwich ELISA. 100 µL of capture antibody solution in ELISA coating buffer (Hanks buffer, with 0.375% $NaHCO_3$) was added in duplicate to the wells of the 96-well plate in a series of four dilutions (0.1 µg/ml, 0.3 µg/ml, 1 µg/ml and 3 µg/ml). These dilutions were added across the rows of the plate. After overnight incubation at 4° C., the coating antibody solution was aspirated from the wells and the plates were rinsed 6 times in PBS-T and then blocked for 2 h at room temperature in 200 µl of BLOTTO. The solution was then aspirated from the wells, and the plate was washed 6 times in PBS-T. 100 µL of the recombinant antigen was added to the appropriate wells in dilutions representing the middle portion of the clinical range for the biomarkers. The concentrations of antigens used for this assay were 10 ng/ml for Her-2, 600 ng/ml for MMP-2, 130 U/ml for CA 15-3, 700 ng/ml for OPN, and 550 pg/ml for VEGF, respectively. Buffer without antigen was used to represent background signal. The plate was sealed and incubated at room temperature for 2 hours followed by 6 washes with PBS-T. 100 µl of biotinylated detection antibody solutions were then added down the columns of the plate in a series of four dilutions (0.36 µg/ml, 1.1 µg/ml, 3.3 µg/ml and 9.9 µg/ml). For VEGF, biotinylated antibody was used at higher concentrations of 3 µg/ml, 8 µg/ml, 25 µg/ml and 75 µg/ml according to manufacturer's (R&D systems) suggestions. Following a 1-hour incubation at room temperature, the plates were washed 6 times and 100 µl of Vectastain solution (prepared according to the manufacturer's instructions) was added for 30 minutes to probe for the detection antibodies. The plates were then washed 6 times and incubated with 100 µl of TMB for 30 minutes at room temperature. The reaction was stopped by adding 50 µL of 1N $H_2SO_4$ to each well before reading the absorbance at 485 nm in the microplate reader (BioRad, Hercules, Calif.). After color development and measurement of absorbance, the capture and detector antibody concentrations yielding the best signal to noise ratio were selected for further ELISA development.

Standard curves of each of the biomarkers were then obtained by performing the ELISA as outlined in the basic protocol above except that optimized concentrations of capture and detector antibodies were used with 8 serial dilutions of recombinant antigen standards to obtain a standard titration curve. The concentrations of biomarkers used to establish this standard curve were 1 ng/ml 128 ng/ml for Her-2, 10 ng/ml-1280 ng/ml for MMP-2, 2 U/ml-256 U/ml for CA 15-3, 10 ng/ml-1280 ng/ml for OPN and 1 pg/ml-1280 pg/ml for VEGF.

Microarray Spotting and Assay Protocol

Concentrations of capture and detector antibody pair for each of the five biomarkers were optimized for use in a sandwich assay format on the microarray similar to the ELISA optimizations. Aminosilanated, GAPS II™ barcoded glass slides were spotted with optimized dilutions of capture antibodies using a robotic arrayer (Norgen Systems Inc.; Mountain View, Calif.). Four print heads were used to deposit approximately 1 nl of capture antibody solution, generating a total of 8 arrays per slide with 250 µm diameter spots with a spot-to-spot distance of 350 µm. The layout of each 8×12 array of printed antibody spots corresponded to one spot per well in a standard 8×12 (96-well) format. These capture antibodies were printed in a series of four dilutions (1000 µg/ml, 500 µg/ml, 250 µg/ml and 125 µg/ml). Also printed on each slide were two controls. Bovine serum albumin (BSA) served as negative control (NC). Alexa 546 spots were used as position controls (PC), which served as reference points when the slides were imaged. The spotted slides were cross-linked under ultraviolet light for 5 minutes and were stored in the dark at 4° C.

The eight arrays were separated using silicone gasket chambers (Schleicher & Schuell Bioscience, Keene N.H.) and were blocked with 1 mg/ml BSA solution for 30 minutes. The protein microarrays were then washed for 15 minutes and incubated with 100 µl of target antigen at dilutions representing the middle portion of the clinically significant ranges for the biomarkers. The concentrations of antigens used for this assay were 10 ng/ml for Her-2, 600 ng/ml for MMP-2, 130 U/ml for CA 15-3, 700 ng/ml for OPN and 550 pg/ml for VEGF respectively. Buffer without any added recombinant antigen was used to determine the background due to non-specific binding on the arrays. The solution was aspirated and washed with PBS-T for 15 minutes and the wells were then incubated with 100 µl of a series of four dilutions of biotinylated antibody solution (1.8 µg/ml, 3.75 µg/ml, 7.5 µg/ml and 15 µg/ml) in PBS for 30 minutes. Following a 15 minute wash, the arrays were incubated with 100 µl streptavidin conjugated Alexa 546 for 10 minutes. The chambers were then removed and the slides were agitated in PBS-T for 10 minutes and dried by centrifugation prior to scanning Two sets of standard curves were obtained. One, using PBS as the diluting medium for the recombinant antigens and one using human serum as the medium. The protein microarray standard titration curves were obtained as outlined in the basic protocol except that serial dilutions of recombinant antigen standards in PBS and human serum were used as analytes and the optimized concentrations of capture and detector antibodies were used for detection. The concentrations of biomarkers used to establish this standard curve were 1 ng/ml-128 ng/ml for Her-2, 10 ng/ml-1280 ng/ml for MMP-2, 2 U/ml-256 U/ml for CA 15-3, 10 ng/ml-1280 ng/ml for OPN, and 1 pg/ml-1280 pg/ml for VEGF.

Microarray Spotting and Assay Protocol: Multiplex Curves

This multiplexed assay was performed essentially as described for the standard titration curves. Capture antibodies for Her-2, MMP-2, OPN, CA 15-3 and VEGF were spotted in quadruplicate at 500 µg/ml on the GAPS II™ slides to form a 4×5 array grid. Ten different multiplex samples were prepared. Five samples were prepared with a mixture of all but one antigen and five of the remaining samples contained only one antigen each. The concentrations of recombinant antigens used in this assay were 20 ng/ml Her-2, 800 ng/ml MMP-2, 130 U/ml CA 15-3, 900 ng/ml OPN and 950 pg/ml VEGF. A second set of ten slides was prepared in a similar manner, but using human serum as the medium instead of PBS. In this case, only four biomarkers were used (Her-2, MMP-2, CA 15-3 and Osteopontin). Antibody microarrays were incubated with these antigen samples in duplicate, followed by incubation with a detector antibody "cocktail" containing biotinylated antibodies for all five biomarkers at a concentration of 3.75 μg/ml. Streptavidin conjugated Alexa 546 was used as the reporter at a concentration of 5 μg/ml. The chambers were then removed and the slides were agitated in PBS-T for 10 minutes and dried by centrifugation prior to scanning Microarray Imaging and Analysis Protocol Slides were imaged with ScanArray 5000 XL (Perkin Elmer, Wellesley, Mass.), which is a laser-based confocal scanner, at 543 nm excitation. Images collected onto a PC were analyzed by Scanarray Express™ software (Perkin Elmer, Wellesley, Mass.). Raw intensities for each spot were computed by taking the average of the logarithm of the intensity over all pixels in the region of interest that were greater than zero for the spot. A median of all quadruplicate spots across 2 wells (resulting in a total of eight spots per sample) was computed and plotted against concentration for a titration curve.

Results

Western Blotting

Antigens purchased from various sources were tested for purity by performing SDS-PAGE, which demonstrated the specificities of the antibodies as well as tested the purity of the recombinant antigens. This was followed by detection with monoclonal antibodies (FIG. 3A) (to be employed as capture antibodies in the ELISA) polyclonal antibodies (FIG. 3B) (to be employed as detector antibodies in the ELISA) using Western Blotting. Approximately 150 ng of protein was loaded in each lane and the gels were run under non-reducing conditions to mimic the detection of proteins in serum. Distinct bands are observed for four of the biomarkers, MMP-2 (72 kDa), CA 15-3 (250 kDa), OPN (66 kDa) and VEGF (38 kDa). For the biomarker, Her-2 (185 kDa) distinct, multiple bands were seen due to the phosphorylated forms of the protein, all of which are recognized by the antibody.

Figure 3:
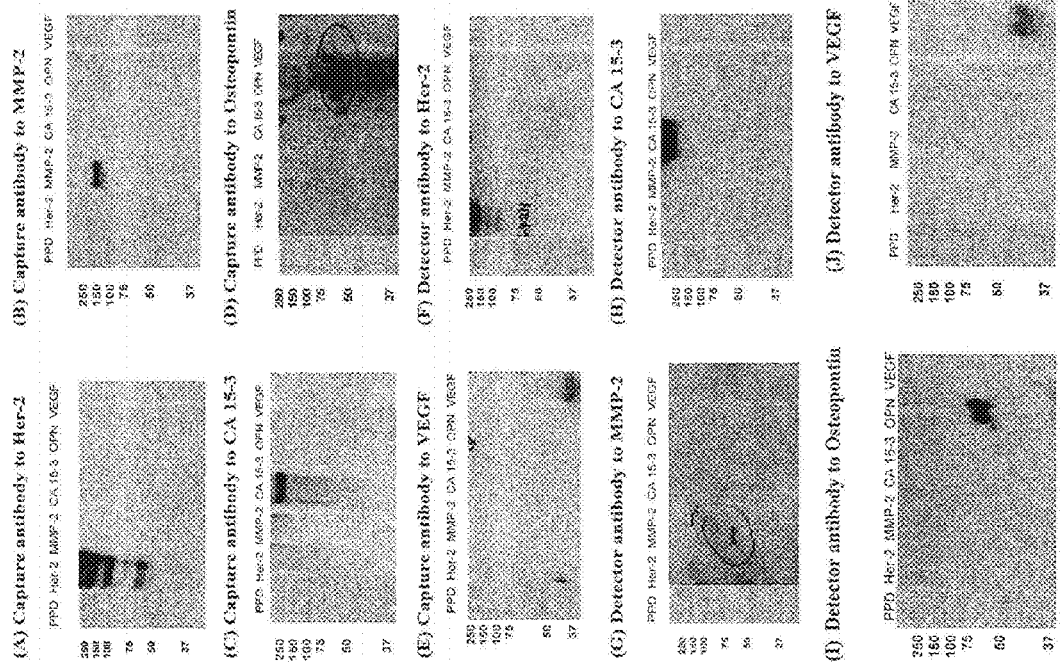
FIG. 3 shows testing for the specificity of the tested antibodies using western blotting with five antigens.

To demonstrate the specificity of these antibodies, all five recombinant protein biomarkers were run in neighboring wells in the gel, transferred them onto the PVDF membrane and incubated the membrane with one single antibody. As can be seen in FIG. 3, the capture (A-E) and detector (F-J) antibodies showed high specificity to their respective antigens. Using this method, the most specific capture (monoclonal) antibodies and detector (monoclonal and polyclonal) for all five biomarkers from a total of 30 antibody pairs and 5 recombinant antigens were selected.

ELISA

Figure 4:
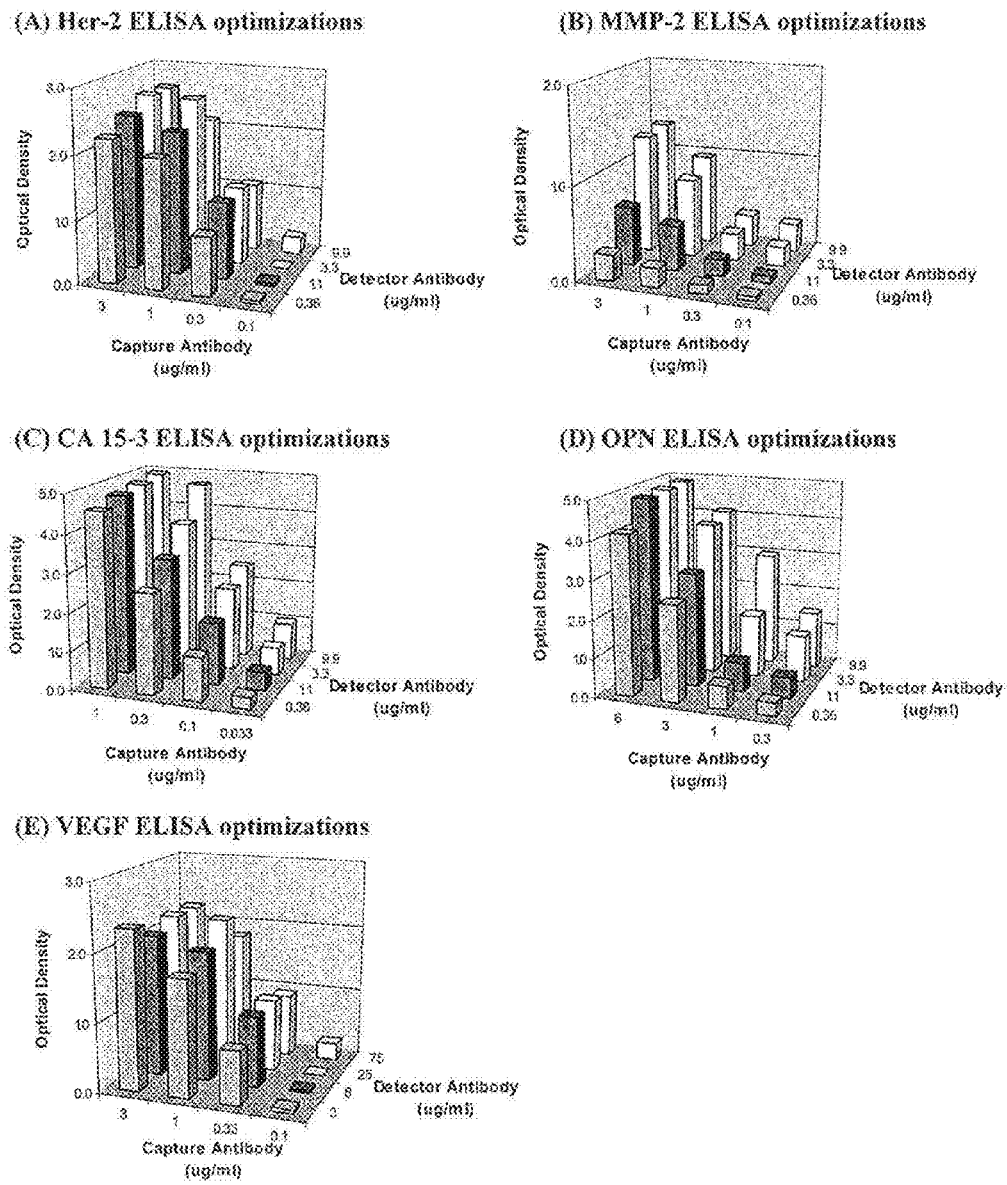
FIG. 4 shows optimization of capture and detector antibody concentrations for developing standard curves using enzyme linked immunosorbent assay (ELISA).

The selected antibodies were then characterized for dynamic range and sensitivity in the clinically-relevant concentrations (as observed in normal and breast cancer patient sera) using ELISA as the validation method. The monoclonal antibodies were used as capture and the biotinylated polyclonal antibodies were used as detector (except in the case of CA 15-3, where both antibodies were monoclonal). ELISA plates were coated with four different concentrations of the capture antibodies in the ELISA coating buffer as described in materials and methods. Two dilutions of recombinant antigen were used, one on either end of the clinically-relevant range. Sample with no antigen added was used as negative control for the assay. Biotinylated detector antibodies were then added in four different dilutions to the wells. FIG. 4 shows the results obtained from these optimizations. The concentrations of capture and detector antibodies that yielded a good signal (O.D between 1.0 and 2.0, which was neither too low nor saturated) were chosen for the assays. Since the detector antibodies were more expensive than the capture antibodies (because of their biotin-conjugation), a combination of capture and detection concentration was chosen that gave a good signal, but nevertheless used the minimum amount of detector antibody. Table 1 lists the final chosen concentrations of both the antibodies using this criterion and which were used to develop ELISA curves.

Figure 5:
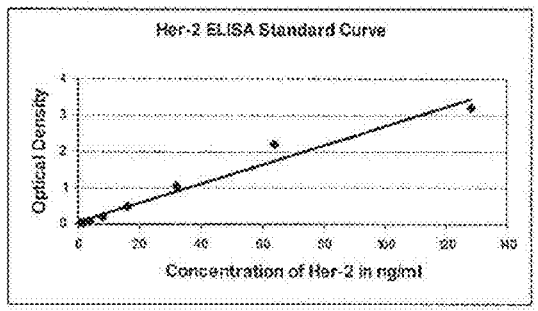
FIG. 5 are standard curves using ELISA.
Figure 5:
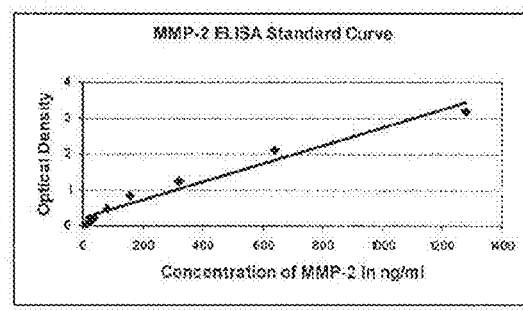
Figure 5:
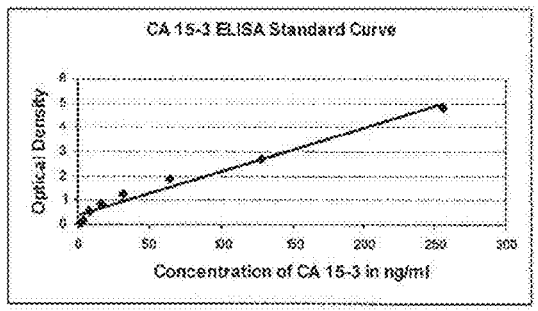
Figure 5:
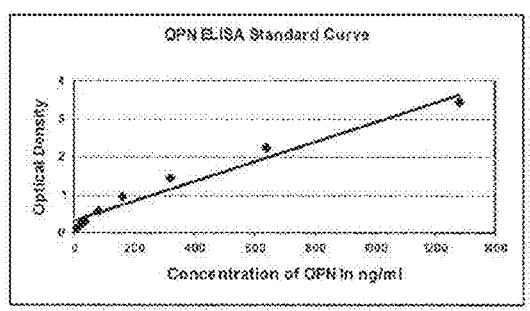
Figure 5:
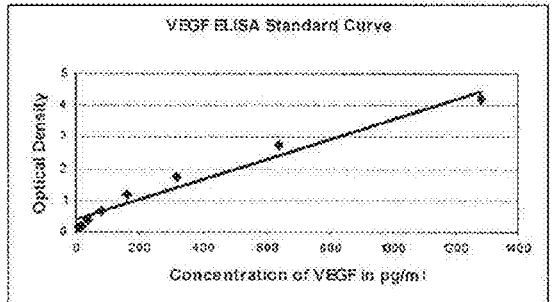

Standard curves for all five biomarkers were developed on the ELISA platform. 96 well polystyrene plates were coated with capture antibody at optimized concentration, followed by incubation with 8 serial dilutions of recombinant antigen in PBS. The concentrations of biomarkers used to establish this standard curves were 1 ng/ml-128 ng/ml for Her-2, 10 ng/ml-1280 ng/ml for MMP-2, 2 U/ml-256 U/ml for CA 15-3, 10 ng/ml-1280 ng/ml for OPN and 1 pg/ml-1280 pg/ml for VEGF. The wells were then probed with optimized concentration of biotinylated detector antibody. Enzyme based detection was used in this assay in which, wells were interrogated with a spectrophotometer to obtain intensities of substrate color. Increased color intensity was observed with increased protein concentration. These intensities are quantified and plotted as a function of antigen concentration to obtain a standard curve. FIG. 5 demonstrates that the ELISA assay curves are linear over the clinically-relevant ranges for these biomarkers and span normal as well as elevated levels as seen in cancer. Data points for each curve represent the average intensities of two replicate samples. Reproducibility was determined from the coefficient of variation, which was approximately 5% for all protein biomarker curves. The background signal, which is a measure of non-specific binding, was considered to be the signal from the wells in which no antigen was added. Each point on the ELISA curve plotted below represents the signal from the wells minus this background.

Standard Curves were Established on Protein Microarrays

Figure 6:
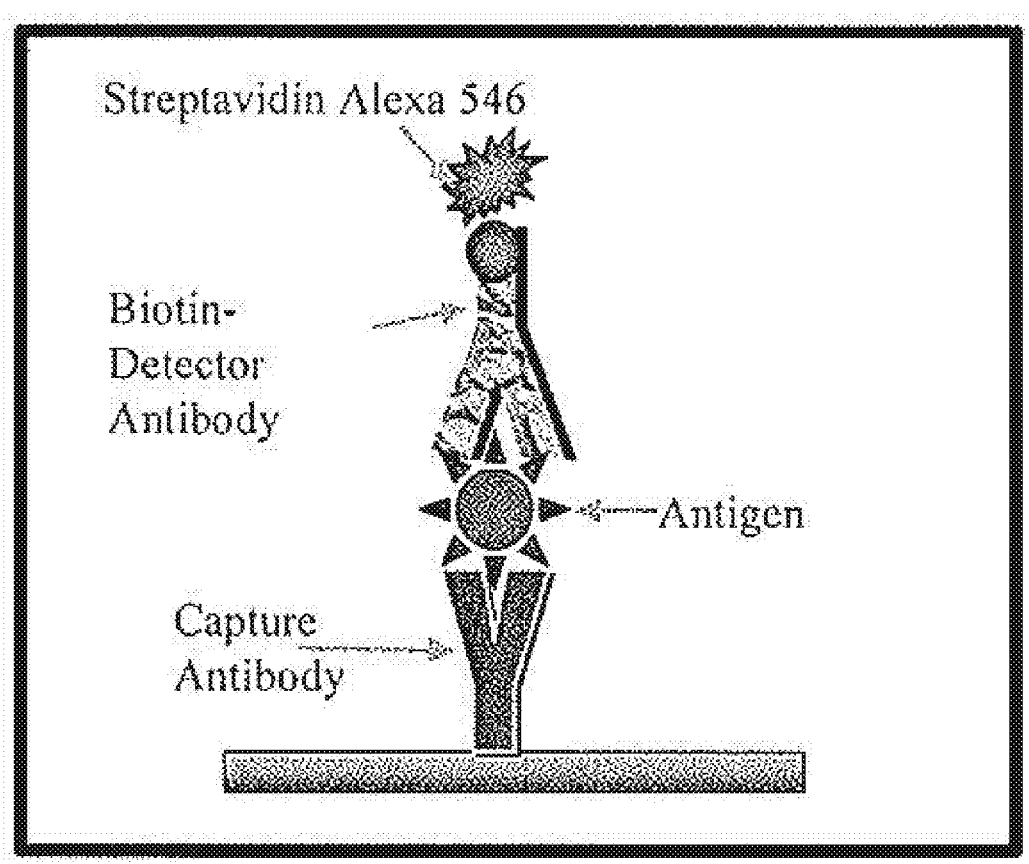
FIG. 6 is a schematic of the sandwich immunoassay format used in protein microarrays.

Western blotting was used to validate the specificity of the reagents selected and ELISA was used to characterize the performance of these antibodies in a sandwich immunoassay format. These antibody pairs were then employed on the protein microarray platform to generate standard curves in singleplex as well as multiplex format. Similar to the ELISA, concentrations of these antibodies were optimized on the protein microarray prior to establishing the standard curves. A schematic diagram of the microarray assay approach used in this study is shown in FIG. 6.

Capture antibodies immobilized on modified glass slides are probed with sample containing antigen. A second biotinylated antibody then binds to the antigen on the array and a streptavidin-linked fluorescent dye was used for detection. For the optimization studies, amine modified microarray slides were printed with four distinct dilutions of the capture antibodies in PBS buffer as described in materials and methods. The spot size was approximately 250 μm in diameter. Two dilutions of recombinant antigen were used, one on either end of the clinically-relevant range. Sample with no antigen added was used as negative control for the assay. A second, biotinylated antibody recognizing a different epitope on the same antigen was used in three different dilutions for detection. This "sandwich" approach favors specificity in analyte detection, since the two separate antibodies sequentially enable selective detection. A streptavidin-Alexa 546 fluorescent reporter was then used to bind to the biotin moiety of the detection antibody which then produced fluorescent signals proportional to the amount of antigen bound on the array.

Figure 7:
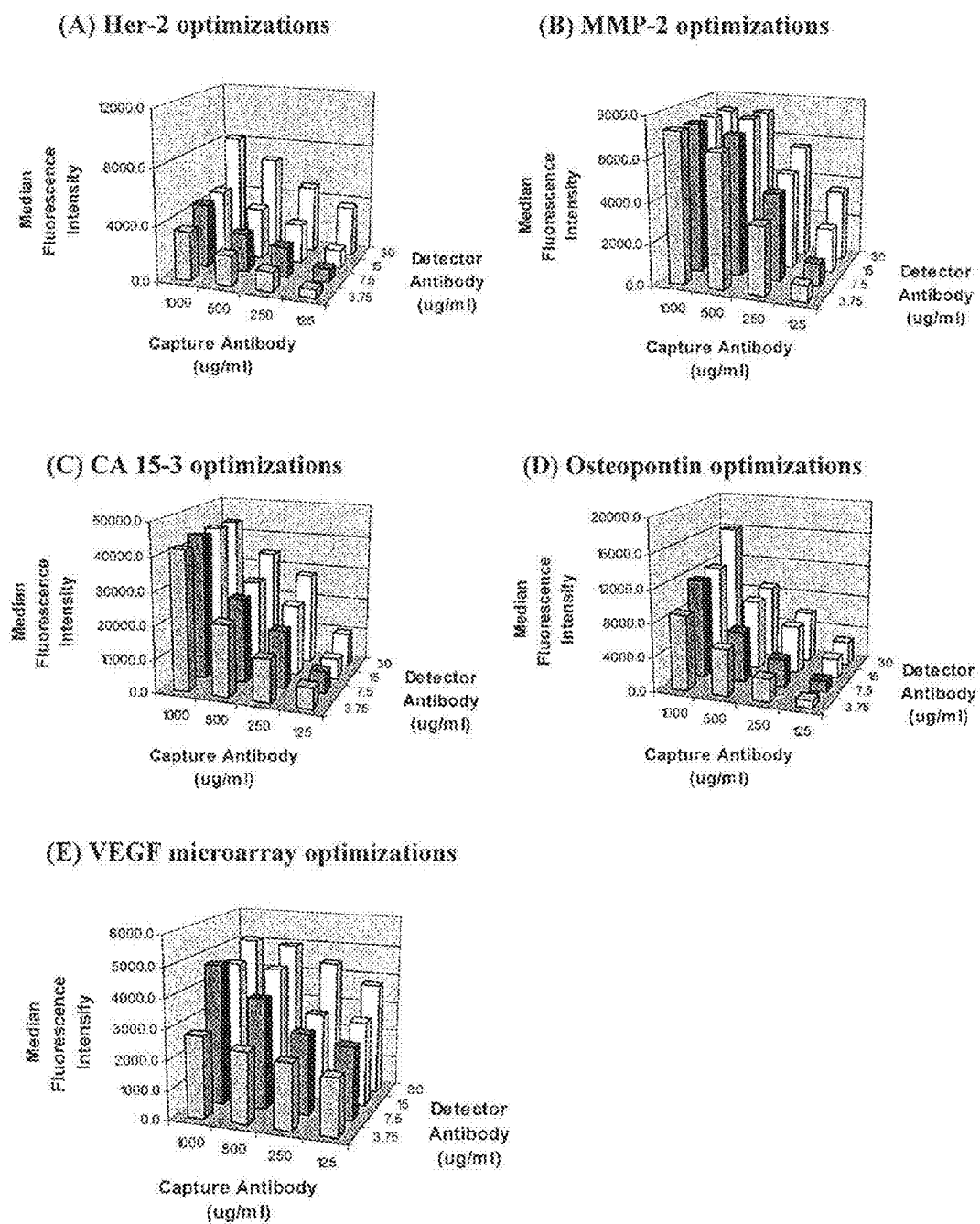
FIG. 7 shows optimization of capture and detector antibody concentrations for developing standard curves using the antibody microarray immunoassay.

These fluorescent spots were then quantified using a fluorescence microarray reader. FIG. 7 illustrates the signals obtained from these optimizations and Table 2 demonstrates the final chosen concentrations of both the antibodies that were used to develop microarray curves. Similar to the ELISA optimization experiments, the combination of capture and detector antibody that yielded maximum response with minimum amount of detector antibody was chosen as the optimized concentration.

The optimized concentrations of capture antibodies were printed on modified microarray slides using a robotic arrayer such that each antibody was present in quadruplicate. The capabilities of the microarray were further tested by analyzing single biomarkers over a range of concentrations in a multiplexed format, using all five capture and detector antibodies (see FIGS. 8 and 9). The goal here was to measure the effect of the presence of other capture agents and varying antibody affinities on the multiplexed detection of five proteins. Protein microarrays were incubated with 8 serial dilutions of recombinant antigen diluted in PBS. The concentration ranges used were 1 ng/ml-128 ng/ml for Her-2, 10 ng/ml-1280 ng/ml for MMP-2, 2 U/ml-256 U/ml for CA 15-3, 10 ng/ml-1280 ng/ml for OPN and 10 pg/ml-1280 pg/ml for VEGF. Standard curves were obtained on the protein microarray format for each biomarker in four formats. First, only one capture antibody (Singleplex format) was used and second, the all five capture antibodies were spotted on the array and all five detector antibodies were used (Multiplex format). In both cases the antigens were diluted in PBS. This method was most similar to the ELISA. The third and fourth formats are similar to the first and second, except that human serum was used as the diluting medium instead of PBS. This method enabled the quantification of effect of serum on background noise and thus simulated detection of these proteins in patient sera.

Figure 8:
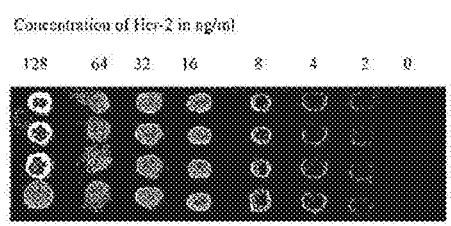
FIG. 8 is visualization of standard curves using the antibody microarrays.
Figure 8:
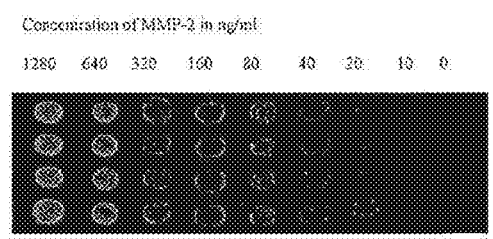
Figure 8:
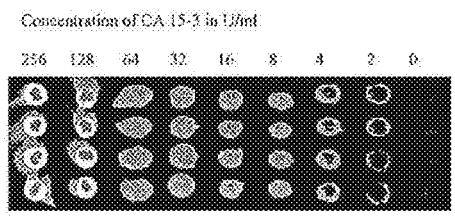
Figure 8:
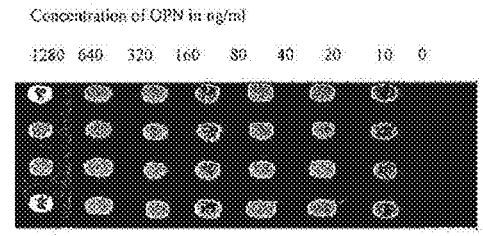
Figure 8:
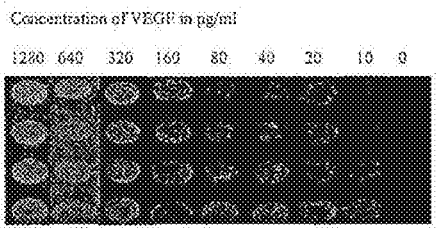

FIG. 8 shows a composite image of eight different arrays with each column representing a different array that was incubated with increasing antigen concentration from right side of the FIG. to the left side of the FIG. Slides shown in Panel A were incubated with Her-2 at concentrations ranging from 0 ng/ml (right) to 128 ng/ml (left). Slides shown in Panel B were incubated with MMP-2 with a concentration range of 0 ng/ml (right) to 1280 ng/ml (left). Slides shown in Panel C were incubated with CA 15-3 at concentrations ranging from 0 U/ml (right)-256 U/ml (left) and those shown in Panel D were incubated with Osteopontin at concentrations from 0 ng/ml (right) to 1280 ng/ml (left). Finally, Panel E shows slides incubated with VEGF in the concentration range of 0 pg/ml (right)-1280 pg/ml (left). The results show increased fluorescence intensity with increased protein concentration.

Figure 9:
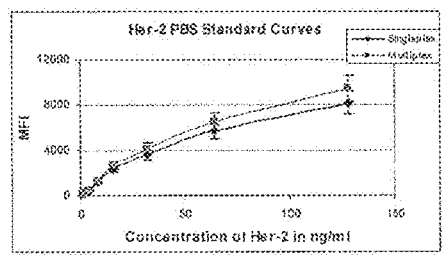
FIG. 9 is a comparison of standard curves obtained in a single plex and a multiplex format. using the antibody microarrays, with phosphate buffered saline (PBS) and Serum as the medium.
Figure 9:
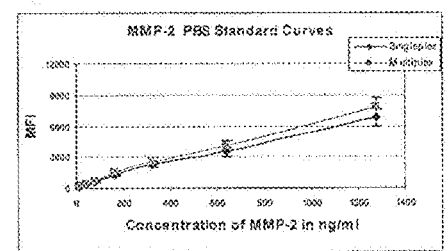
Figure 9:
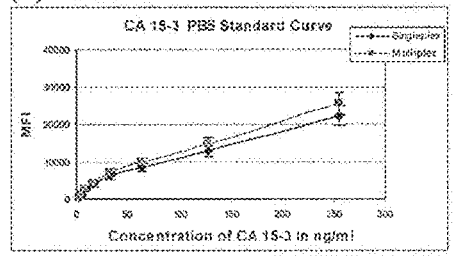
Figure 9:
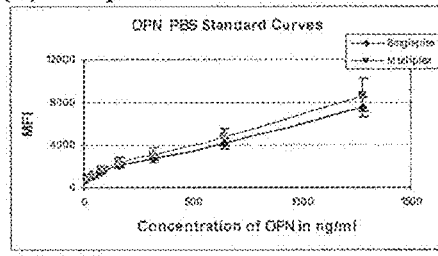
Figure 9:
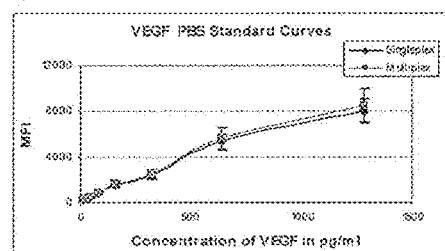
Figure 9:
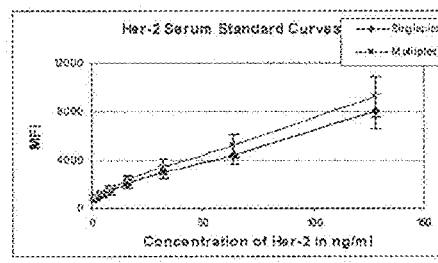
Figure 9:
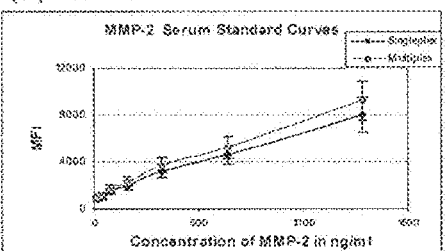
Figure 9:
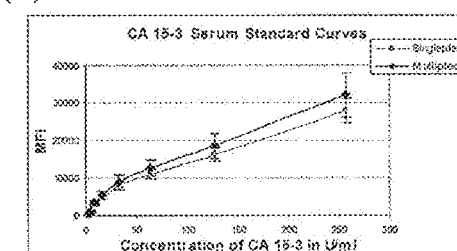
Figure 9:
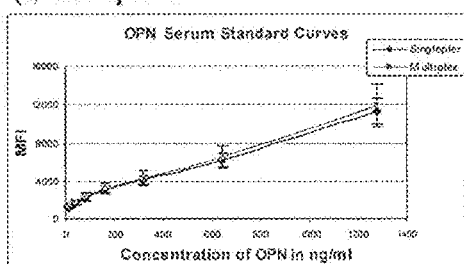
Figure 9:
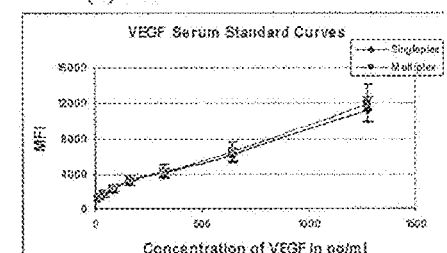

The fluorescence from these spots is quantified using the Scanarray software and plotted as a function of antigen concentration in FIG. 9 (A-E) for the experiments with PBS as the medium and in FIG. 9(F-J) for the experiments in which human serum was used as the diluent. The background signal, which is a measure of non-specific binding, was considered to be the signal from the arrays in which no antigen was added. Data points for each curve represent the average intensities of eight replicates (background subtracted) obtained using quadruplicate spots in two replicate arrays. Reproducibility was determined by the coefficient of variation, which was approximately 15% for all protein biomarker curves.

The multiplex assays have a higher background noise level than the singleplex assays probably due to the presence of additional detector antibodies in the assay. However, the shapes of the intensity curves compare well to the assays in the singleplex format validating the use of multiplex microarray assays. A higher background in the serum assays as compared to the PBS based assays was observed, likely due to the presence of other proteins in the serum that bind non-specifically to the slide.

Comparison of ELISA and Protein Microarray Formats

Figure 10:
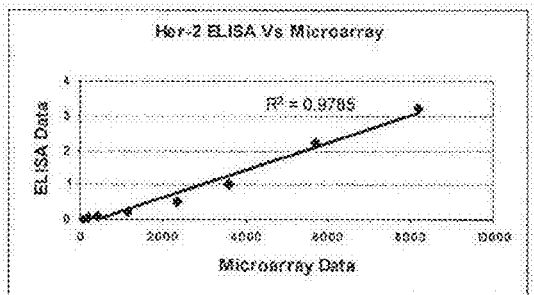
FIG. 10 is a comparison of standard curves obtained using antibody microarrays with the ELISA.
Figure 10:
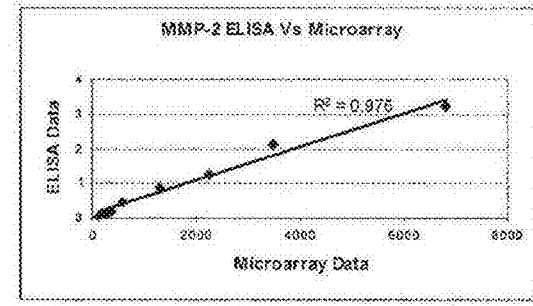
Figure 10:
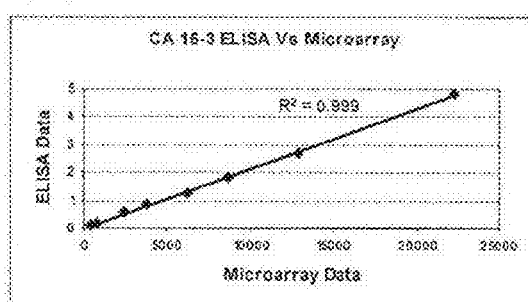
Figure 10:
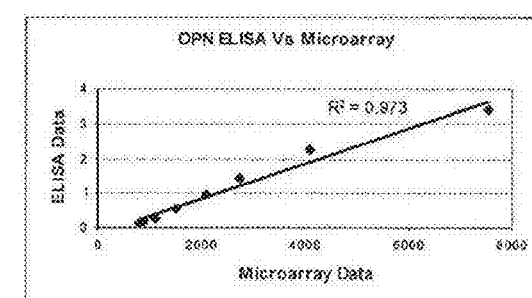
Figure 10:
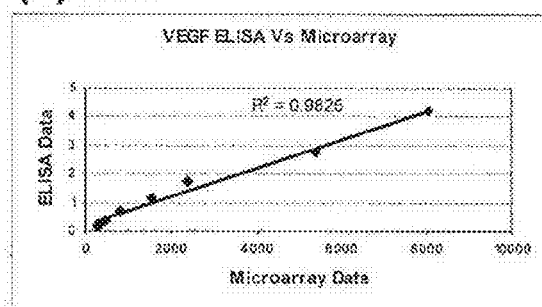

The developed microarray immunoassay offers many advantages over the traditional ELISA technique, including smaller size, lower costs, and multiplexing capability. Similar to the ELISA, we carefully optimized the concentrations of antibodies on the microarray to yield sensitive dose response curves. FIG. 10 shows the comparison of the standard curves obtained for each of the biomarkers using microarray technology and the ELISA in a scatter plot. Protein microarray shows similar dynamic range. Data from the two methods showed a linear relationship with a correlation coefficient ($r^2$) of greater then 0.97, indicating that both methods produce similar results.

The background noise due to non-specific adsorption of protein on the microarray glass surface increases with increasing protein concentration. Therefore, the detection of a specific target protein is limited not only by its concentration, but also by the concentration of the other proteins in the mixture. Serum is a complex mixture of many proteins with a very high concentration (~85 mg/ml) compared to PBS (0 mg/ml) causing significantly higher background levels in the assays developed using serum instead of PBS as the medium. The four biomarkers were detectable above this noise level in this assay. However, for proteins present in very small amounts (pM or fM) in serum, the high background can reduce the sensitivity of the assay. In that case, the abundant proteins (such as albumin) could be filtered out and the serum could be concentrated to enhance the detection limit. The signal can be amplified using specific secondary antibody molecules.

Microarray Multiplexed Assays

To demonstrate that this array technology could be used to simultaneously detect multiple biomarkers, all five protein biomarkers were analyzed in one single microarray. In this experiment, twelve identical slides were printed with capture antibodies to the five protein biomarkers. One of these slides was incubated with a mixture of all five antigens in the high concentrations observed in cancer, while one slide was incubated with a mixture of all five antigens in the lower concentrations observed in normal sera. Five slides were incubated with the same mixture of proteins containing all but one biomarker and the other five slides were incubated with only one antigen. The specificity of our immunoassays is illustrated in the FIG. 11(A).

Four (Her-2, MMP-2, CA 15-3 and OPN) of the five biomarkers diluted in PBS were able to be detected, simultaneously with high sensitivity and specificity in the assays. However no signal was observed for VEGF even at high concentrations. While VEGF could be sensitively detected in a singleplex assay (FIGS. 8E and 9E) very strong laser settings (power=100% and PMT gain 95%) had to be used. This posed a problem in the multiplexed format where the other biomarkers were sensitively detected at lower laser settings (70% laser power and 75% PMT gain). Therefore, two scans were performed, one at the lower setting to obtain fluorescence signals from the four biomarkers and one at the higher setting to obtain fluorescent signals from VEGF. No VEGF signal could be observed at the low laser setting and at the higher laser setting, tremendously high backgrounds were observed with reduced the signal to noise ratios for all the biomarkers. Therefore, in a further effort to selectively increase signal strength from VEGF, a biotinylated goat anti-rabbit secondary antibody specific to the biotinylated rabbit anti-VEGF antibody in the mixture was used. In this procedure, the microarray was first incubated with the antigen mixture followed by incubation with biotinylated antibodies to the five biomarkers, Her-2, CA 15-3, MMP-2, OPN and VEGF. The microarray was subsequently incubated with biotin-anti rabbit secondary antibody. This step was introduced to specifically amplify the VEGF signal since the biotinylated antibodies for the other 4 biomarkers were prepared in goat or mouse as the host. However, this antibody cross-reacted with the monoclonal capture antibodies for all the biomarkers, thus generating very high background noise. Recombinant antibodies engineered for affinity and specificity can in the future improve the multiplexing capability of assays by eliminating cross-reactivity and by increasing sensitivity. This would offer the antibody arrays a flexible, quantitative range and thereby increasing the pool of biomarkers that can be potentially assayed simultaneously.

Figure 11:
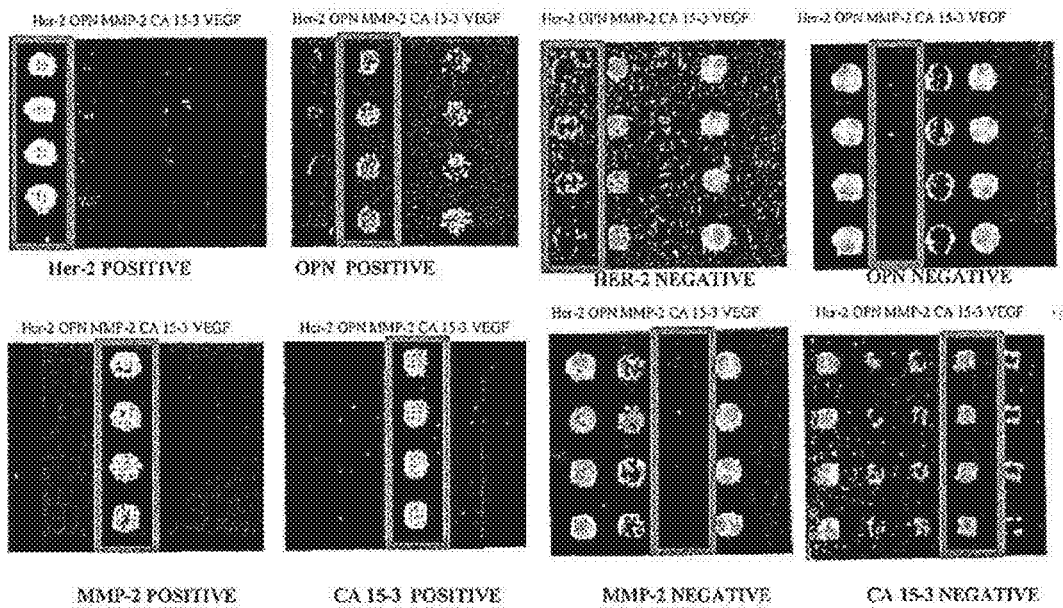
FIG. 11 shows multiplexed assays on protein microarrays.
Figure 11:
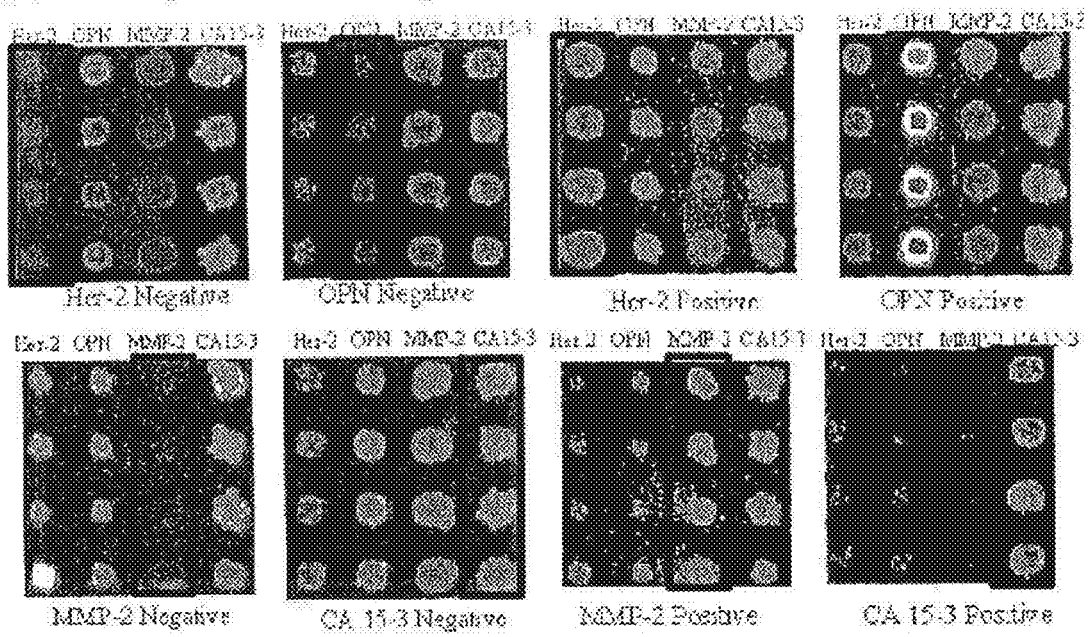

A multiplexed assay similar to the one described above was developed, but replacing PBS with human serum as the medium. The results from this assay are shown in FIG. 11 (B). In assays where only one antigen was preset it was observed that the signal from the other spots is not negative. This is also observed when a particular antigen is left out of the mixture, as serum contains these proteins in low concentrations unlike PBS, which contains no protein at all. Also the overall background noise arising from serum on the slide is much higher than the PBS arrays, similar to the effect observed in the standard curves using serum.

Example 2

Sensitive Multiplexed Diagnostic Test for Breast Disease

The multiplexed protein microarray assay developed previously is applied to the differential detection of four biomarkers in breast cancer patient sera.

Materials and Methods

Microarray assay reagents and protocols are essentially similar to those described above in Example 1. Recombinant proteins, capture and biotinylated detection antibodies for Her-2, MMP-2 and Osteopontin were purchased from R&D systems (Minneapolis, Minn.). Other reagents used in the assay include: VEGF antigen and capture and biotinylated detection antibodies (Biosource International Camarillo, Calif.), CA 15-3 antigen and anti-CA 15-3 capture and detection antibodies (Fitzgerald, Concord, Mass.). The CA 15-3 detection antibody was biotinylated using a kit and according to the manufacturer's (Pierce, Rockford, Ill.) instructions. All other detection antibodies were purchased as biotin conjugates. Lyophilized human serum was purchased from Rockland Immunochemicals (Gilbertsville, Pa.). Streptavidin conjugated Alexa 546 was purchased from Invitrogen-Molecular Probes (Carlsbad, Calif.), GAPS II™ slides were purchased from Corning LifeSciences (Corning, N.Y.) and BSA was purchased from Sigma-Aldrich (St. Louis, Mo.). Sera from 41 metastatic breast cancer patients, 33 breast cancer patients with early stage disease and 39 controls were obtained from the Breast Cancer Serum Resource, Lombardi Cancer Center (Washington, D.C.). Capture antibodies used were: 1) Her-2 (R&D systems; Monoclonal Anti-human ErbB2 Antibody; MAB-1129; Clone 191924), 2) MMP-2 (R&D systems; Monoclonal Anti-human MMP-2 Antibody; MAB-902; Clone 36006.211), 3) CA 15-3 (Fitzgerald; Monoclonal Anti-human CA 15-3 Antibody; 10-C03; Clone M8071022), 4) Osteopontin (R & D Systems; Monoclonal Anti-human Osteopontin Antibody; MAB-1433; Clone 190312), and 5) VEGF (Biosource; VEGF purified mouse anti-human; AHG011; Clone A183C-13G8). Detection antibodies used were: 1) Her-2 (R & D Systems; Polyclonal Goat Anti-human ErbB2 Antibody; AF-1129), 2) MMP-2 (R & Systems; Polyclonal Goat Anti-human MMP-2 Antibody; AF-902), 3) CA 15-3 (Fitzgerald; Monoclonal Anti-human CA 15-3 antibody; 10-C03B; Clone M8071021), 4) Osteopontin (R & D Systems; Polyclonal Goat Anti-human Osteopontin Antibody; AF-1433), and 5) VEGF (Biosource; Polyclonal Rabbit Anti-human VEGF Biotin Conjugated Antibody; AHG9119).

Microarray Spotting Protocol

Aminosilanated, GAPS II™ barcoded glass slides were spotted with capture antibodies using a robotic arrayer (Norgen Systems Inc.; Mountain View, Calif.) in quadruplicate at 500 μg/ml to form a 4×4 array grid. Four print heads were used to deposit approximately 1 nl of capture antibody solution, generating a total of 8 arrays per slide with 250 μm diameter spots and with a spot-to-spot distance of 350 μm. The spotted slides were cross-linked under ultraviolet light for 5 minutes and were stored in the dark at 4° C.

Multiplexed Microarray Assay Protocol with Patient Sera: Pilot Study

The eight arrays were separated from each other using silicone gasket chambers (Schleicher & Schuell Bioscience, Keene N.H.) and were blocked with 1 mg/ml BSA solution for 30 minutes followed by incubation with 50 μl of patient serum sample for 60 min. A total of 30 different patient serum samples were used in this study (10 metastatic, 10 early stage and 10 control). This experiment was performed in duplicate, for control and early stage patients, but replicates were not used for metastatic patients due to limited availability of samples. Arrays were then washed in PBS-T for 15 min followed by incubation with detector antibody "cocktail" containing biotinylated antibodies for all four biomarkers at a concentration of 3.75 μg/ml for 60 min. Streptavidin conjugated Alexa 546 was used as the reporter at a concentration of 5 μg/ml for 10 min. The chambers were then removed and the slides were agitated in PBS-T for 10 minutes and dried by centrifugation prior to scanning Multiplexed Microarray Assay Protocol with Patient Sera: Larger Sample Set Multiplexed capture antibody arrays were printed as described in the above section. In this assay, two control molecules were also included on the slide. Bovine serum albumin (BSA) served as negative control (NC). Alexa 546 spots were used as positive controls (PC). A total of 87 patient samples were used in this study, 29 of which were metastatic, 29 were early stage and the other 29 were control samples. The experiment was also planned such that each slide contained all the three sample categories (Control, Early stage and Metastatic) and each sample was split into two aliquots, which were placed on different slides. This arrangement accounted for inter-slide technical variation. The microarray assay was performed in a manner similar to Example 1.

Microarray Assay Protocol: Standard Curves

In this case, the protein microarrays were incubated with 50 μl of recombinant antigen diluted in human serum for 60 min, after the blocking step with BSA. The concentrations of biomarkers used to establish these standard curves were 1 ng/ml-128 ng/ml for Her-2, 10 ng/ml-1280 ng/ml for MMP-2, 2 U/ml-256 U/ml for CA 15-3, 10 ng/ml-1280 ng/ml for OPN, and 1 pg/ml-1280 pg/ml for VEGF. Serum without any added recombinant antigen was used to determine the baseline levels of the biomarkers. The solution was aspirated and washed with PBS-T for 15 minutes and the wells were then incubated with 100 μl of biotinylated antibody solution for 60 minutes. Following a 15 minute wash, the arrays were incubated with 100 μl streptavidin conjugated Alexa 546 for 10 minutes. The chambers were then removed and the slides were agitated in PBS-T for 10 minutes and dried by centrifugation prior to scanning Microarray Imaging and Analysis Protocol Slides were imaged with ScanArray 5000 XL (Perkin Elmer, Wellesley, Mass.), which is a laser-based confocal scanner, at 543 nm excitation. Images collected onto a PC were analyzed by Scanarray Express™ software (Perkin Elmer, Wellesley, Mass.). Raw intensities for each spot were computed by taking the average of the logarithm of the intensity over all pixels in the region of interest that were greater than zero for the spot. Median fluorescent intensities of all four spots for each biomarker were then computed for all patient samples. Principal component analysis was used to linearize the four dimensional data obtained from the measurement of four biomarker levels. Linear discriminant analysis was used to measure the accuracy of classification of unknown samples into appropriate disease categories (control, early stage or metastatic) based on biomarker levels. Both of these statistical functions were carried out using MATLAB.

Results

Figure 12:
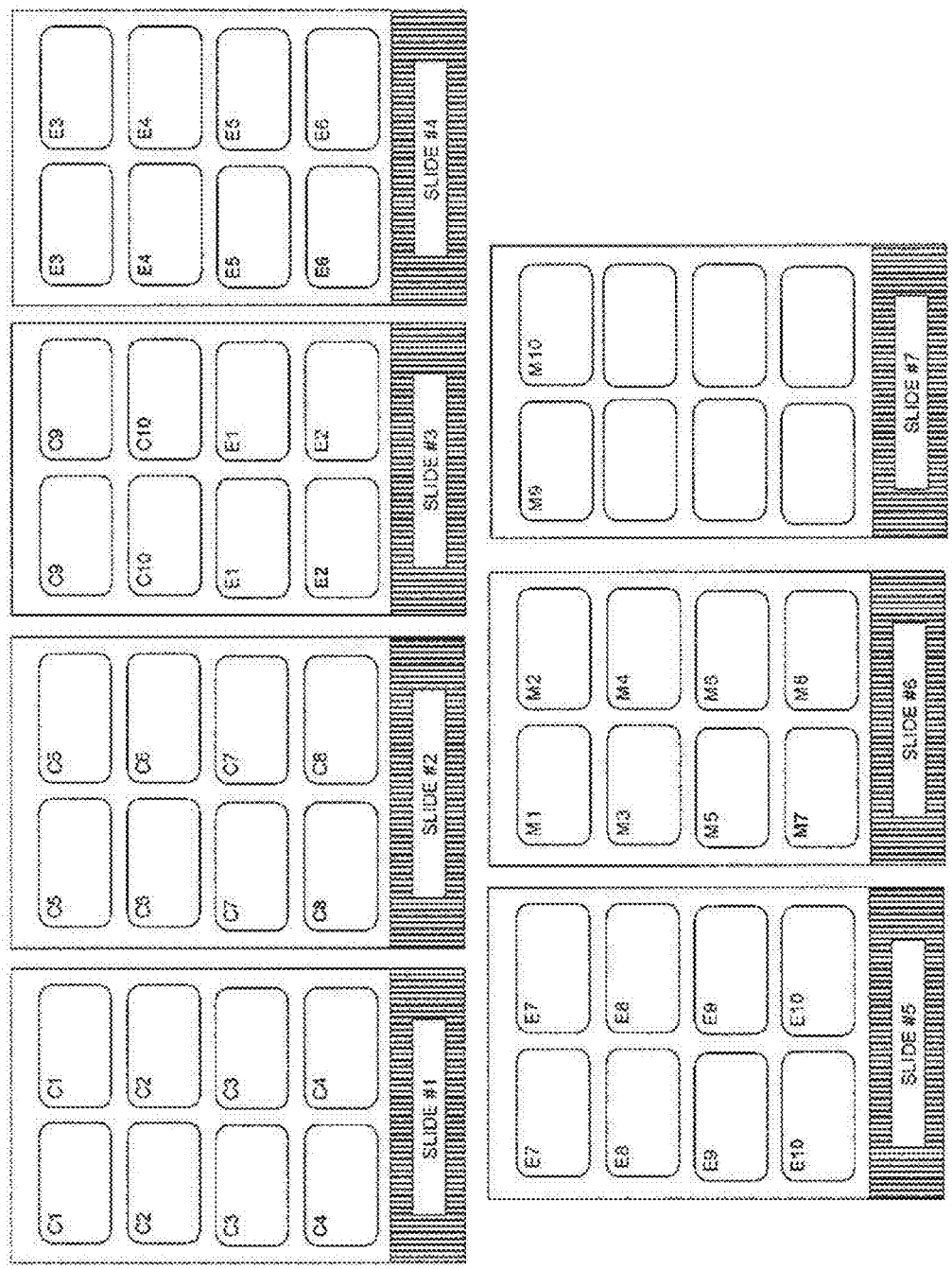
FIG. 12 shows the experimental layout of the breast cancer sample pilot study.

Antibody arrays were prepared by spotting multiple capture antibodies on amine-modified glass slides. These arrays were incubated with 50 µl breast cancer patient serum samples that were arranged on the slides as shown in FIG. 12. The notation C stands for control populations, E for early stage patients and M for patients with metastatic disease. A total of 30 patient sera were used; 10 controls, 10 early stage and 10 metastatic. The control and early stage samples were used in duplicate aliquots and the metastatic samples were used in single aliquots due to limited amount of sample.

Figure 13:
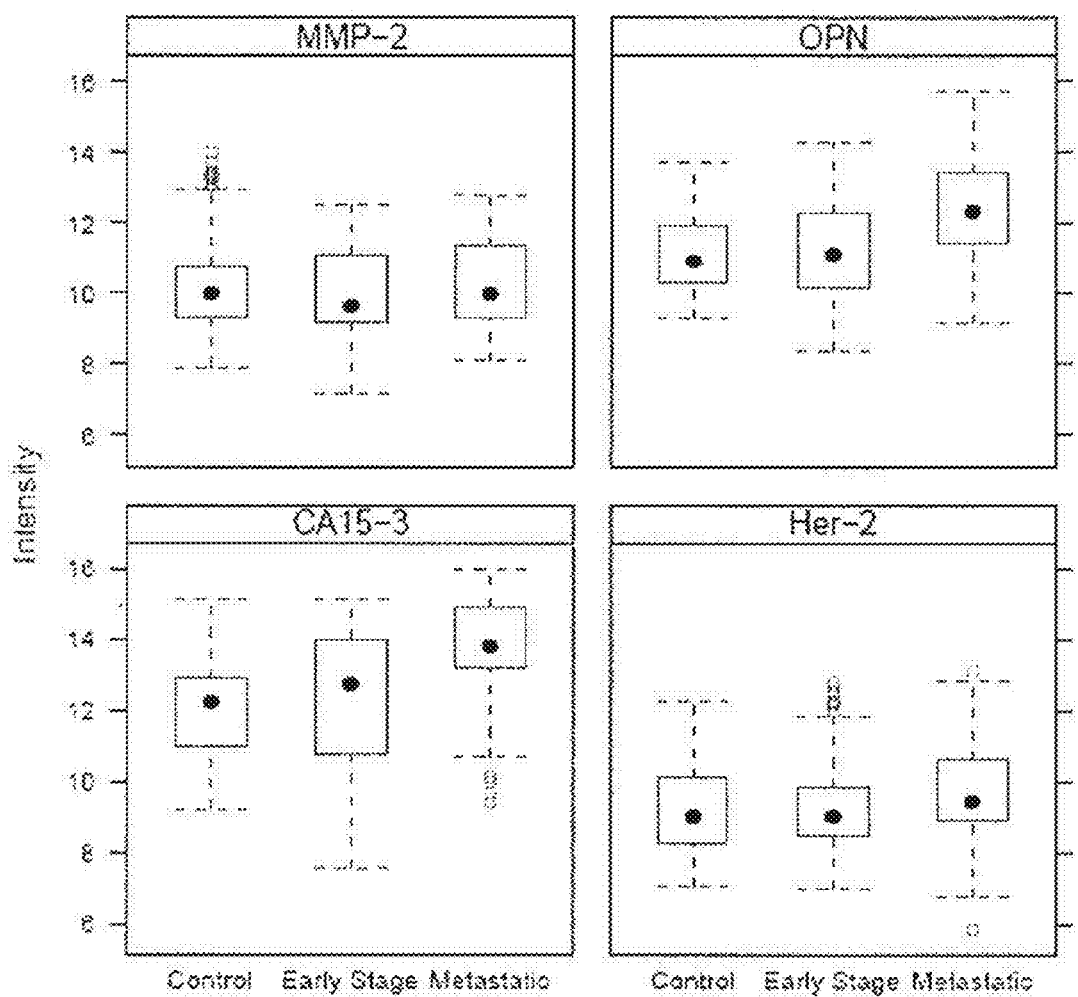
FIG. 13 shows the pilot studies with 30 breast cancer patient samples.

FIG. 13 shows the quantification of the fluorescent intensities using box plots, which is an efficient method for displaying a five-point summary of the data. Median fluorescent signals were obtained for each of the biomarkers and their log (to the base 2) values were plotted in the FIG. for each disease state. This demonstrated the effect of disease state on individual marker concentrations in serum. The upper boundary or hinge of the box represents the $75^{th}$ percentile of the data and the lower boundary represents the $25^{th}$ percentile of the data. Thus, the box represents the middle 50% of the data and this region is called the inter-quartile range. The dot inside the box represents the median value of the data. In this case, the data is skewed since the median value is not equidistant from the hinges. The ends of the vertical lines or whiskers indicate 1.5 times the value of the inter-quartile range, while the spots outside the whiskers denote the outliers.

An increasing trend of fluorescent signal from control samples to metastatic samples for the two biomarkers CA 15-3 and Osteopontin was observed. For the other two biomarkers, however, this trend is more subtle. This assay was planned such that each slide contained all control, early stage, or metastatic samples. This allowed measurement of technical variations within a slide only for one data set, and not across the three cancer groups. Since this assay did not include any controls on the slides, it was difficult to measure and account for slide-slide variation. Therefore, an accurate measure of fluorescent response to disease state could not be made. Using a total of 30 patient samples, however, showed promise for at least two of the biomarkers in as a diagnostic test. We expanded this study by including more samples in hopes of improving the sensitivity for Her-2 and MMP-2 as well as to confirm the results obtained for CA 15-3 and Osteopontin.

Multiplex Biomarker Study Using Patient Sera

Figure 14:
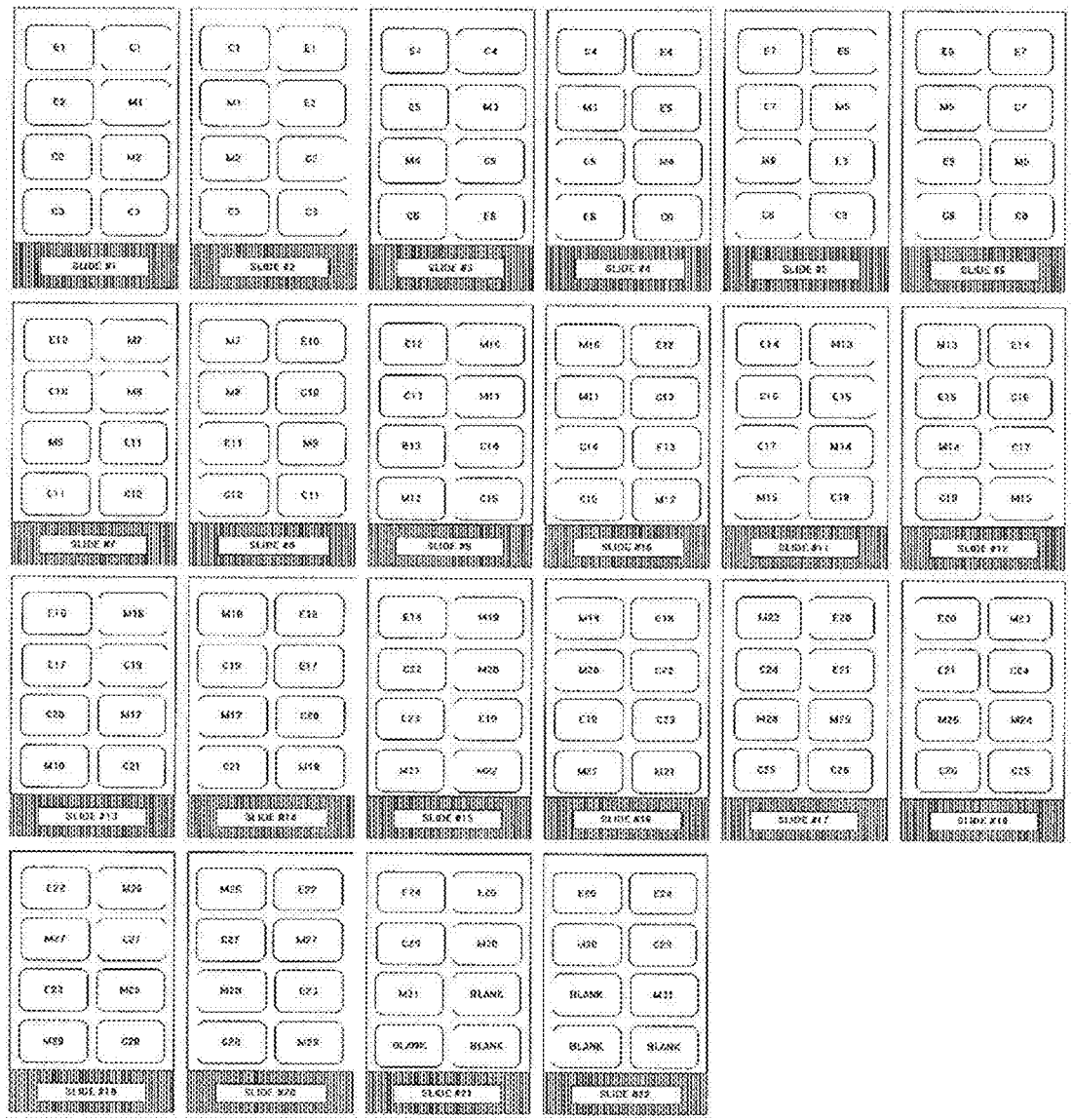
FIG. 14 shows the experimental layout of the breast cancer study.

In the breast cancer patient pilot study, the layout of the samples on the slides made it difficult to separate the effects of slide-to-slide variation from true differences in biomarker levels among normal subjects and patients with early or metastatic breast cancer. Differences were seen between metastatic and control sera for CA 15-3 and OPN only upon ignoring the effect of slide-slide variation. Thus, an additional study was designed in a different manner, to account for these variables. In this assay, antibody arrays were prepared similar to those described above, except that two additional controls were included on the slide. Bovine serum albumin (BSA) served as negative control (NC). Alexa 546 spots were used as positive control (PC). The sample size was increased to 87 patient samples in this study to include 31 metastatic, 23 early stage and 29 control samples. FIG. 14 shows the layout of this experiment, which was planned such that each slide consisted of a combination of control, early stage, and late stage samples. The sample was split into two aliquots, assigned to two arrays, on different slides. The samples were randomly assigned to the eight wells. On the last two slides (21 and 22) blank samples were included to account for the background fluorescent signals. This arrangement helped to account for the various technical variations that were not calculated in the pilot study.

Figure 15:
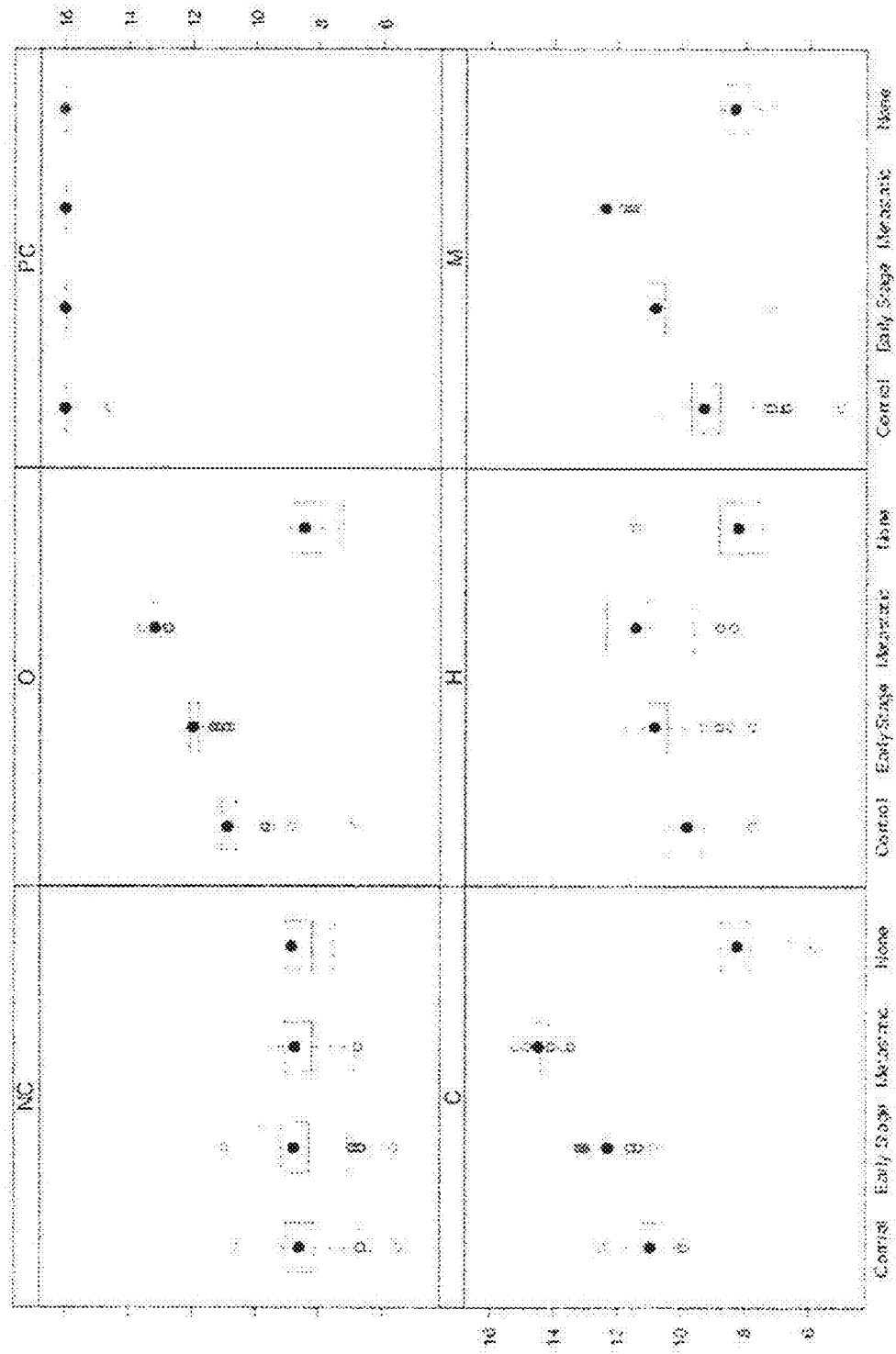
FIG. 15 shows the measurement of biomarkers in breast cancer patient sera.

FIG. 15 shows box plot representations of the fluorescent signals obtained for the four biomarkers as well as controls on the 22 experimental slides. The positive control (Alexa-546) spot fluorescence remained at a constant high level across all the experimental slides and the negative control (BSA) spot fluorescence was consistently low across all 22 slides. An increasing trend of fluorescent signal from control samples to metastatic samples was observed for all of the four biomarkers. The multiplexed microarray assay was able to distinguish between control, early stage, and metastatic populations for all the biomarkers with a fairly high accuracy (p value<0.05). Samples which contained only blank blocking grade human serum (slides 21 and 22) were used to measure the biomarker background noise levels. In the FIG., this background value matches that observed for the negative control (BSA) spots. NC=Negative control, O=OPN, PC=Positive control, C=CA 15-3, H=Her-2, and M=MMP-2.

Her-2 Status of Patients

Her-2 gene is amplified in about 30% of all breast cancers. HER2-positive breast cancers tend to be more aggressive than other types of breast cancer and they are also less responsive to hormone treatment. Trastuzumab (Herceptin) is a monoclonal antibody drug that targets HER2 and is used as an effective form of treatment for Her-2 positive breast cancer patients. This is shown to slow the growth of the cancer and even decrease its size. Herceptin can be used as a treatment by itself or combined with chemotherapy. Herceptin is also shown to reduce breast cancer recurrence by as much as 50 percent, thereby demonstrating a high rate of success in the patient survival. Detecting the Her-2 status of breast cancer patients, therefore, has become a routine and crucial step in treatment decision making. The standard procedure for determining whether a patient is Her-2 positive involves the use of Fluorescence In Situ Hybridization (FISH) to detect the over amplified Her-2 gene. Sometimes, an ELISA is performed to measure serum Her-2 levels, in which case, the patient is said to be Her-2 positive if the serum Her-2 level is higher than 15 ng/ml. The Her-2 status information was obtained for some of the patient serum samples from the Lombardi cancer center's serum repository and compared it to the measured Her-2 levels in sera of the same patients using the multiplexed microarray assay. Using the same rule as the ELISA, a patient serum sample was declared as Her-2 positive if the Her-2 levels were measured above 15 ng/ml. The results (shown in Table 1) show a 100% correlation in the conclusions of Her-2 status derived from our multiplexed assay and by traditional FISH or ELISA methods (as obtained from the Lombardi Cancer Center). While both these methods consume large (a few hundred microliters) quantities of sample and reagents and require anywhere between 8-24 hours to produce results, the microarray assay was performed with 50 ml of serum sample in 3 hours. The value of the multiplexed assay lies in the fact that the panel of biomarkers could not only be used for disease diagnosis, but also to simultaneously provide valuable information about treatment options for the patient.

TABLE 1

| Sample # | Stage of Cancer | Her-2 status of sample | | Measured Her-2 level |
|---|---|---|---|---|
| | | Lombardi Cancer Center | protein microarray | |
| 1 | Early stage | − | − | 9.62 |
| 2 | Early stage | − | − | 12.54 |
| 3 | Early stage | − | − | 12.38 |
| 4 | Early stage | − | − | 13.47 |
| 5 | Early stage | − | − | 7.42 |
| 6 | Early stage | − | − | 5.37 |
| 7 | Early stage | − | − | 9.03 |
| 8 | Early stage | − | − | 10.21 |
| 9 | Early stage | + | + | 17.44 |
| 10 | Early stage | + | + | 19.77 |
| 11 | Early stage | + | + | 24.07 |
| 12 | Early stage | + | + | 23.62 |
| 13 | Early stage | + | + | 19.32 |
| 14 | Metastatic | − | − | 11.62 |
| 15 | Metastatic | − | − | 13.79 |
| 16 | Metastatic | + | + | 45.73 |
| 17 | Metastatic | + | + | 46.82 |
| 18 | Metastatic | + | + | 49.15 |
| 19 | Metastatic | + | + | 13.43 |

Quantitation of Biomarker Levels in Patient Sera from Fluorescent Signals

Figure 16:
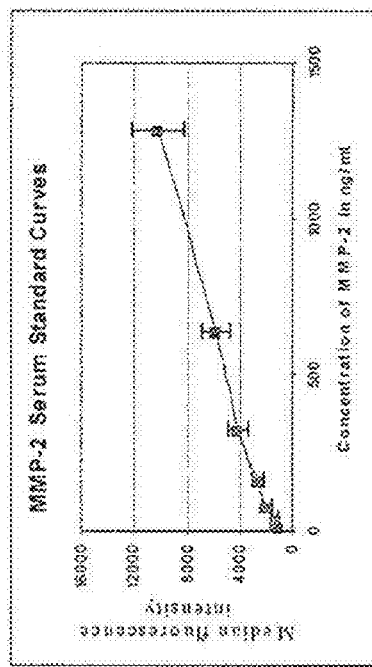
FIG. 16 is the standard curves for biomarkers in multiplex format.
Figure 16:
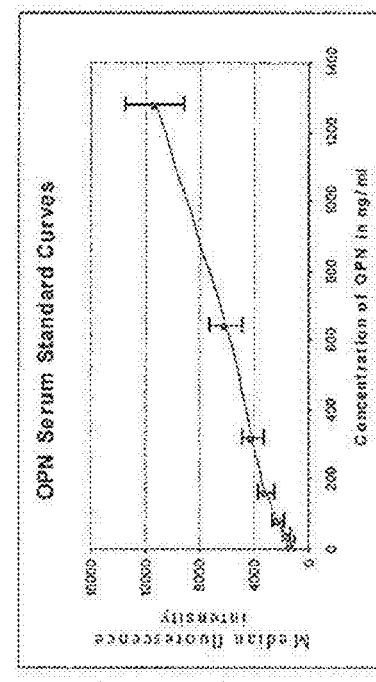
Figure 16:
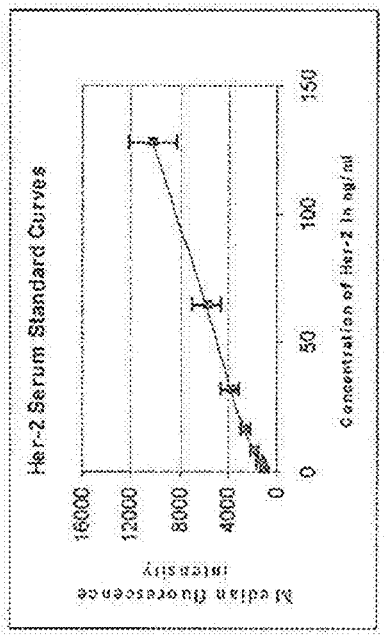
Figure 16:
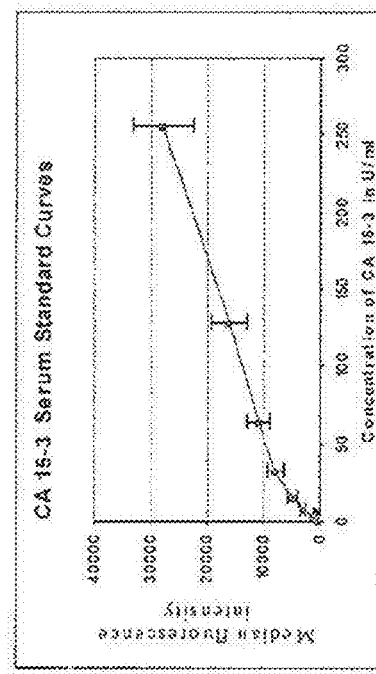

Antibody microarrays were used to generate standard curves to quantify the biomarkers in patient serum samples. These curves were obtained in a similar manner to the experiment described above, except that these curves were obtained on the same day and using the same set of slides as the patient samples, to minimize technical error. Capture antibodies to the four biomarkers were printed on modified microarray slides using a robotic arrayer such that each antibody was present in quadruplicate. Slides were then incubated with 8 serial dilutions of recombinant antigen diluted in human serum. The concentration ranges used were 1 ng/ml-128 ng/ml for Her-2, 10 ng/ml-1280 ng/ml for MMP-2, 2 U/ml-256 U/ml for CA 15-3 and 10 ng/ml-1280 ng/ml for OPN. All four detector antibodies were used in this experiment to simulate the multiplexed assay with the patient samples. Standard curves were obtained for each biomarker by quantifying the fluorescence from the arrays and plotting the median values as a function of antigen concentration. This can be seen in FIG. 16 (A-D). The standard curves were used to quantify the fluorescent intensities from patient serum samples assayed on the multiplexed arrays. This demonstrates the sensitivity and accuracy of our multiplexed microarray assay.

Relationship Between Use of Multiple Biomarkers and Accuracy of Diagnosis

Figure 17:
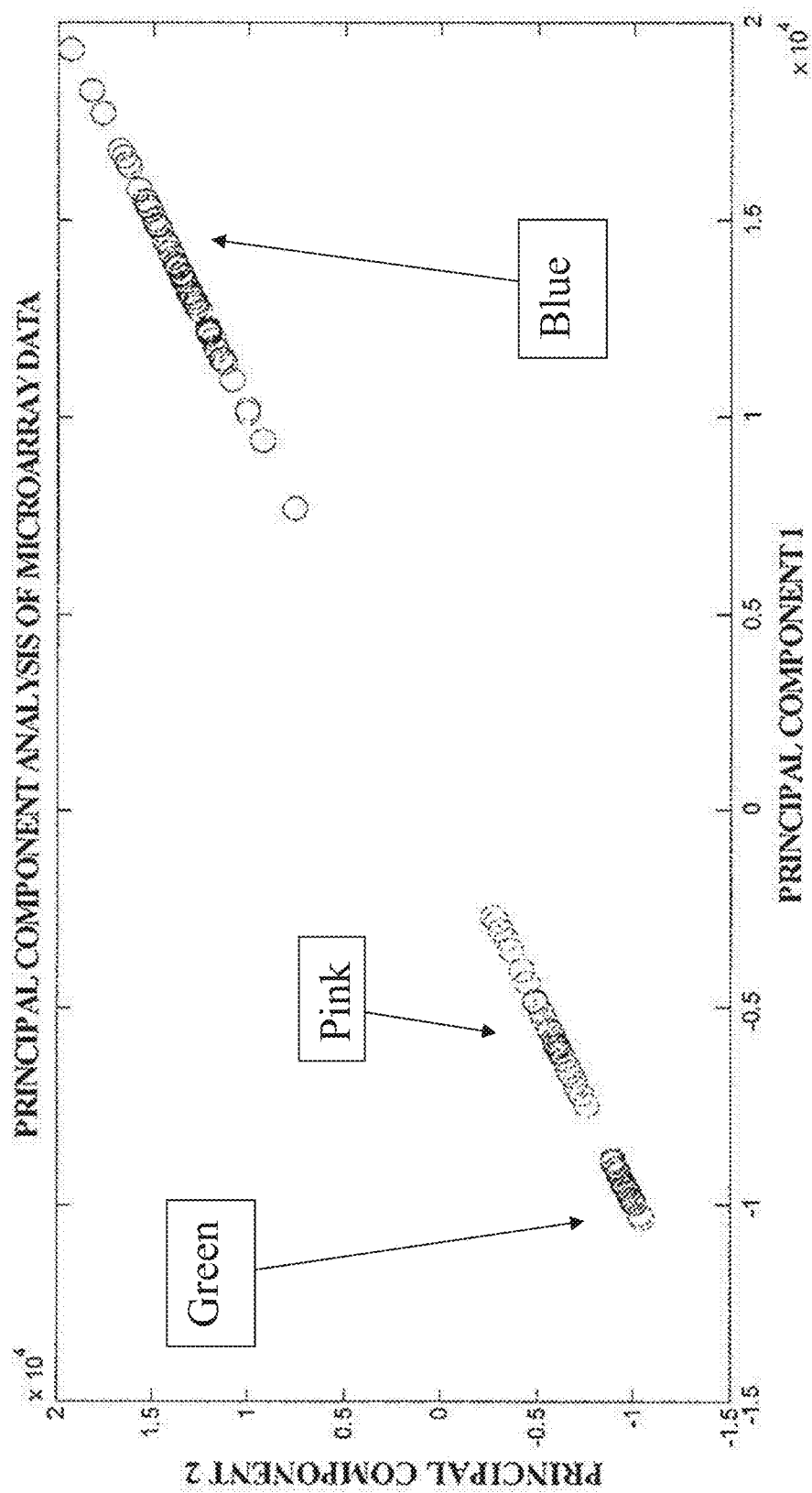
FIG. 17 shows clustering and linearization of the four dimensional data obtained using the multiplex assay and principle component analysis.

Although box plots shown above provide information about the distribution of the data for each individual biomarker, they are unable to provide information about all four biomarkers simultaneously. This method also does not address the hypothesis that multiple markers working in synergy provide a more sensitive diagnosis of breast cancer. Thus, Principal Component Analysis (PCA) was used to visualize the data from all four biomarkers in one single plot. PCA is a classical statistical method that reduces the dimensionality of a data set while retaining as much information as is possible. It performs a linear transformation that chooses a new coordinate system for the data set such that the greatest variance of the data set lies on the first axis (called the first principal component), the second greatest variance on the second axis, and so on. It can be viewed as a rotation of the existing axes to new positions in the space defined by the original variables. There can be as many principal components as there are variables. The first principal component accounts for much of the variability in the data, and each succeeding component accounts for the remaining variability. Principal components were computed for the data set that contains fluorescence signals from four biomarkers. FIG. 17 shows a scatter plot of first principal component on the X-Axis and the second principal component on the Y-Axis. Each vector of the principal components corresponds to a patient serum sample, displayed in the FIG. as control populations in green, early stage patients in pink and metastatic patients in blue. It can be seen that the three groups are well separated with little or no overlap. This demonstrates that the four biomarkers are able to distinguish accurately between control populations and patients with early stage and late stage breast cancer.

Figure 18:
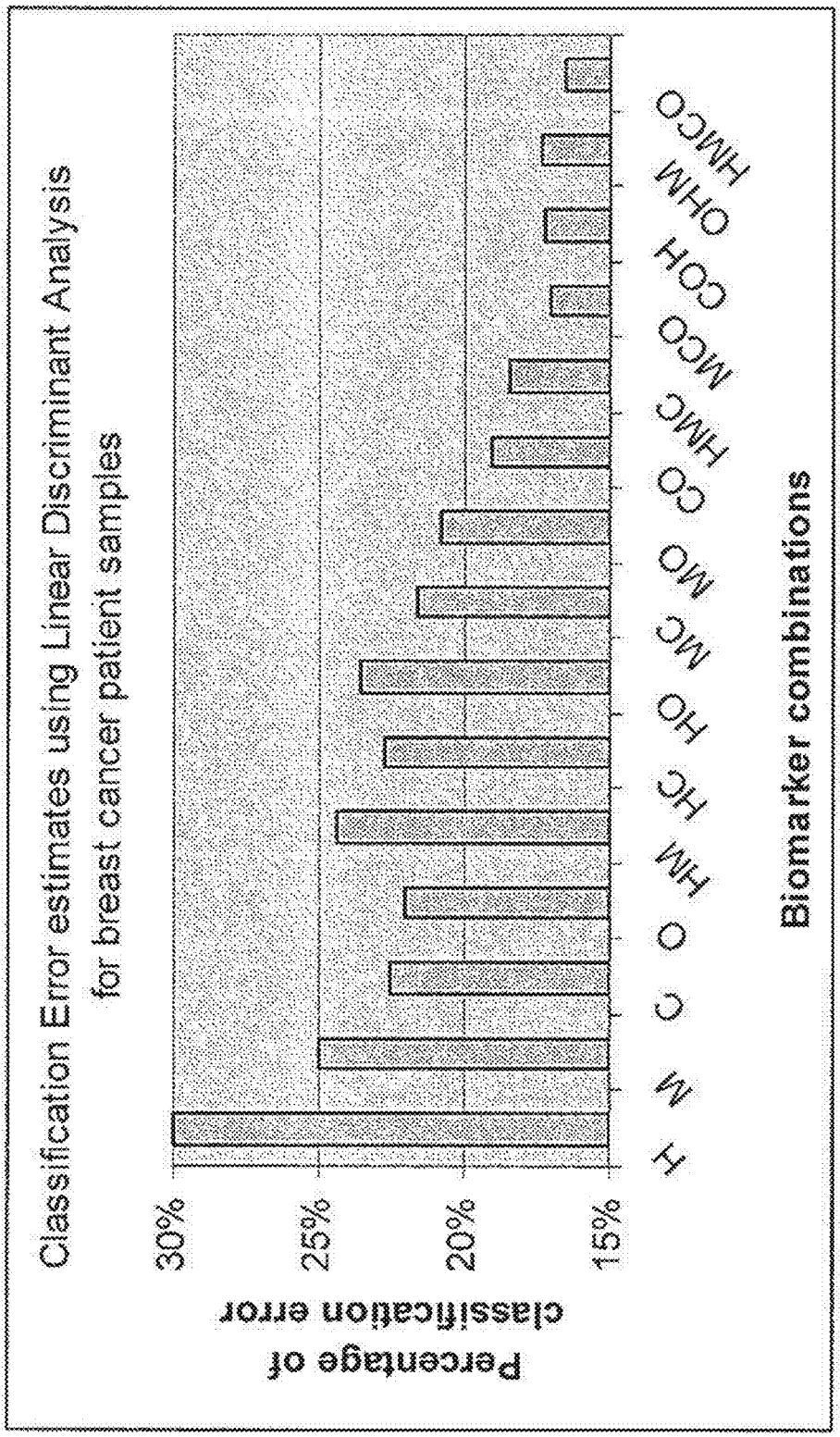
FIG. 18 shows classification error estimate using linear discriminant analysis; H=Her-2; M=MMP-2; O=OPN; C=CA 15-3.

For a diagnostic test, accuracy of classification is an important factor in its success. To measure the accuracy of classification of the test and to study the effect of number of biomarkers on this accuracy, Linear Discriminant Analysis was performed on the data set. This technique is useful for detecting the variables that allow the discrimination between different naturally occurring groups (e.g., breast cancer stages), and for predictive classification of unknown cases into their correct groups, establishing the robustness of this discrimination. This analysis was performed by dividing the data set into two parts. The first half was used as a training set and the second part was used as a test set. A linear discriminant function was built for the training set of the data and used the test set for cross-validation of predictive classification. This was used to produce unbiased estimates of chance of misclassifying the test set into the biological groups defined by the training set. This test was performed for all possible combinations of the four biomarkers to see the effect of number of biomarkers in the panel on the accuracy of classification. FIG. 18 illustrates the percentage of misclassifications occurred when the data was analyzed using various combinations of biomarkers. O=OPN, C=CA 15-3, H=Her-2, and M=MMP-2. It is observed that when only one single biomarker is used, the error of classification can be as high as 30%. When two biomarkers are used together, this error is reduced to approximately 24.35%. Adding another biomarker further reduces this error to approximately 18.5% and finally including all four biomarkers results in a 16.5% error. The reduction in error of classification is drastic from one to two biomarkers, but this difference starts to plateau when three and four biomarkers are included. Thus, it is possible that while multiple biomarkers do improve the accuracy of a diagnostic test, too many markers, can not provide any additional information. This is however, also determined by the biological nature of the biomarker and its physiological role in breast cancer. It should be noted that in particular the errors for CA 15-3 and Osteopontin are much less than those for Her-2 and MMP-2.

Example 3

Development of a Multiplexed Flow-Based Detector

A flow based platform was built with a unique custom flow channel device onto which, the multiplexed assay was translated from the protein microarrays. Below, the development of the device is described. A new flow-based immunoassay system for the simultaneous and rapid quantification of multiple analytes without several processing steps is described. This example also discusses the details of the device design, which is based on the standard microarray sandwich immunoassay format, except that the static incubation step was replaced with flow of the analyte mixture over the antibody array. Multiple steps have also been eliminated (including washing) by mixing all the assay reagents in predetermined concentrations in one single sample. In addition, a benchtop version of a portable imaging system was developed, comprising a miniature uncooled CCD camera and a Xenon arc lamp. This method demonstrated rapid quantitative measurement and specific identification of analytes in complex samples with minimal intervention.

Materials and Methods

Microarray Flow Channel Assay and Lateral Flow Assay Components

Her-2 and Osteopontin protein, capture and biotinylated detection antibodies as well as MMP-2-specific capture and biotinylated detection antibodies were purchased from R&D systems (Minneapolis, Minn.). Other reagents used in the assay include: CA 15-3 antigen and anti-CA 15-3 capture and detection antibodies (Fitzgerald, Concord, Mass.), MMP-2 Proenzyme (EMD Biosciences, San Diego, Calif.), biotin-BSA (Pierce Biotechnology, Rockford, Ill.) and Streptavidin Quantum Dot 605, Streptavidin Quantum Dot 585, Goat-anti-mouse-Quantum Dot 605 and Quantum Dot incubation buffer (Quantum Dot Corp (Invitrogen), Hayward, Calif.) and Strepavidin Alexa 546 (Molecular Probes Invitrogen Corp. Carlsbad, Calif.). Phosphate Buffered Saline (PBS; 50 mM potassium phosphate, 150 mM NaCl; pH 7.4) and Phosphate Buffered Saline with 0.05% Tween 20 (PBS-T) and BSA were obtained from Sigma Aldrich Corp. (St. Louis, Mo.). The CA 15-3 detection antibody was biotinylated using a kit and according to the manufacturer's instructions (Pierce Biotechnology, Rockford, Ill.). All other detection antibodies were purchased as biotin conjugates. Lyophilized human serum was purchased from Rockland Immunochemicals (Gilbertsville, Pa.). Sera from metastatic and early stage breast cancer patients and controls were obtained from the Breast Cancer Serum Biomarkers Resource, Lombardi Cancer Center (Washington, D.C.). The nitrocellulose membrane (NC) HF180, polystyrene clear backing and conjugate pad were from Millipore Corp. (Watertown, Mass., USA). GAPS II™ glass slides for the microarrays were obtained from Corning Lifesciences (Corning, N.Y.) and the silicone chambers from Grace Biolabs (Bend, Oreg.). Capture antibodies used were: 1) Her-2 (R&D systems; Monoclonal Anti-human ErbB2 Antibody; MAB-1129; Clone 191924), 2) MMP-2 (R&D systems; Monoclonal Anti-human MMP-2 Antibody; MAB-902; Clone 36006.211), 3) CA 15-3 (Fitzgerald; Monoclonal Anti-human CA 15-3 Antibody; 10-C03; Clone M8071022), 4) Osteopontin (R & D Systems; Monoclonal Anti-human Osteopontin Antibody; MAB-1433; Clone 190312), and 5) VEGF (Biosource; VEGF purified mouse anti-human; AHG011; Clone A183C-13G8). Detection antibodies used were: 1) Her-2 (R & D Systems; Polyclonal Goat Anti-human ErbB2 Antibody; AF-1129), 2) MMP-2 (R & D Systems; Polyclonal Goat Anti-human MMP-2 Antibody; AF-902), 3) CA 15-3 (Fitzgerald; Monoclonal Anti-human CA 15-3 antibody; 10-C03B; Clone M8071021), 4) Osteopontin (R & D Systems; Polyclonal Goat Anti-human Osteopontin Antibody; AF-1433), and 5) VEGF (Biosource; Polyclonal Rabbit Anti-human VEGF Biotin Conjugated Antibody; AHG9119).

Preparation of LFA Strip

Figure 19:
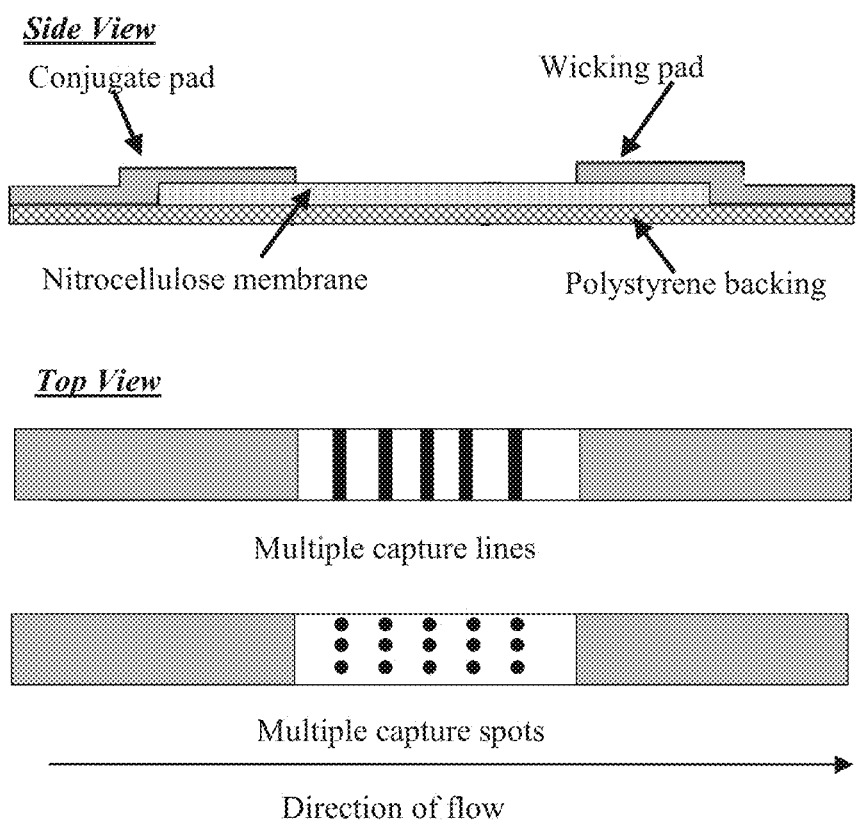
FIG. 19 is a schematic representation of a lateral flow test strip.

Similar to the conventional immunochromatographic strips, the LFA comprised a nitrocellulose membrane for separation and detection of analytes, a conjugate pad to collect the antibody-antigen complex, a wicking pad for the generation of capillary action, and a plastic backing card for the protection of the strip (see FIG. 19). Nitrocellulose membrane, the conjugate pad, and the absorption pad were laminated on the adhesive side of the polyester backing card. Capture molecules were dispensed and immobilized on the nitrocellulose membrane to form the detection zone using a precision-dispenser (Bio-Dot, Irvine, Calif.). The width of the dispensing line was 0.5-1 mm and the diameter of spots was 0.5 mm (20 nl) and 0.25 mm (10 nl) with a vertical spacing of 1.5 mm and horizontal spacing of 4 mm. 5 mm strips were cut using the guillotine cutter (Bio-Dot, Irvine, Calif.) to form individual tests.

LFA Assay Protocol

We adapted the principle of immunochromatographic assay for the analysis of multiple analytes in this study. Instead of 40-nm gold particles as used in conventional immunochromatography, Quantum Dots (QD) were used as the signaling molecule, which is bound to the detector antibody through a biotin-streptavidin bond. Fluorescent immunoassays were performed on these customized lateral flow membranes. In order to demonstrate proof of principle in the LFA system, biotin-BSA was spotted as a capture molecule onto nitrocellulose strips in both line (1 mm) and spot (20 nl and 10 nl) formats. Streptavidin-conjugated quantum dot solution was then wicked through the biotin-BSA.

To demonstrate the principal of multiplexed LFAs, the nitrocellulose membrane was spotted with biotin-BSA (500 µg/ml and mouse IgG µg/ml) as capture molecules and a mixture of Streptavidin-conjugated QD 585 (10 nM) solution and Goat anti mouse conjugated QD 605 (10 nM) solution was then wicked through the membrane. Resulting fluorescent signals due to the accumulation of quantum dots at these sites were observed on a UV transilluminator. For membranes that were spotted with capture antibodies, sandwich-type fluorescent immunoassays were performed on customized lateral flow membranes. When an analyte is first mixed with the quantum dot-linked detector antibody and then applied to the nitrocellulose membrane, the analyte-detector antibody-quantum dot complex moves from the sample pad toward absorption pad. During the propagation, the complex encounters the immobilized capture antibodies on the nitrocellulose membrane and forms sandwich-type detector-analyte-capture antibody complexes. This fluorescence was observed on the UV transilluminator.

Preparation of Microarray Channels

Unique flow channels were designed that allow for simple capillary flow of assay reagents without the need for complex fluidics and mechanical parts. Antibody microarrays were printed similar to traditional microarrays using a robotic arrayer (Norgen Systems Inc.; Mountain View, Calif.). Two print heads were used to deposit approximately 1 nL of capture antibody solution, generating a total of 2 arrays per slide with 225 µm diameter spots with a spot-to-spot distance of 350 µm. The layout of each 8×12 array of printed antibody spots corresponded to one spot per well in a standard 8×12 (96-well) format. These capture antibodies were printed in quadruplicate at a concentration of 1 mg/ml. Also printed on each slide were two controls. Bovine serum albumin (BSA) served as negative control (NC) and Alexa 546 was used as positive control (PC). The spotted slides were cross-linked under ultraviolet light for 5 minutes and were stored in the dark at 4° C. This scheme yields two channels per slide. As shown in FIG. 1, the channels are created by using adhesive silicone supports (0.5 mm height) and a glass cover slip facilitating fluid exchange through an inlet and an outlet (length=3 cm and width=1 cm). This helps draw fluids onto the immobilized antibody microarrays through capillary action. The fluid flow stops at the end of the channels at which point, it can be wicked with an absorbent material, the porosity of which can used to control the flow rate through the channels and hence the assay time.

Channel Assay Protocol Using Recombinant Antigen

For demonstrating proof of principle of quantitative detection on the microarray channels, protein microarray slides were printed with biotin-BSA in a series of 4 dilutions from 500 µg/ml to 62.5 µg/ml. The two arrays on the glass slide were separated using silicone channels as described above and were blocked with 1 mg/ml of BSA solution in PBS for 30 minutes. This solution was wicked and the arrays were allowed to air dry for two minutes. 200 µl of 10 nM streptavidin QD 605 was drawn into the channels and the fluid was completely wicked at the other end. The flow channels were removed and arrays were washed and air dried prior to scanning To demonstrate the multiplexing capability of the channel flow assays, two different capture molecules were immobilized; biotin-BSA at 500 µg/ml and mouse IgG at 500 µg/ml. Unconjugated BSA was used as a negative control. The microarrays in the channels were blocked with BSA at 1 mg/ml for 30 minutes followed by incubation with a streptavidin QD 605 and Goat anti-mouse IgG-QD 605 for 2 minutes in four different configurations. In the first set, no reporter was used, in the second set, both streptavidin QD 605 and Goat anti-mouse IgG-QD 605 were; in the third set, only streptavidin QD 605 and in the final set, only Goat anti-mouse IgG-QD 605 was used. The flow channels were removed and arrays were washed and air dried prior to scanning To demonstrate the sensitivity of the flow channels, standard curves were obtained for the four biomarkers of interest using sandwich immunoassays. A mixture of biotinylated detector antibody (at 10 µg/ml) and streptavidin-linked Alexa 546 (at 7 µg/ml) was added to serial dilutions of recombinant antigens prepared in phosphate buffered saline (PBS) and human serum. The antigen concentration ranges used were 6.25-100 ng/ml for Her-2, 62.5-1000 ng/ml for MMP-2, 9.4-150 U/ml for CA 15-3 and 94-1500 ng/ml for OPN. 200 µl of the sample mixture was added to the entry of the channels. Capillary forces helped wick this fluid into the channels over the printed capture antibodies for binding. Samples were added to duplicate arrays across different slides to account for technical variations. Following the appropriate incubation time, the fluid was completely wicked and the flow channels were removed. The chambers were then removed and the slides were agitated in wash buffer for 5 minutes and air dried prior to imaging.

To measure the specificity of the flow channel assays, a multiplexed assay was performed essentially as described for the standard titration curves. Capture antibodies for Her-2, MMP-2, CA 15-3 and OPN were spotted in quadruplicate at 500 µg/ml on the GAPS II™ slides to form a 4×4 array grid. A total of eight different samples were prepared, four of which contained a mixture of all but one antigen and four of the remaining samples contained only one antigen each. The concentrations of recombinant antigens diluted in human serum were 20 ng/ml Her-2, 800 ng/ml MMP-2, 130 U/ml CA 15-3 and 900 ng/ml OPN. Antibody microarrays were incubated with these antigen samples mixed a detector antibody "cocktail" containing biotinylated antibodies for all five biomarkers at a concentration of 15 µg/ml. Streptavidin conjugated Alexa 546 was used as the reporter at a concentration of 10 µg/ml. The samples were assayed in duplicate. The chambers were then removed and the slides were agitated in PBS-T for 10 minutes and dried by centrifugation prior to scanning To determine the optimum speed of the assay without compromising the assay sensitivity, a multiplexed assay was performed, essentially as described above. Two sets of samples were prepared. In the first case, the antigens were used at concentrations known to be present in metastatic cancer patients (30 ng/ml for Her-2, 850 ng/ml for MMP-2, 150 U/ml for CA 15-3 and 875 ng/ml for Osteopontin) and in the second case; the antigens were used at concentrations known to be present in control patients (8 ng/ml for Her-2, 600 ng/ml for MMP-2, 15 U/ml for CA 15-3 and 440 ng/ml for Osteopontin). 4 aliquots of 200 µl of the sample mixture was added to duplicate arrays and incubated for 7 min, 15 min, 30 min and 60 min respectively before sample was wicked. The chambers were then removed and the slides were agitated in wash buffer for 5 minutes and air dried prior to imaging.

Channel Assay Protocol: Serum Samples

Two types of experiments were performed to measure the response of the flow channels to the protein biomarkers in the sera of patients with breast cancer. In the first study, 80 µl of sera from each of the 10 metastatic breast cancer patients and 80 µl of sera from each of the 10 control subjects was pooled to obtain a total of 800 µl of metastatic breast cancer sample and 800 µl of control sample. 80 µl of this pooled sample was wicked across 10 arrays in duplicate for 7 min and 15 min respectively. The chambers were then removed and the slides were agitated in wash buffer for 5 minutes and air dried prior to imaging. This helped estimate the technical variations in the assay. To measure the biological variation, 80 µl of patient sera from 6 metastatic breast cancer patients and 6 control subjects was then mixed with 60 µl of biotinylated detector antibody cocktail and 60 µl of streptavidin Alexa 546 reporter to yield a final concentration of 10 µg/ml for the antibodies and 7 µg/ml for the reporter. This sample mixture was added to the arrays and incubated for 15 minutes before sample was wicked. The chambers were then removed and the slides were agitated in wash buffer for 5 minutes and air dried prior to imaging. Statistical comparison of the biomarker levels in breast cancer patients and controls was undertaken using a t-test and a probability value of was obtained using MATLAB software.

Bench Top Imaging System

As a gold standard imaging system, the ScanArray™ 5000 XL (PerkinElmer, Inc.; Wellesley, Mass.) was used at 543 nm excitation. This is a benchtop, laser-based confocal scanning device with a photomultiplier tube (PMT) for sensitive fluorescence detection. Images collected onto a PC were analyzed by QuantArray™ software. Raw intensities for each spot were computed by taking the average of the logarithm of the intensity over all pixels in the region of interest that were greater than zero for quadruplicate spots on a slide and across duplicate chambers resulting in a total of eight spots per sample for analysis.

A imaging system was also developed that supports a charge coupled device (CCD) camera as this technology is more amenable to building smaller portable instruments. The arrangement of this imaging system is shown in FIG. 2 and it consists of a scientific-grade 16-bit, 1392×1040 pixel CCD camera (Lumenera Corp. MA), which is configured for Köhler epi-illumination of the sample microarray. In this case, the fluorescent sample is illuminated from the front, while simultaneously being imaged from the same side by the CCD camera. Excitation light from a full-field White Lite® light 300 W xenon arc lamp was bandpass filtered using a 525 nm excitation filter (Omega Optical Inc, VT) and focused uniformly on the sample using a set of two optic fiber cables (mellesgriot) held at an angle of 45 degrees. The fluorescent spots were focused onto the CCD using a camera lens (Infinimite® alpha, Edmund Optics) and filtered using a 600 nm longpass filter. Custom algorithms, built within the Lumenera camera software corrected for CCD dark noise. Images saved in tiff format were analyzed using the Scanarray Express™ software (Perkin Elmer, Wellesley, Mass.).

Results

A method was developed that requires the addition of only one fluid sample and can therefore measure multiple biomarkers simultaneously in one simple process. This technology showed a potential to facilitate common use of antibody microarray in medical and scientific field for high-throughput detection of a wide variety of analytes.

Lateral Flow Assays

To achieve rapid, multiplexed detection, an LFA (as shown in FIG. 19) was developed which combines the multiplexed, quantitative advantages of the protein microarrays and the assay speed and simplicity of traditional LFA. Multiple capture molecules were spotted onto the nitrocellulose membrane, and the reporter mixture was applied to the conjugate pad at one end of the membrane. This complex was drawn through the membrane by capillary action, where the markers were captured by their respective ligands. This simple, yet rapid method required the addition of only one fluid sample without the need for washes. Fluorescent QD nanocrystals were employed as the reporter since they have an added advantage of being multiplexed, yet quantitative. The use of spectrally different QDs as well as spatial separation of these two capture molecules enables reliable multiplexed detection in this lateral flow format.

Figure 20:
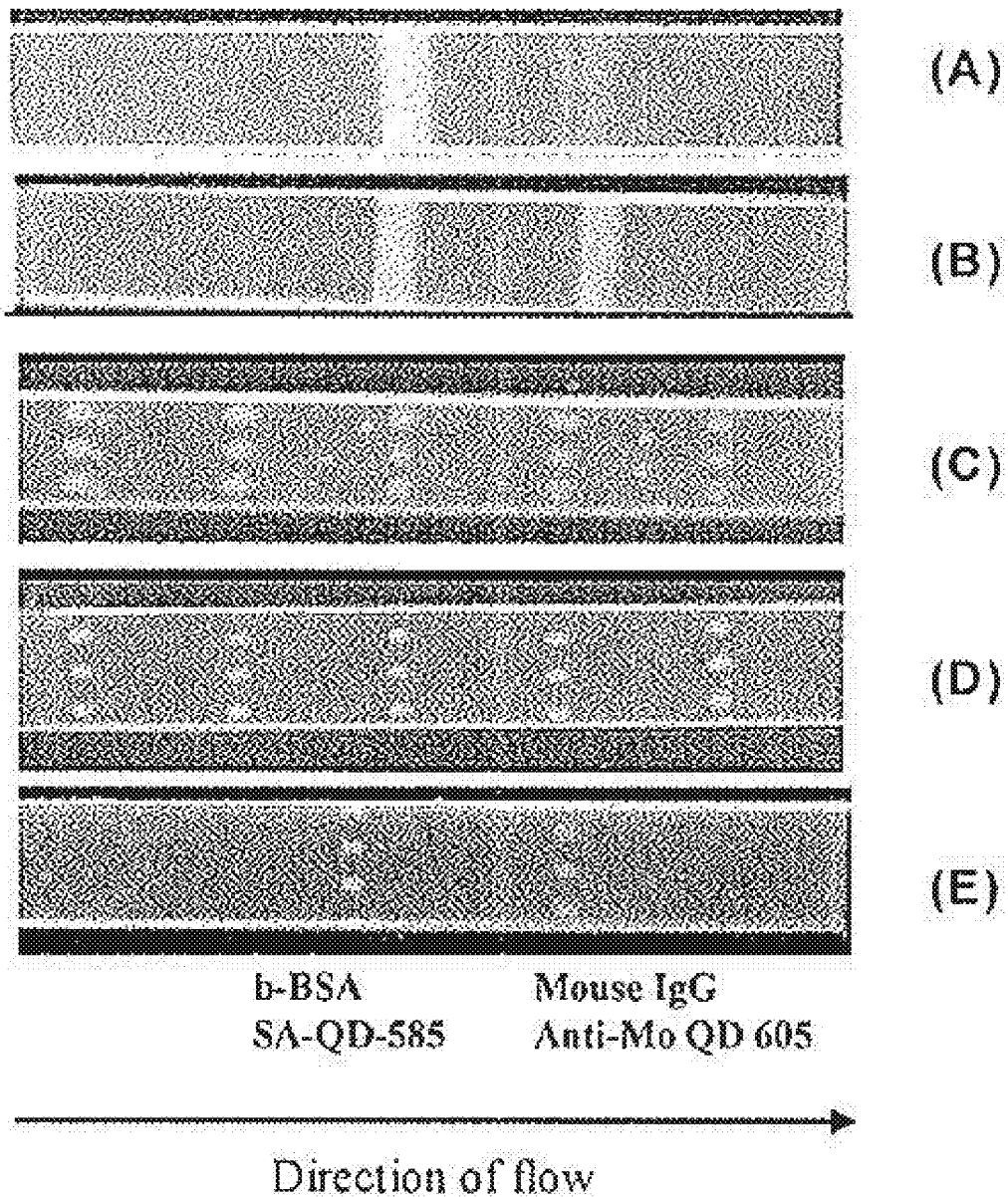
FIG. 20 shows fluorescence images of the lateral flow assay (LFA).

To demonstrate the proof of concept of multiplexed lateral flow assays, two test analytes (Biotin-BSA and mouse IgG) were detected on a single LFA. As shown in FIG. 20, when a mixture containing streptavidin conjugated QD 585 and Goat anti-Mouse conjugated QD 605 (both at 10 nM) is added to the conjugate pad (left side of the FIG.), it flows through the pores of the nitrocellulose membrane, to the capture zones where the streptavidin conjugated QD 585 binds to the biotinylated BSA and Goat anti-Mouse conjugated QD 605 binds to the mouse IgG respectively. Since the capture molecules are fixed on the membrane, the reporters continuously accumulate on the capture zone. This generates a signal proportional to the amount of immobilized capture molecules. FIG. 20(A) demonstrates a strip with biotin-BSA spotted as two consecutive 1 mm (100 nl) lines along the length of the nitrocellulose membrane at a concentration of 500 µg/ml and at 125 µg/ml in FIG. 20(B). In order to measure multiple analytes along the strip, it is important that the flow not be obstructed by the capture molecules. It is observed that with a capture concentration of 500 µg/ml very little signal is obtained from the second line. However, when the concentration of the capture molecule is reduced to 125 µg/ml, some signal is observed on the second line. When the concentration is kept high (500 µg/ml), but the dispensing volume is reduced to 20 nl, five columns of capture molecule can be observed (FIG. 20(C)). However, in this case, a reduction of signal intensity is observed in the direction of sample flow. When this capture volume is reduced to 10 nl (FIG. 20(D)), this gradation disappears and the spots have uniform fluorescence signal along the length of the membrane. The result suggested the possibility that multiple target proteins could be detected by adjusting the amount of capture antibody on the strip. To demonstrate this multiplexing capability of the LFA, one column (3 spots) containing biotin-BSA was immobilized and a second column (3 spots) containing mouse IgG (FIG. 20(E)). Two spectrally distinct sets of QDs were used for this assay and the mixture containing the two different detectors is accurately resolved on the LFA demonstrating its multiplexing capability.

The microarray LFA was then employed for the detection of the panel of breast cancer biomarkers including Her-2, CA 15-3 and Osteopontin. Monoclonal capture antibodies to the four antigens were immobilized on the nitrocellulose membrane as 10 nl spots. This spotting was done in six schemes such that the sequence in which the sample encountered the capture molecules was different in each assay. A mixture of antigens and biotinylated detector antibody labeled with streptavidin QD 605 as deposited on the conjugate pad. The concentrations of reagents used in this assay are Her-2 5 µg/ml, CA 15-3 500 U/ml and Osteopontin 3 µg/ml, biotinylated detector antibodies 30 µg/ml and strepavidin QD 605 10 nM. The solution was allowed to wick through the membrane and the spot fluorescence was observed on the UV transilluminator. Images were captured using a digital camera and displayed in FIG. 21, which shows that it is possible to observe signals from three antigens in this multiplex format. The signal to noise ratio was best for the case (C) and (E) where Her-2 is spotted at the far right hand side of the membrane. Although high concentrations of antigens were used, signal was barely observed above the high background in the membrane.

Accumulation of fluorescent quantum dot in the pores of the nitrocellulose membrane, as well as the high concentration of reagents in this assay cause a high background noise in the LFA. The LFAs had much lower sensitivity than that of the microarrays. The concentrations of capture and biotinylated detector antibodies were 8 fold and 6 fold higher than those used in the protein microarrays respectively, making the assay very expensive. Although the Her-2, CA 15-3 and OPN were detected in a multiplexed format, MMP-2 assay did not produce any signals on the LFA. The detection limits of the LFA for the antigens were approximately 10 fold higher than protein microarrays.

The reagents for the multiplexed assay were optimized specifically for the protein microarray platform as discussed above. By optimizing a brand new set of reagents for the LFA, it could improve the sensitivity of the assay as well as make MMP-2 work with the panel of biomarkers. The use of a membrane substrate with high affinity to proteins made LFAs prone to very high background noise. This is partially due to the fact that LFAs do not involve wash steps, and that the flow of analyte solution is through the membrane and not simply above the surface. This offers a three dimensional matrix to which the analyte, detector antibody and reporter complexes can bind non-specifically. Unlike the traditional Western Blots, ELISAs or Microarrays, the blocking agents employed to minimize the background levels bind to the membrane matrix and offer resistance to the flow of analyte through membrane. Additionally, such additives can displace capture reagents from the membrane, thereby, reducing assay sensitivity.

Channel Flow Assays

To design a new platform for rapid immunoassays, the antibody arrays were printed on a glass slide and instead of the static incubation chambers, unique flow channels were designed that cover individual arrays, and allow for passive flow of analyte mixture over the immobilized array. Channels are made by using adhesive silicone supports and a glass cover slip. This helps draw fluids onto the immobilized antibody microarrays through capillary action. Fluid flow enhances the kinetic interaction between the analyte and the immobilized ligand thereby overcoming the diffusion limitation of the incubation assays and reducing assay time. Since the flow is over the arrays and not through a three dimensional matrix as in the case of LFAs, the arrays can be treated with blocking agents to minimize background noise. This provides a rapid, simple, yet multiplexed platform to measure protein biomarkers in serum samples.

A mixture containing sample, detector antibody and fluorescent reporter at predetermined concentrations was added to the protein array. Capillary forces directed this fluid into a chamber over the printed capture antibodies for binding. The fluid was then wicked from the other end of the channel using absorbent material. Flow rate through these capillary channels was controlled by choosing appropriate wicking material. This also ensures unidirectional flow of the sample. The protein biomarkers are quantified by an optical reader as the fluorescence of the spots is proportional to the analyte concentration. This technique enabled the rapid measurement of multiple protein biomarkers under flow conditions. The speed of the assay offers considerable advantages over more conventional antibody microarrays that require long incubation times.

Figure 22:
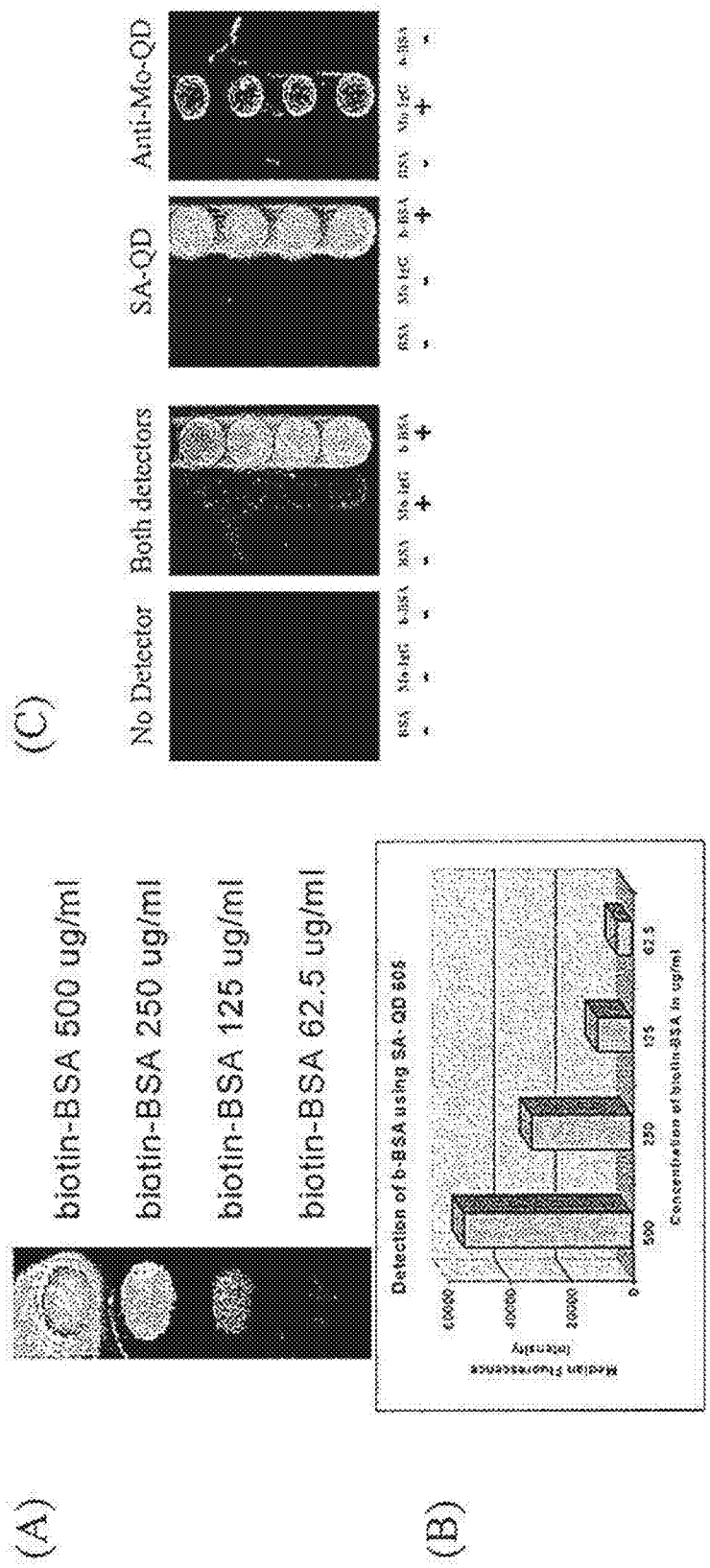
FIG. 22 shows the results of the proof of principle on microarray channels.

To demonstrate the proof of principle of quantitation using the channels, biotin-BSA was immobilized in a series of 4 dilutions from 500 μg/ml to 62.5 μg/ml. Streptavidin QD at 10 nM was used as reporter. The arrays were imaged and the fluorescent intensities of the spots was quantified and plotted in the FIGS. 22(A and B, respectively). The spots show an increase in fluorescent intensity with increased concentration. A linear response was observed in this assay demonstrating the principle that quantitative standard curves can be obtained using the microarray channel flow device. To demonstrate the multiplexing capability, two different capture molecules were used in quadruplicate (shown as columns in the FIG. 22(C)); biotin-BSA at 500 μg/ml and mouse IgG at 500 μg/ml. BSA was used as the negative control. Both spots and were washed with a mixture of streptavidin QD 605 (10 nM) and Goat anti-mouse IgG-QD 605 (10 nM) for 2 min. Observed in the FIG. 22(C) are four sets of spots. In the first set on the left, no reporter was used and we see no signal. In the second set, both streptavidin QD 605 and Goat anti-mouse IgG-QD 605 were used and fluorescence is observed in both the biotin-BSA and Mouse IgG spots. In the third set, only streptavidin QD 605 and therefore only the biotin-BSA spots show fluorescence. In this final set, only Goat anti-mouse IgG-QD 605 is used resulting in fluorescence only in the Mouse IgG spots. This demonstrated the specificity of the microarray channels and its ability to measure two different analytes simultaneously.

The biotin-BSA and Mouse IgG spots were observed with "comet tails" or streaks in the direction of flow in the channel. Since this assay was designed purely for the demonstration of proof of principle, the concentrations of the reagents were not optimized. As a result, too much capture molecule was deposited onto the glass surface, resulting in excess unbound ligand, which bound to the fluorescent reporter molecules in solutions and were smeared on the glass surface generating a streaking effect. To optimize spot morphology and minimize streaking, capture molecule concentrations should be optimized.

Flow Channel Standard Curves with Quantum Dots

Figure 23:
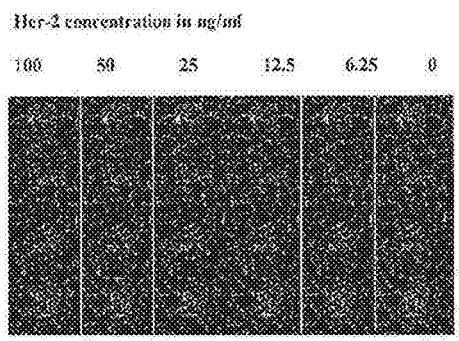
FIG. 23 shows standard curves using Quantum Dots on microarray channels.
Figure 23:
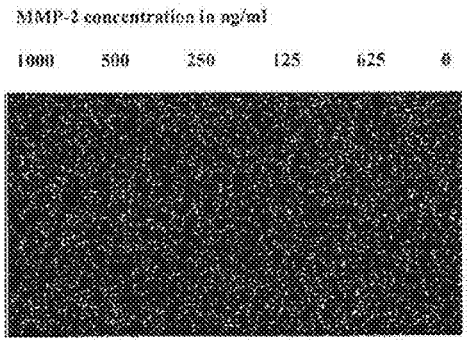
Figure 23:
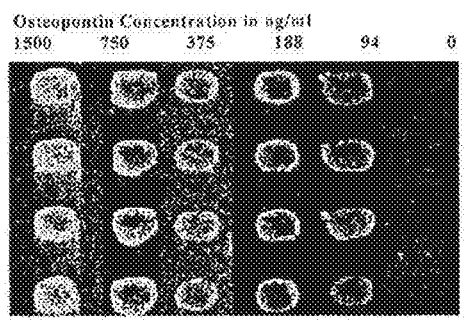
Figure 23:
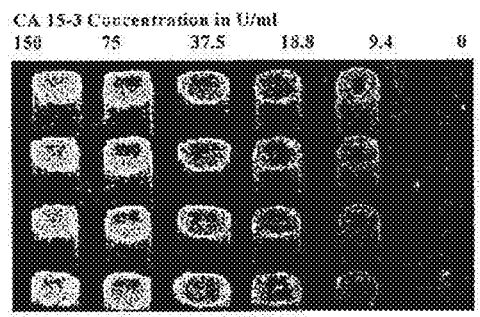
Figure 23:
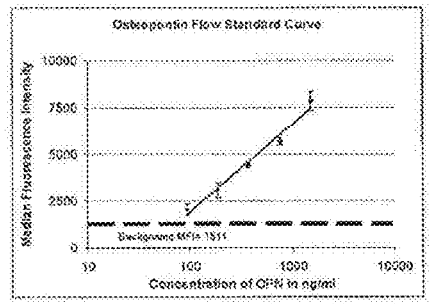
Figure 23:
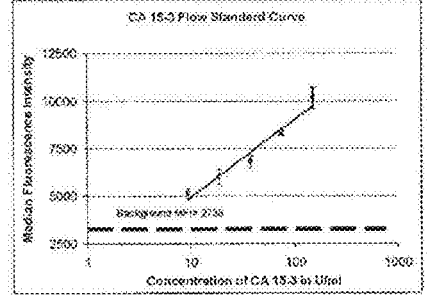

Standard curves were generated on flow channels by printing capture antibodies to the four protein biomarkers such that each antibody was present in quadruplicate within one channel. These arrays were incubated with 6 serial dilutions of recombinant antigen diluted in human serum. Standard curves were obtained on the protein microarray format for each biomarker. FIG. 23 shows a composite image of six different arrays with each column representing a different array that was incubated with increasing antigen concentration from right to left. Slides shown in Panel A were incubated with Her-2 at concentrations ranging from 6.25 ng/ml (right) to 100 ng/ml (left). Slides shown in Panel B were incubated with MMP-2 with a concentration range of 62.5 ng/ml (right) to 1000 ng/ml (left). Slides shown in Panel C were incubated with Osteopontin at concentrations from 94 ng/ml (right) to 1500 ng/ml (left) and those shown in Panel D were incubated with CA 15-3 at concentrations ranging from 9.4 U/ml (right)-150 U/ml (left). Channels with no antigen added were treated as background. The results show increased fluorescence intensity with increased protein concentration for Osteopontin and CA 15-3. The fluorescence from these spots is quantified using the Scanarray software and plotted as a function of antigen concentration in FIG. 23 (E-F) for these experiments. The standard curves were observed to be linear for Osteopontin and CA 15-3 in the clinically-relevant ranges. However, no signal from either Her-2 or MMP-2 was observed.

Figure 24:
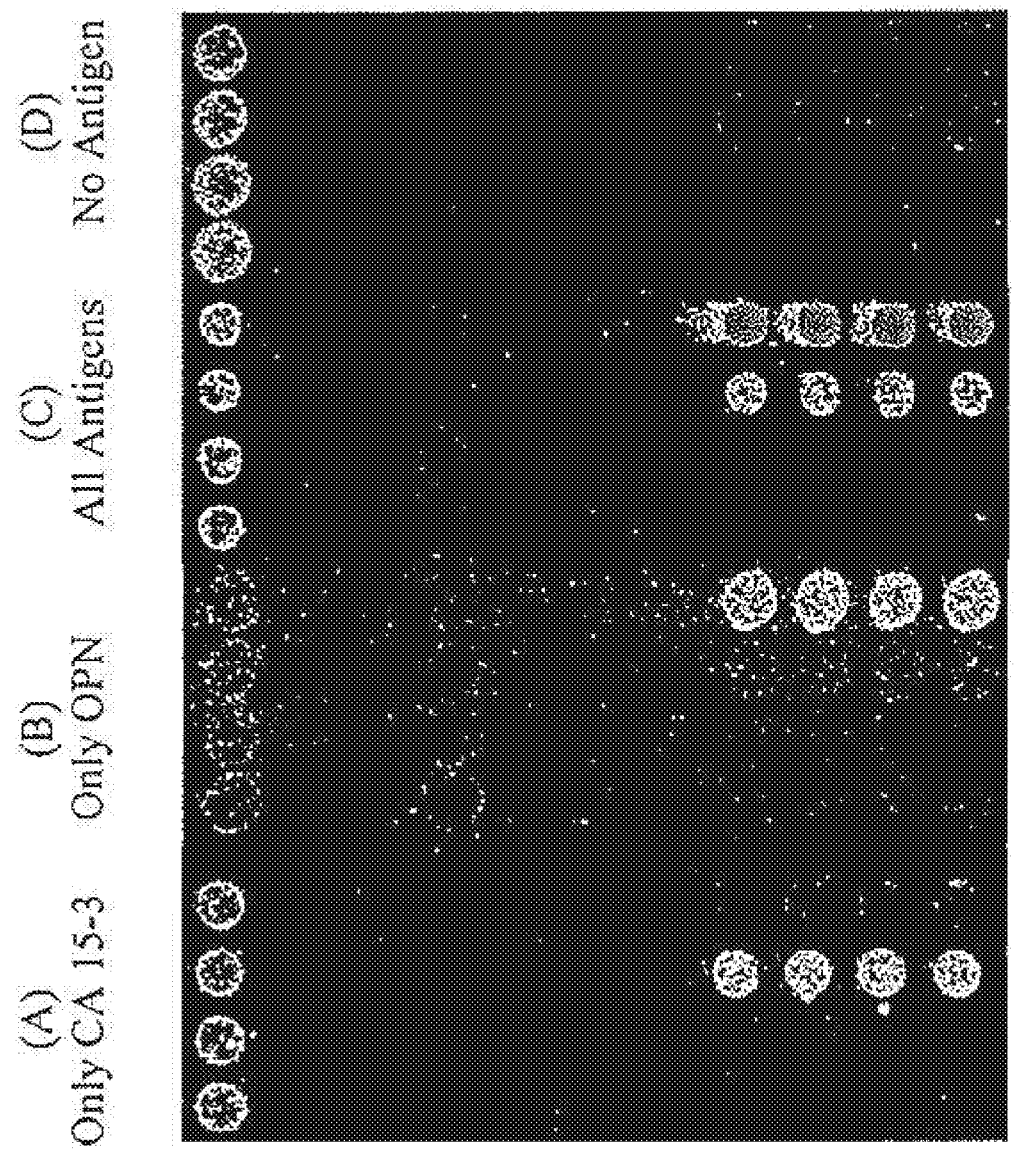
FIG. 24 shows the multiplex assay using Quantum Dots on microarray channels.

To further investigate and confirm these results, a multiplex assay was performed in which all four protein biomarkers were analyzed in one single microarray. In this experiment, four identical channels were printed with capture antibodies to the four protein biomarkers. As shown in FIG. 24, one of these slides was incubated with only CA 15-3 antigen, the second slide was incubated with only Osteopontin antigen, the third slide with all antigens and the fourth with no antigen. All four biotinylated antibodies were used in each assay. While the results for the assays involving OPN and CA 15-3 yielded accurate and specific signals from the correct capture antibody spots, no signal was obtained from Her-2 and MMP-2 spots in the case where all antigens were added. This indicated that the assay for Her-2 and MMP-2 was not sensitive when a rapid, one-step technique was employed.

Figure 25:
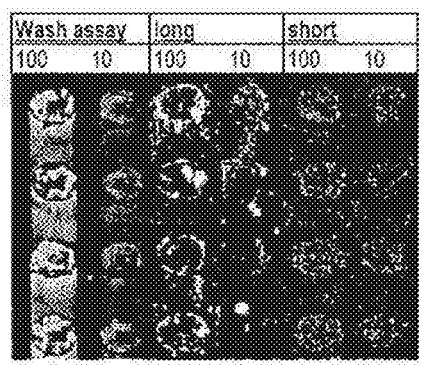
FIG. 25 shows the results of troubleshooting the Quantum Dot assay on microarray channels.
Figure 25:
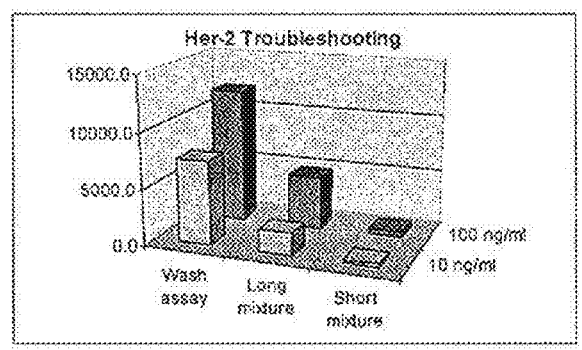
Figure 25:
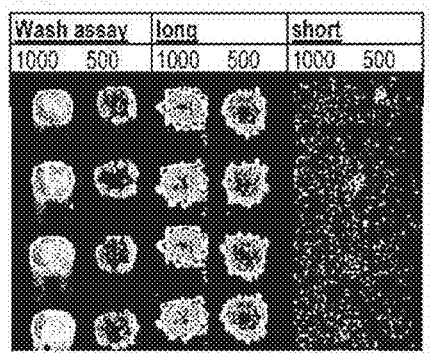
Figure 25:
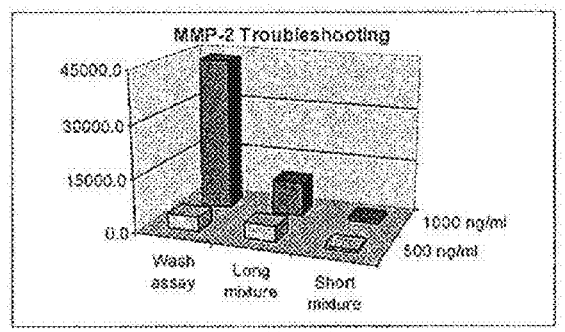

In order to troubleshoot the failure of Her-2 and MMP-2 detection on channels, sandwich assays on Her-2 and MMP-2 antigens were performed in three different formats. The first assay scheme was a "wash assay" which represented sequential incubation of assay reagents with washes in between, similar to a traditional microarray assay. The second scheme called "long assay" involved a one-step assay, where the antigen, biotinylated detector antibody and streptavidin QD 605 were premixed and incubated on the array for 60 min. The third assay scheme titled "short assay" was similar to the "long assay" except that the arrays were incubated for 30 min. In FIG. 25, the results from this test for Her-2 (A) and MMP-2 (B) are observed. Although the spots showed bright fluorescence for the wash assay, this signal was attenuated for the long assay in which no washes were included. This signal reached background levels for the short assay for both the antigens. The quantified signals are observed on the plot on the right hand side. This indicates that in order for the QD to be quantitative on the channel assays for Her-2 and MMP-2, they either need a long incubation time, or they need to be added individually to the arrays and cannot be pre-mixed with the sample. Therefore, Alexa 546 was adopted as the reporter for the channel assays since it had already been optimized in the above microarray assays.

Flow Channel Assays, Standard Curves Using Alexa 546

Figure 26:
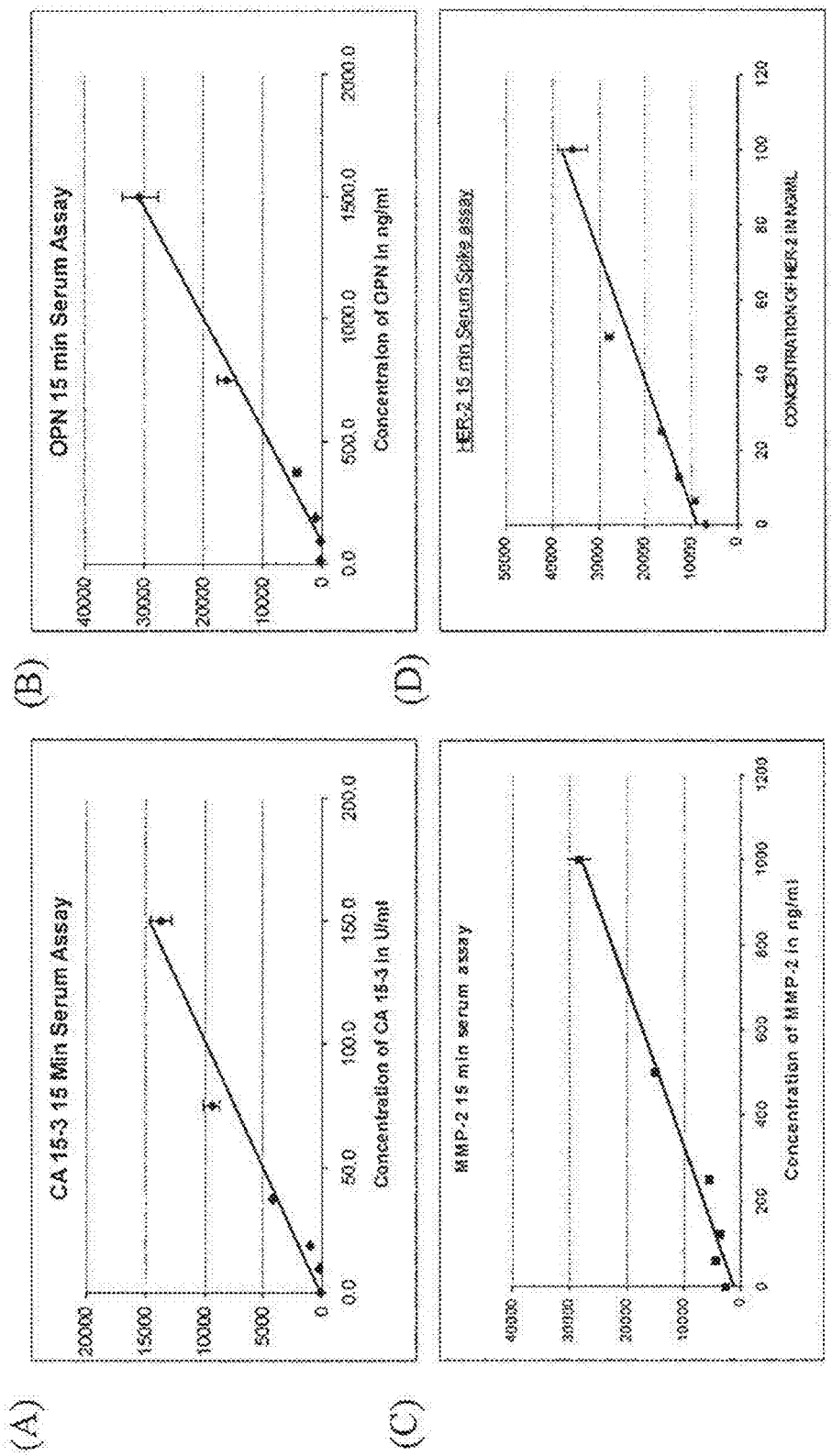
FIG. 26 is the standard curves obtained using microarray channels in 15 min.

Standard curves were performed on all four antigens using streptavidin Alexa 546 as the reporter instead of QD 605. FIG. 26 (A-D) shows the quantified fluorescence from the array spots plotted as a function of antigen concentration. Channels with no antigen added were treated as background. The mixture of antigen, biotinylated antibody and streptavidin Alexa 546 was allowed to incubate in the array in the channels for 15 min. Standard curves were obtained for each biomarker which are seen in FIG. 26 A-E. Data points for each curve represent the average intensities of two replicate samples (and hence eight different spots) with a coefficient of variation of approximately 15% for all protein biomarker curves. The standard curves for all four biomarkers appear to be linear in the clinically relevant ranges. Sensitive and linear response is observed for all the four biomarkers including Her-2 and MMP-2 in the concentration range selected. This therefore confirms that Alexa 546 works well as the molecular reporter for our multiplexed assay on microarray channels.

Multiplexed Assay on the Flow Channels

Figure 27:
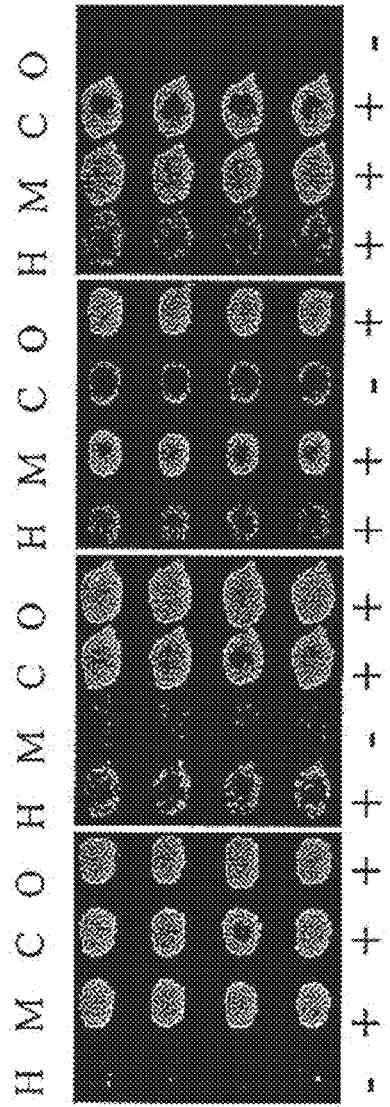
FIG. 27 is a demonstration of multiplexed immunoassays on microarray flow channels.
Figure 27:
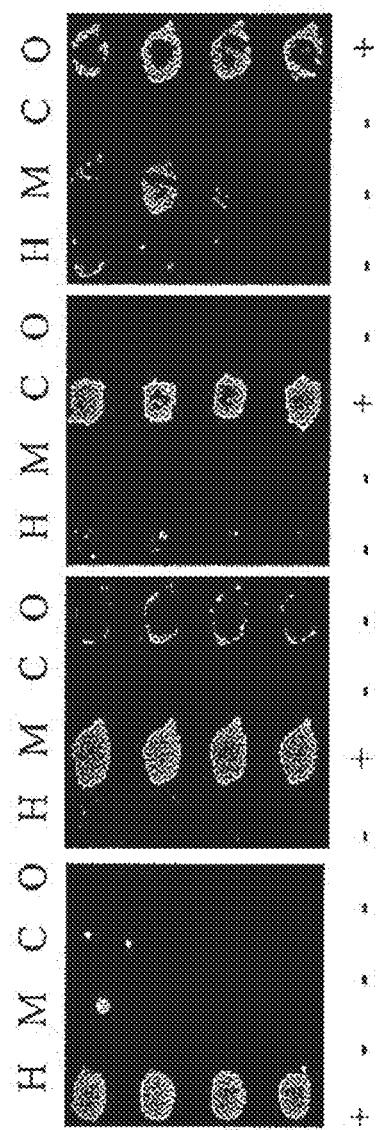

Microarray flow channels were used to simultaneously detect multiple biomarkers one single sample. In this experiment, eight identical slides were printed with capture antibodies to the four protein biomarkers printed in quadruplicate shown as columns in FIG. 27. O=OPN, C=CA 15-3, H=Her-2, and M=MMP-2. Four arrays were incubated with a mixture of all four but one biomarker (A) and the other four slides were incubated with only one antigen (B). Fluorescence was observed on the spots where the corresponding antigens were added. Some background signal is observed from the spots where no corresponding antigen was added to the mixture. Since human serum was used as the medium of dilution, the non specific binding of the serum proteins to the capture antibody spots as well as the low, normal circulating levels of the biomarkers generate this background signal from the spots even the recombinant antigen was not added. This data therefore demonstrates specific and sensitive detection of the four biomarkers in a multiplex format on the microarray channel device.

Figure 28:
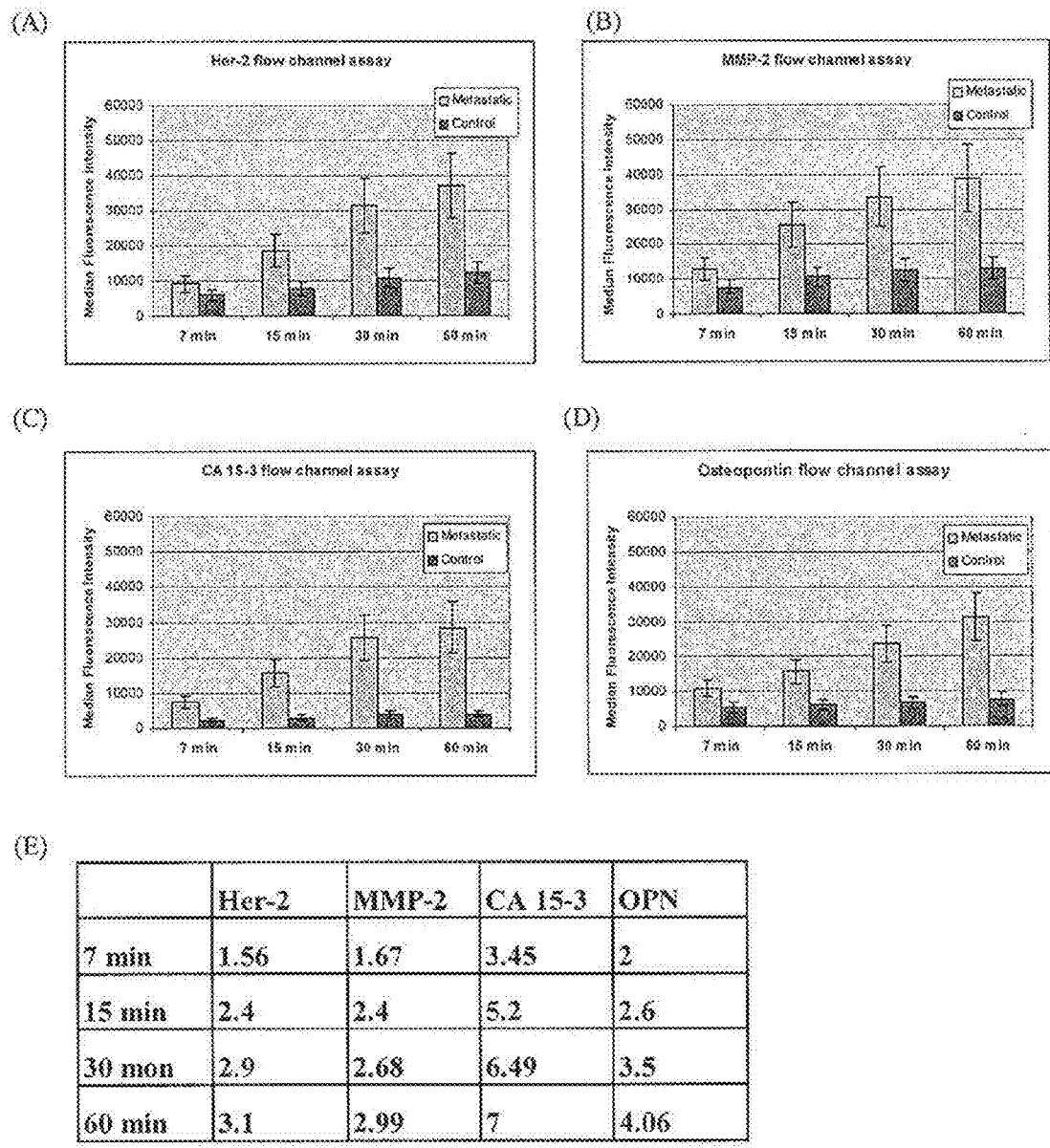
FIG. 28 is a determination of the best combination of assay speed and sensitivity for the microarray flow channels.

The new device platform was designed to measure multiple biomarkers and to produce rapid and reliable results in less than 15 minutes. Multiplexed assay with four different interaction times were therefore performed. A set of eight arrays were printed with all four capture antibodies. Four of these arrays were incubated with a mixture of all antigens in the high concentrations as observed in cancer, while the other set of four arrays was incubated with a mixture of all four antigens in the lower concentrations as observed in normal sera. The concentrations of antigens used to represent metastatic cancer were 30 ng/ml for Her-2, 850 ng/ml for MMP-2, 150 U/ml for CA 15-3 and 875 ng/ml for Osteopontin and the concentrations of antigens used to represent normal sera were 8 ng/ml for Her-2, 600 ng/ml for MMP-2, 15 U/ml for CA 15-3 and 440 ng/ml for Osteopontin. One array from each of the sets was incubated for 7 min, 15 min, 30 min and 60 min respectively. The median fluorescence intensities of the four biomarker spots were measured and are displayed in FIG. 28 (A-D). The fluorescent signal increases were observed with a longer incubation time for all the biomarkers. However, the difference between a 30 min incubation and 60 min incubation is not as drastic as the difference between a 7 min and 15 min incubation. This indicates that the assay reaches equilibrium somewhere between 30 and 60 minutes. Differential signal between the high concentrations (representing metastatic disease) and low concentrations (representing normal sera) is tabulated in FIG. 28 (E). The ratio of this differential signal shows that the ratio for the 7 minute incubation is below 2.0 but above 1.5 for Her-2 and MMP-2, however this ratio is very high for CA 15-3 and MMP-2. This implies that only CA 15-3 and Osteopontin are appropriate for a 7 min diagnostic test. However, all biomarkers have a ratio greater than 2 for a 15 min assay making this the best compromise between assay speed and sensitivity Flow Channel Patient Serum Immunoassays To test the power of the flow channels to resolve signals from cancer versus non-cancer samples accurately, breast cancer patient serum samples were incubated on antibody arrays. Since the serum samples were limited, the assay could not be performed with duplicates, similar to the protein microarrays. Therefore, this assay was designed in two parts. First, sera from 10 metastatic breast cancer patients and 10 control subjects was pooled to obtain a total of 800 µl of metastatic breast cancer sample and 800 µl of control sample. This assay eliminated the patient to patient variation, but enabled the measurement of technical variations across various channels and slides. An 80 µl aliquot of this pooled sample (mixed with biotinylated detector antibody cocktail and streptavidin Alexa 546) was drawn across 10 replicate arrays for 15 min. The resulting fluorescent intensities obtained for the four biomarkers are plotted in FIG. 29 (A). Significant differences between metastatic and control populations are observed for all four biomarkers with minimal technical variations (10%).

Figure 29:
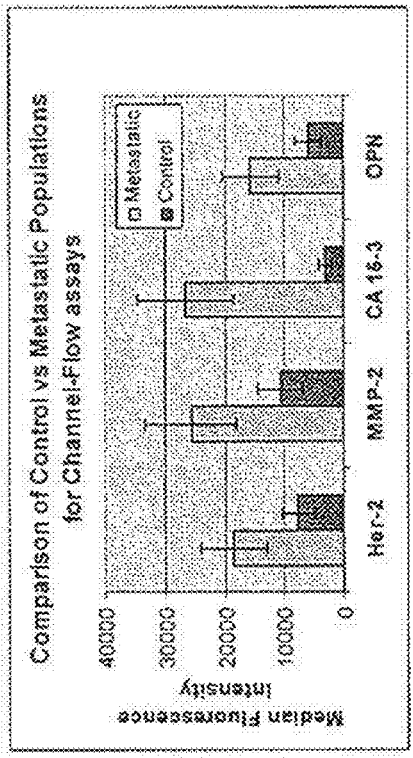
FIG. 29 shows biomarker concentration in patient serum samples.
Figure 29:
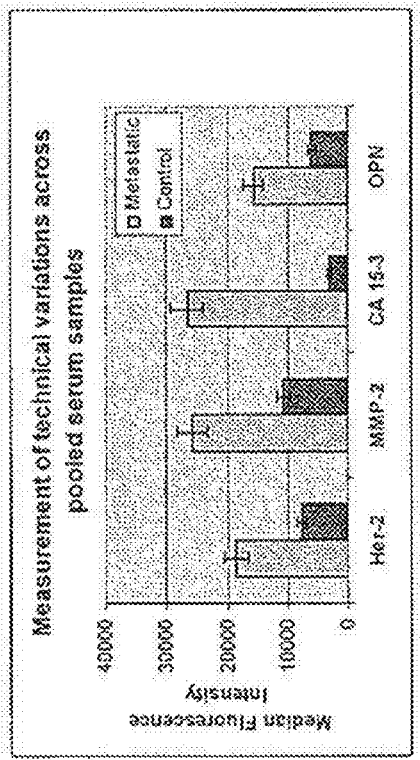

In the second part of this study, 80 µl of patient sera from 6 metastatic breast cancer patients and 6 control subjects was mixed with biotinylated detector antibody cocktail and streptavidin Alexa 546 reporter and incubated on the arrays for 15 minutes. The fluorescent signals from the four biomarkers were quantified and the median intensities were computed, which is shown in FIG. 29(B). A t-test was performed on the two sample sets (metastatic and control) for all four biomarkers and a p-value was generated to estimate the resolving power of the system for accurately identifying cancer vs. non-cancer samples. The table of these p-values is listed in FIG. 29 (C). We observe that there is a significant difference between the signals obtained for metastatic and control samples for CA 15-3 (C) and Osteopontin (D). This difference reduced for Her-2 (A) and MMP-2 (B), however, p value table indicates that the channel assay is sensitively ($p<0.05$) able to distinguish between metastatic and control populations for all four.

Optical Reader

Figure 30:
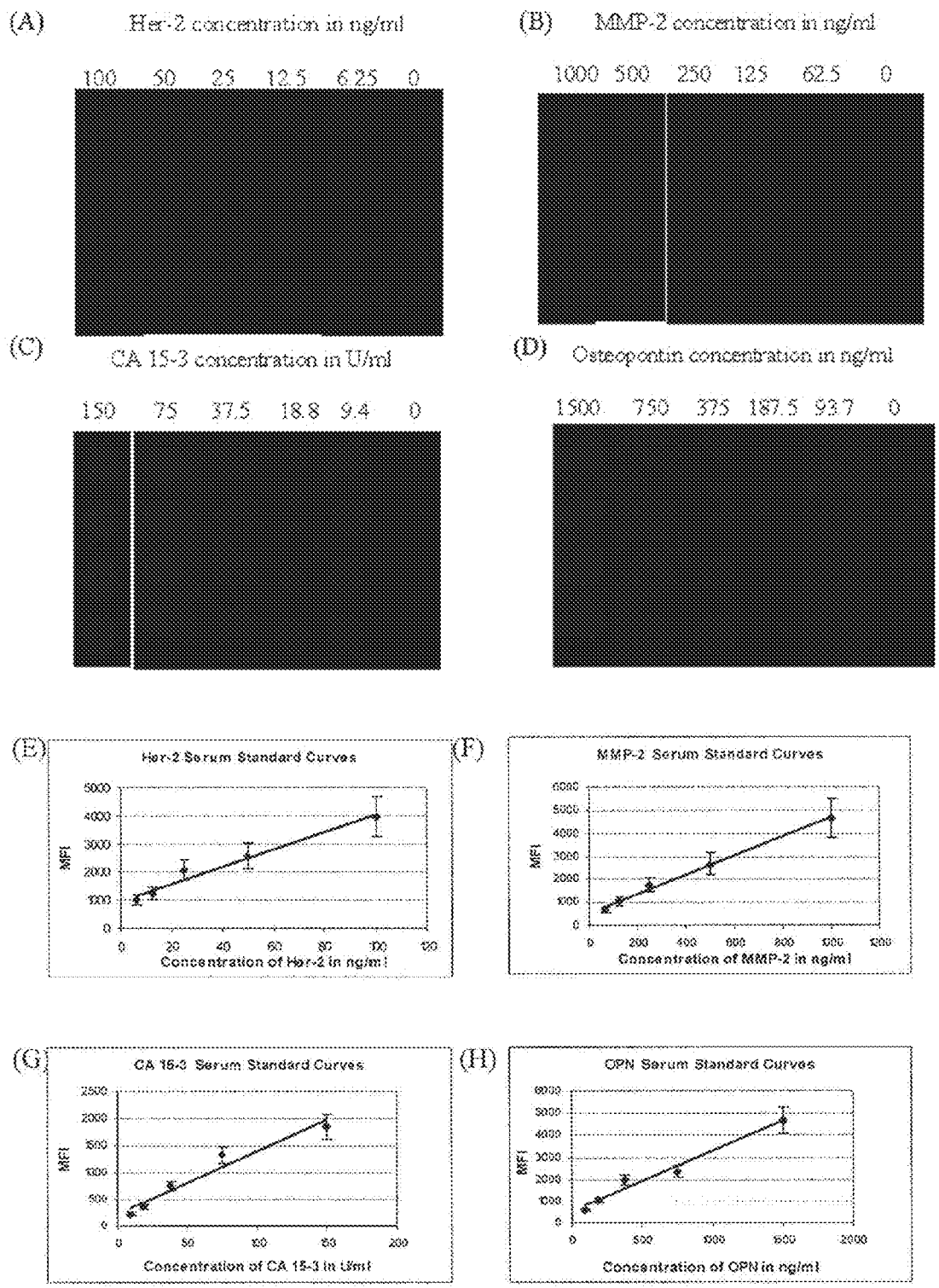
FIG. 30 shows imaging system standard curves.

A benchtop was built of a rugged, portable fluorescence imager, whose components include a miniature, megapixel CCD camera and a high power xenon arc lamp white light generator. Arrays were exposed to bandpass-filtered excitation light from the xenon source. The resulting emitted light was bandpass-filtered and collected by the CCD camera. The fluorescence images are exported to Scanarray™ for subsequent analysis, where background is calculated by taking into account the autofluorescence inherent to the glass slide and the non-specific binding of fluorescence probe material in the area surrounding the target spots on the array. FIG. 30 shows images of microarray channels used to obtain standard curves for all four biomarkers as captured by the CCD based imaging system. Channels shown in FIG. 30(A) were incubated with Her-2 at concentrations ranging from 6.25 ng/ml (right) to 100 ng/ml (left). Channels shown in Panel B were incubated with MMP-2 with a concentration range of 62.5 ng/ml (right) to 1000 ng/ml (left). Channels shown in Panel C were incubated with CA 15-3 at concentrations ranging from 9.4 U/ml (right)-150 U/ml (left) and those shown in Panel D were incubated with Osteopontin at concentrations from 94 ng/ml (right) to 1500 ng/ml (left). Human serum was used as the diluting medium in these assays. The results show increased fluorescence intensity with increased protein concentration.

The fluorescence from these spots was quantified using the Scanarray software and plotted as a function of antigen concentration in FIG. 30 (E-H). Data points for each curve represent the average intensities of eight replicates (background subtracted) obtained using quadruplicate spots in two replicate arrays. A linear relationship was observed between the concentration and fluorescent intensities for all four biomarkers.

Figure 31:
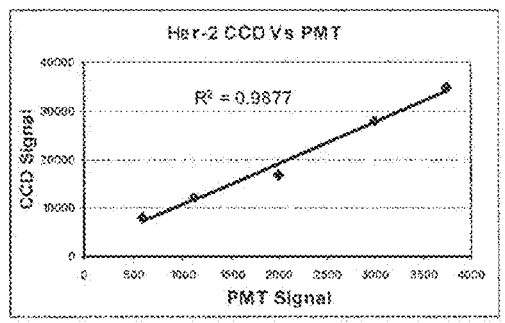
FIG. 31 is a comparison of the imaging system and a photomultiplier tube (PMT).
Figure 31:
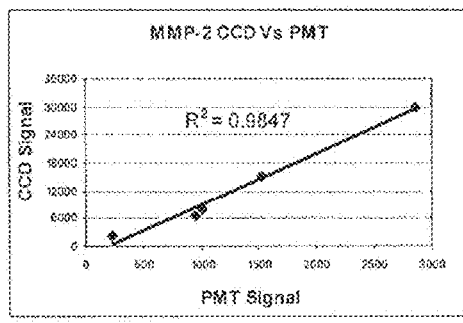
Figure 31:
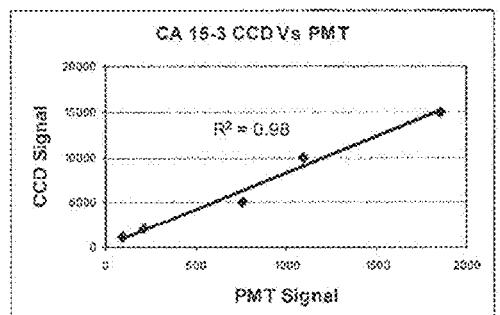
Figure 31:
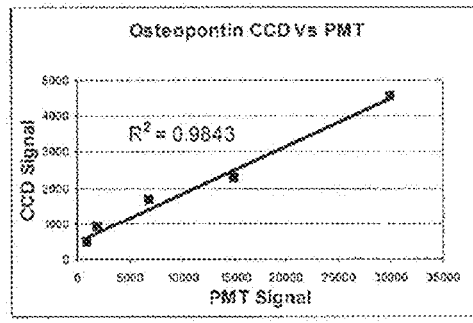
Figure 31:
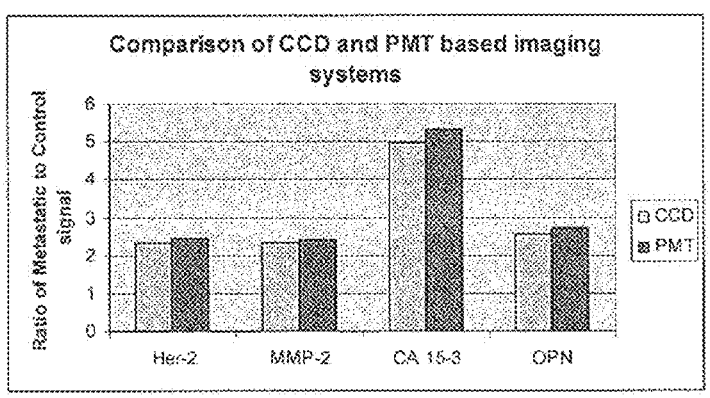

FIG. 31 (A-D) shows the comparison between the CCD and PMT based imaging systems for the quantification of dose response fluorescence. Data from the two methods showed a linear relationship with a correlation coefficient ($r^2$) of greater then 0.98, indicating that both methods produce similar results. This result is further supported by the results obtained from the multiplexed assays. The channels with arrays incubated with pooled patient samples from 10 metastatic and 10 control populations were imaged using the CCD system and compared the results to those obtained using the PMT. A ratio of the median fluorescence intensities obtained for metastatic populations to the median fluorescence intensities obtained for control populations is plotted in FIG. 31 (E) for the four biomarkers using both the CCD and PMT based imaging systems. The results from the CCD system are very similar to the ones obtained by using the PMT. A system was thus developed in which the high sensitivities of PMTs used in the large microarray scanners is matched by a miniature CCD camera by controlling the excitation light intensity and the integration time of the camera sensor.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

The invention claimed is:

1. A multiplex immunoassay detection device for simultaneous measurement of a plurality of distinct breast cancer markers in a patient serum sample, comprising:
    a glass solid support consisting of an array of antibody Clone 191924 for HER2, antibody Clone 36006.211 for MMP-2, antibody Clone M8071022 for CA-15-3 and antibody Clone 190312 for osteopontin;
    a glass cover plate, wherein the glass cover plate forms an upper surface positioned above the solid support;
    a vertical support comprising adhesive silicone, wherein the vertical support forms a connection between the solid support and the cover plate, the connection forming at least one channel surrounding the array of antibody Clone 191924 for HER2, antibody Clone 36006.211 for MMP-2, antibody Clone M8071022 for CA-15-3 and antibody Clone 190312 for osteopontin, and wherein the at least one channel comprises a first end and a second end and wherein the first end of the at least one channel comprises an opening;
    an absorbent material comprising a nitrocellulose membrane connected to the second end;
    and a set of biotinylated detection antibodies for detection of breast cancer markers bound to antibody Clone 191924 for HER2, antibody Clone 36006.211 for MMP-2, antibody Clone M8071022 for CA-15-3 and antibody Clone 190312 for osteopontin, the detection antibodies consisting of antibody clone AF-1129 for HER2, antibody clone AF-902 for MMP-2, antibody Clone M8071021 for CA 15-3 and antibody Clone AF-1433 for osteopontin.

2. A multiplex immunoassay method for detection of breast cancer markers HER2, MMP-2, CA 15-3, and osteopontin in a patient sample, comprising:
    providing a multiplex immunoassay detection device for simultaneous measurement of a plurality of distinct breast cancer markers in a patient serum sample, comprising:
    multiplex immunoassay detection device for simultaneous measurement of a plurality of distinct breast cancer markers in a patient serum sample, comprising:
    a glass solid support consisting of an array of antibody Clone 191924 for HER2, antibody Clone 36006.211 for MMP-2, antibody Clone M8071022 for CA-15-3 and antibody Clone 190312 for osteopontin;
    a glass cover plate, wherein the glass cover plate forms an upper surface positioned above the solid support;
    a vertical support comprising adhesive silicone, wherein the vertical support forms a connection between the solid support and the cover plate, the connection forming at least one channel surrounding the array of antibody Clone 191924 for HER2, antibody Clone 36006.211 for MMP-2, antibody Clone M8071022 for CA-15-3 and antibody Clone 190312 for osteopontin, and wherein the at least one channel comprises a first end and a second end and wherein the first end of the at least one channel comprises an opening; and
    an absorbent material comprising a nitrocellulose membrane connected to the second end;
    obtaining a first solution comprising the sample;
    incubating the first solution with a second solution comprising a set of biotinylated detection antibodies and streptavidin Alexa 546 under conditions to allow binding of the detection antibodies to the breast cancer markers, the set consisting of antibody AF-1129 for HER2, Antibody AF-902 for MMP-2, Antibody Clone M8071021 for CA 15-3 and antibody AF-1433 for osteopontin;
    applying the mixture of the first and second solutions to the open first end of the at least one channel of the multiplex immunoassay detection device;
    flowing the mixture through the at least one channel over the glass solid support under conditions to allow binding of all breast cancer markers to antibody Clone 191924 for HER2, antibody Clone 36006.211 for MMP-2, antibody Clone M8071022 for CA-15-3 and antibody Clone 190312 for osteopontin;
    washing the glass solid support to remove unbound sample, detection antibodies, and streptavidin Alexa 546; and
    detecting, with an optical reader, at least one fluorescent signal on the glass solid support, the fluorescent signal indicating the presence of at least one breast cancer maker in the sample.

3. The method of claim 2, wherein the patient sample comprises human blood serum.

4. The method of claim 2, further comprising comparing the detected fluorescent signal to standard curve fluorescent signal and quantifying the breast cancer marker present in the sample.

* * * * *